(12) United States Patent
Brode, III et al.

(10) Patent No.: US 6,436,690 B1
(45) Date of Patent: Aug. 20, 2002

(54) BPN' VARIANTS HAVING DECREASED ADSORPTION AND INCREASED HYDROLYSIS WHEREIN ONE OR MORE LOOP REGIONS ARE SUBSTITUTED

(75) Inventors: Philip Frederick Brode, III; Bobby Lee Barnett; Donn Nelton Rubingh, all of Cincinnati; Chanchal Kumar Ghosh, West Chester, all of OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 08/394,011

(22) Filed: Mar. 3, 1995

Related U.S. Application Data

(63) Continuation-in-part of application No. 08/287,461, filed on Aug. 11, 1994, and a continuation-in-part of application No. 08/237,939, filed on May 2, 1994, now abandoned, said application No. 08/287,461, is a continuation-in-part of application No. 08/121,437, filed on Sep. 15, 1993.

(51) Int. Cl.$^7$ .......................... C12N 9/56; C12N 15/57; C12N 15/74; C11D 3/386
(52) U.S. Cl. ................... 435/222; 435/69.1; 435/252.3; 435/320.1; 435/471; 510/392; 536/23.2
(58) Field of Search ........................... 435/222, 172.31, 435/252.3, 69.1, 471, 320.1; 536/23.2; 510/300, 226, 392, 326

(56) References Cited

U.S. PATENT DOCUMENTS

| | | | | |
|---|---|---|---|---|
| 4,760,025 A | * | 7/1988 | Estell et al. | 510/392 |
| 4,908,773 A | * | 3/1990 | Pantoliano et al. | 702/138 |
| 4,914,031 A | * | 4/1990 | Zukowski et al. | 435/222 |
| 4,980,288 A | * | 12/1990 | Bryan et al. | 435/222 |
| 4,990,452 A | * | 2/1991 | Bryan et al. | 435/222 |
| 5,013,657 A | * | 5/1991 | Bryan et al. | 435/222 |
| 5,116,741 A | * | 5/1992 | Bryan et al. | 435/87 |
| 5,118,623 A | * | 6/1992 | Boguslawski et al. | 510/374 |
| 5,155,033 A | * | 10/1992 | Estell et al. | 435/221 |
| 5,182,204 A | * | 1/1993 | Estell et al. | 435/222 |
| 5,185,258 A | * | 2/1993 | Caldwell et al. | 435/220 |
| 5,208,158 A | * | 5/1993 | Bech et al. | 435/219 |
| 5,217,878 A | * | 6/1993 | van Eekelen et al. | 435/69.1 |
| 5,240,632 A | * | 8/1993 | Brumbaugh | 510/226 |
| 5,244,791 A | * | 9/1993 | Estell | 435/68.1 |
| 5,246,849 A | * | 9/1993 | Bryan et al. | 435/220 |
| 5,260,207 A | * | 11/1993 | Pantoliano et al. | 435/221 |
| 5,275,945 A | * | 1/1994 | Hsiao et al. | 435/221 |
| RE34,606 E | * | 5/1994 | Estell et al. | 510/392 |
| 5,310,675 A | * | 5/1994 | Estell et al. | 435/320.1 |
| 5,316,941 A | * | 5/1994 | Estell et al. | 435/252.3 |
| 5,324,653 A | * | 6/1994 | van Eekelen et al. | 435/221 |
| 5,336,611 A | * | 8/1994 | van Eekelen et al. | 435/221 |
| 5,340,735 A | * | 8/1994 | Christianson et al. | 435/221 |
| 5,346,823 A | * | 9/1994 | Estell et al. | 435/221 |
| 5,352,603 A | * | 10/1994 | Vetter et al. | 435/221 |
| 5,371,008 A | * | 12/1994 | Carter et al. | 435/222 |
| 5,371,190 A | * | 12/1994 | Carter et al. | 530/350 |
| 5,389,307 A | * | 2/1995 | Lindegaard et al. | 510/320 |
| 5,397,705 A | * | 3/1995 | Zukowski et al. | 435/222 |
| 5,403,737 A | * | 4/1995 | Abrahmsen et al. | 435/252.3 |
| 5,441,882 A | * | 8/1995 | Estell et al. | 435/222 |
| 5,453,372 A | * | 9/1995 | Vetter et al. | 435/222 |
| 5,470,733 A | * | 11/1995 | Bryan et al. | 435/222 |
| 5,472,855 A | * | 12/1995 | Carter et al. | 435/68.1 |
| 5,482,849 A | * | 1/1996 | Branner et al. | 435/222 |
| 5,500,364 A | * | 3/1996 | Christianson et al. | 435/221 |
| 5,567,601 A | * | 10/1996 | Bryan et al. | 435/222 |
| 5,629,173 A | * | 5/1997 | Abrahmsen et al. | 435/68.1 |
| 5,631,217 A | * | 5/1997 | Branner et al. | 510/320 |
| 5,652,136 A | * | 7/1997 | Carter et al. | 435/252.3 |
| 5,665,587 A | * | 9/1997 | Aaslyng et al. | 435/221 |
| 5,677,272 A | * | 10/1997 | Ghosh et al. | 510/306 |
| 5,679,630 A | * | 10/1997 | Baeck et al. | 510/305 |
| 5,700,676 A | * | 12/1997 | Bott et al. | 435/221 |
| 5,707,848 A | * | 1/1998 | Bryan et al. | 435/6 |

(List continued on next page.)

FOREIGN PATENT DOCUMENTS

| | | |
|---|---|---|
| AU | 8772281 | 11/1987 |
| EP | 0 251 446 A2 * | 4/1987 |
| EP | 0 260 105 | 3/1988 |

(List continued on next page.)

OTHER PUBLICATIONS

Thomas, P. G., et al., 1985, "Tailoring the pH dependence of enzyme catalysis using protein engineering to change a single amino acid at BPN' position 99: D99S reduces pKa", Nature, vol. 318, pp. 375–376.*

Russell, A. J. & Fersht, A. R., 1987, "Rational modification of enzyme catalysis by engineering surface charge", Nature, vol. 328, pp. 496–500.*

Siezen, R. J., et al., 1991, "Homology modelling and protein engineering strategy of subtilases, the family of subtilisin–like serine proteases", Protein Engineering, vol. 4, pp. 719–737.*

(List continued on next page.)

Primary Examiner—Charles L. Patterson, Jr.
Assistant Examiner—William W. Moore
(74) Attorney, Agent, or Firm—Bart S. Hersko; Brahm J. Corstanje; Karen F. Clark

(57) ABSTRACT

The present invention relates to subtilisin BPN' variants having a modified amino acid sequence of wild-type BPN' amino acid sequence, the wild-type amino acid sequence comprising a first loop region, a second loop region, a third loop region, a fourth loop region and a fifth loop region; wherein the modified amino acid sequence comprises different amino acids than that occurring in wild-type subtilisin BPN' (i.e., substitution) at specifically identified positions in one or more of the loop regions whereby the BPN' variant has decreased adsorption to, and increased hydrolysis of, an insoluble substrate as compared to the wild-type subtilisin BPN'. The present invention also relates to the genes encoding such subtilisin BPN' variants. The present invention also relates to compositions comprising such subtilisin BPN' variants for cleaning a variety of surfaces.

63 Claims, No Drawings

U.S. PATENT DOCUMENTS

| | | | | |
|---|---|---|---|---|
| 5,736,512 A | * | 4/1998 | Abrahmsen et al. | 514/12 |
| 5,741,664 A | * | 4/1998 | Ballinger et al. | 435/68.1 |
| 5,741,694 A | * | 4/1998 | Hastrup et al. | 435/222 |
| 5,763,257 A | * | 6/1998 | Bott et al. | 435/221 |
| 5,801,038 A | * | 9/1998 | Bott et al. | 435/221 |
| 5,801,039 A | * | 9/1998 | Maurer et al. | 435/221 |
| 5,955,340 A | * | 9/1999 | Bott et al. | 435/221 |
| 5,972,682 A | * | 10/1999 | Bott et al. | 435/221 |
| 5,985,639 A | * | 11/1999 | Christianson et al. | 435/221 |
| 6,197,567 B1 | * | 3/2001 | Aaslyng et al. | 435/221 |
| 6,197,589 B1 | * | 3/2001 | Maurer et al. | 435/471 |
| 6,271,012 B1 | * | 8/2001 | van Eekelen et al. | 435/221 |
| 6,287,841 B1 | * | 9/2001 | Mulleners et al. | 435/221 |

FOREIGN PATENT DOCUMENTS

| | | | |
|---|---|---|---|
| EP | 0 260 105 A1 | * | 3/1988 |
| EP | 0 328 229 | | 8/1989 |
| EP | 0 328 229 A1 | * | 8/1989 |
| EP | 0 357 157 A1 | * | 3/1990 |
| EP | 0 380 362 A1 | * | 8/1990 |
| EP | 0 380 362 | | 8/1990 |
| EP | 0 398 539 A1 | * | 11/1990 |
| EP | 0 398 539 | | 11/1990 |
| EP | 0 405 901 A1 | * | 1/1991 |
| EP | 0 405 901 A1 | | 1/1991 |
| EP | 0 405 902 A1 | | 1/1991 |
| EP | 0 405 902 A1 | * | 1/1991 |
| WO | WO 87/04461 A1 | * | 7/1987 |
| WO | 87/04461 | | 7/1987 |
| WO | WO 87/05050 A1 | * | 8/1987 |
| WO | 87/05050 | | 8/1987 |
| WO | WO 88/08033 A1 | * | 10/1988 |
| WO | WO 89/06279 A1 | * | 1/1989 |
| WO | 89/06279 | | 1/1989 |
| WO | WO 89/07462 A1 | * | 8/1989 |
| WO | WO 89/09830 A1 | * | 10/1989 |
| WO | 89/09830 | | 10/1989 |
| WO | WO 91/00345 A1 | * | 1/1991 |
| WO | 91/00345 | | 1/1991 |
| WO | WO 91/14420 A1 | * | 11/1991 |
| WO | WO 92/02615 A1 | * | 2/1992 |
| WO | WO 92/08778 A1 | * | 5/1992 |
| WO | WO 92/11357 A1 | * | 7/1992 |
| WO | 92/11357 | | 7/1992 |
| WO | 94/02618 | | 2/1994 |
| WO | WO 94/02618 A1 | * | 2/1994 |
| WO | WO 95/07991 A2 | * | 3/1995 |
| WO | 95/07991 | | 3/1995 |
| WO | WO 95/30010 A1 | * | 4/1995 |
| WO | WO 95/30011 A1 | * | 4/1995 |
| WO | WO 88/08028 A1 | * | 10/1998 |

OTHER PUBLICATIONS

Thomas, P. G., et al., Nature, vol. 318, "Tailoring the pH dependence of enzyme catalysis using protein engineering", pp. 375–376, 1985.*

Abrahmsén, L., J. Tom, J. Burnier, K. A. Butcher, A. Kossiakoff and J. A. Wells, "Engineering Subtilisin and its Substrates for Efficient Ligation of Peptide Bonds in Aqueous Solution", Biochemistry, vol. 30, No. 17, pp. 4151–4159 (no month identified 1991).

Arnold, F.H., "Engineering Enzymes for Non–aqueous Solvents", Tib Tech, vol. 8, pp. 244–249 (Sep. 1990).

Braxton, S. and J. A. Wells, "The Importance of a Distal Hydrogen Bonding Group in Stabilizing the Transition State in Subtilisin BPN'", The Journal of Biology Chemistry, vol. 266, No. 18, pp. 11797–11800 (Jun. 1991).

Brode, P.F. III and D.S. Rauch, "Subtilisin BPN': Activity on an Immobilized Substrate", Langmuir, vol. 8, No. 5, pp. 1325–1329 (no month identified 1992).

Brode, P.F. III, C.R. Erwin, D.S. Rauch, E.S. Wang, J.M. Armpriester, B.L. Barnett, M.D. Bauer, P.R. Green, D.A. Thaman, and D.N. Rubingh, "Surface Active Variants of Subtilisin BPN': Interfacial Hydrolysis", Abstract, Keystone Symposium (Mar. 6–11, 1994).

Carter, P., L. Abrahmsén and J. A. Wells, "Probing the Mechansim and Improving the Rate of Substrate–Assisted Catalysis in Subtilisin BPN'", Biochemistry, vol. 30, No. 25, pp. 6142–6148 (no month identified 1991).

Carter, P. and J. A. Wells, "Functional Interaction Among Catalytic Residues in Subtilisin BPN'", Proteins: Structure, Function, and Genetics, vol. 7, pp. 335–342, (no month identified 1990).

Cunningham, B. C. and J. A. Wells, "Improvement in the Alkaline Stability of Subtilisin Using An Efficient Random Mutagenesis and Screening Procedure", Protein Engineering, vol. 1, No. 4, pp. 319–325 (no month identified 1987).

Egmond, M. R., W. P. Antheunisse, P. Ravestein, A. T. A. Mooren and J. de Vileg, "Engineering Surface Charges In A Subtilisin ", First International Symposium on Subtilisin Enzymes, Hamburg, Germany, (Sep. 1992).

Estell, D.A., "Engineering Enzymes for Improved Performance in Industrial Applications", Journal of Biotechnology, vol. 28, No. 1, pp. 25–30 (Jan. 1993).

Hopp, T. P. and K. R. Woods, "Prediction of Protein Antigenic Determinants From Amino Acid Sequences", Proc. Natl. Acad. Sci. USA, vol. 78, No. 6, pp. 3824–3828 (Jun. 1981).

Mitchinson, C. and J.A. Wells, "Protein Engineering of Disulfide Bonds in Subtilisin BPN'", Biochemistry, vol. 28, No. 11, pp. 4807–4815 (no month identified 1989).

Mizushima, N., D. Spellmeyer, S. Hirono, D. Pearlman and P. Kollman, "Free Energy Perturbation Calculations on Binding and Catalysis ater Mutating Threonine 220 in Subtilisin", Journal of Biological Chemistry, vol. 266, No. 18, pp. 11801–11809 (Jun. 1991).

Pantoliano, M.W., M. Whitlow, J.F. Wood, S.W. Dodd, K.D. Hardman, M.L. Rollence and P.N. Bryan, "Large Increases in General Stability for Subtilisin BPN' through Incremental Changes in the Free Energy of Unfolding", Biochemistry, vol. 28, No. 18, pp. 7205–7213 (no month identified 1989).

Russell, A. J. and A. R. Fersht, "Rational Modification of Enzyme Catalysis by Engineering Surface Charge", Nature, vol. 328, pp. 496–500 (Aug. 1987).

Siezen. R.J., W.M. de Vos, J.A.M. Leunissen and B.W. Dijkstra, "Homology Modelling and Protein Engineering Strategy of Subtilases, the Family of Subtilisin–like Serine Proteinases", Prot. Eng., vol. 4, No. 7, pp. 719–737 (no month identified 1991).

Sternberg, M. J. E., F. R. F. Hayes, A. J. Russell, P. G. Thomas and A. R. Fersht, "Prediction of Electrostatic Effects of Engineering of Protein Charges", Nature, vol. 330, pp. 86–88 (Nov. 1987).

Wells, J.A., B.C. Cunningham, T.P. Graycar and D.A. Estell, "Recruitment of Substrate–specificity Properties from One Enzyme into a Related One by Protein Engineering", Proc. Natl. Acad. Sci., USA,, vol. 84, pp. 5167–5171 (Aug. 1987).

Wells, J.A. and D.A. Estell, "Subtilisin–An Enzyme Designed to be Engineered", TIBS 13, pp. 291–297 (Aug. 1988).

Wong, C.–H., S.–T. Chen, W. J. Hennen, J. A. Bibbs, Y.–F. Wang, J. L.–C. Liu, M. W. Pantoliano, M. Whitlow and P. N. Bryan, "Enzymes in Organic Synthesis: Use of Subtilisin and a Highly Stable Mutant Derived from Multiple Site–Specific Mutations", J. Am. Chem. Soc., vol. 112, No. 3, pp. 945–953 (no month identified 1990).

* cited by examiner

US 6,436,690 B1

BPN' VARIANTS HAVING DECREASED ADSORPTION AND INCREASED HYDROLYSIS WHEREIN ONE OR MORE LOOP REGIONS ARE SUBSTITUTED

This is a continuation-in-part of application Ser. No. 08/287,461, filed on Aug. 11, 1994, and a continuation-in-part of application Ser. No. 08/237,939, filed on May 2, 1994 now abandoned; of wich application Ser. No. 08/287,461, filed on Aug. 11, 1994 is a continuation-in-part of application Ser. No. 08/121,437, filed on Sep. 15, 1993.

TECHNICAL FIELD

The present invention relates to novel enzyme variants useful in a variety of cleaning compositions, and the genes encoding such enzyme variants.

BACKGROUND

Enzymes make up the largest class of naturally occurring proteins. Each class of enzyme generally catalyzes (accelerates a reaction without being consumed) a different kind of chemical reaction. One class of enzymes known as proteases, are known for their ability to hydrolyze (break down a compound into two or more simpler compounds with the uptake of the H and OH parts of a water molecule on either side of the chemical bond cleaved) other proteins. This ability to hydrolyze proteins has been taken advantage of by incorporating naturally occurring and protein engineered proteases as an additive to laundry detergent preparations. Many stains on clothes are proteinaceous and wide-specificity proteases can substantially improve removal of such stains.

Unfortunately, the efficacy level of these proteins in their natural, bacterial environment, frequently does not translate into the relatively unnatural wash environment. Specifically, protease characteristics such as thermal stability, pH stability, oxidative stability and substrate specificity are not necessarily optimized for utilization outside the natural environment of the enzyme.

The amino acid sequence of the protease determines the characteristics of the protease. A change of the amino acid sequence of the protease may alter the properties of the enzyme to varying degrees, or may even inactivate the enzyme, depending upon the location, nature and/or magnitude of the change in the amino acid sequence. Several approaches have been taken to alter the wild-type amino acid sequence of proteases in an attempt to improve their properties, with the goal of increasing the efficacy of the protease in the wash environment. These approaches include altering the amino acid sequence to enhance thermal stability and to improve oxidation stability under quite diverse conditions.

Despite the variety of approaches described in the art, there is a continuing need for new effective variants of proteases useful for cleaning a variety of surfaces.

OBJECTS OF THE PRESENT INVENTION

It is an object of the present invention to provide subtilisin enzyme variants having improved hydrolysis versus the wild-type of the enzyme.

It is also an object of the present invention to provide cleaning compositions comprising these subtilisin enzyme variants.

SUMMARY

The present invention relates to subtilisin BPN' variants having a modified amino acid sequence of wild-type BPN' amino acid sequence, the wild-type amino acid sequence comprising a first loop region, a second loop region, a third loop region, a fourth loop region and a fifth loop region; wherein the modified amino acid sequence comprises different amino acids than that occurring in wild-type subtilisin BPN' (i.e., substitution) at specifically identified positions in one or more of the loop regions whereby the BPN' variant has decreased adsorption to, and increased hydrolysis of, an insoluble substrate as compared to the wild-type subtilisin BPN'. The present invention also relates to the genes encoding such subtilisin BPN' variants. The present invention also relates to compositions comprising such subtilisin BPN' variants for cleaning a variety of surfaces.

DESCRIPTION

I. Subtilisin Variants

This invention pertains to subtilisin enzymes, in particular BPN', that have been modified by mutating the various nucleotide sequences that code for the enzyme, thereby modifying the amino acid sequence of the enzyme. The modified subtilisin enzymes (hereinafter, "BPN' variants") of the present invention have decreased adsorption to and increased hydrolysis of an insoluble substrate as compared to the wild-type subtilisin. The present invention also pertains to the mutant genes encoding for such BPN' variants.

The subtilisin enzymes of this invention belong to a class of enzymes known as proteases. A protease is a catalyst for the cleavage of peptide bonds. One type of protease is a serine protease. A serine protease is distinguished by the fact that there is an essential serine residue at the active site.

The observation that an enzyme's rate of hydrolysis of soluble substrates increases with enzyme concentration is well documented. It would therefore seem plausible that for surface bound substrates, such as is encountered in many cleaning applications, the rate of hydrolysis would increase with increasing surface concentration. This has been shown to be the case. (Brode, P. F. III and D. S. Rauch, LANGMUIR, "Subtilisin BPN': Activity on an Immobilized Substrate", Vol. 8, pp. 1325–1329 (1992)). In fact, a linear dependence of rate upon surface concentration was found for insoluble substrates when the surface concentration of the enzyme was varied. (Rubingh, D. N. and M. D. Bauer, "Catalysis of Hydrolysis by Proteases at the Protein-Solution Interface," in Polymer Solutions, Blends and Interfaces, Ed. by I. Noda and D. N. Rubingh, Elsevier, p. 464 (1992)). Surprisingly, when seeking to apply this principle in the search for variant proteases which give better cleaning performance, we did not find that enzymes which adsorb more give better performance. In fact, we surprisingly determined the opposite to be the case: decreased adsorption by an enzyme to a substrate resulted in increased hydrolysis of the substrate (i.e., better cleaning performance).

While not wishing to be bound by theory, it is believed that improved performance, when comparing one variant to another, is a result of the fact that enzymes which adsorb less are also less tightly bound and therefore more highly mobile on the surface from which the insoluble protein substrate is to be removed. At comparable enzyme solution concentrations, this increased mobility is sufficient to outweigh any advantage that is conferred by delivering a higher concentration of enzyme to the surface.

The mutations described herein are designed to change (i.e., decrease) the adsorption of the enzyme to surface-bound soils. In BPN', certain amino acids form exterior loops on the enzyme molecule. For purposes of discussion, these loops shall be referred to as first, second, third, fourth and fifth loop regions. Specifically, positions 59–66 form the first loop region; positions 95–107 form the second loop region; positions 126–133 form the third loop region; positions 154–167 form the fourth loop region; positions 187–191 form the fifth loop region; and positioins 199–220 form the sixth loop region (position numbering analagous to positions in the amino acid sequence for wild-type subtilisin BPN' (SEQ ID NO:1)).

It believed that these loop regions play a significant role in the adsorption of the enzyme molecule to a surface-bound peptide, and specific mutations in one or more of these loop regions will have a significant effect on this adsorption. While not wishing to be bound by theory, it is believed that the loop regions are important to the adsorption of the BPN' molecule for at least two reasons. First, the amino acids which comprise the loop regions can make close contacts with any surfaces to which the molecule is exposed. Second, the proximity of the loop regions to the active-site and binding pocket of the BPN' molecule gives them a role in the catalytically productive adsorption of the enzyme to surface-bound substrates (peptides/protein soils).

As used herein, "variant" means an enzyme having an amino acid sequence which differs from that of wild-type.

As used herein, "mutant BPN' gene" means a gene coding for a BPN' variant.

As used herein, "wild-type subtilisin BPN'" refers to a subtilisin enzyme represented by SEQ ID NO:1. The amino acid sequence for subtilisin BPN' is further described by Wells, J. A., E. Ferrari, D. J. Henner, D. A. Estell and E. Y. Chen, Nucleic Acids Research, Vol. II, 7911–7925 (1983), incorporated herein by reference.

As used herein, the term "wild-type amino acid sequence" encompasses SEQ ID NO:1 as well as SEQ ID NO:1 having modifications to the amino acid sequence other than at any of positions 59–66, 95–107, 126–133, 154–167, 187–191 and 199–220.

As used herein, "more hydrophilic amino acid" refers to any other amino acid having greater hydrophilicity than a subject amino acid with reference to the hydrophilicity table below. The following hydrophilicity table (Table 1) lists amino acids in descending order of increasing hydrophilicity (see Hopp, T. P., and Woods, K. R., "Prediction of Protein Antigenic Determinants from Amino Acid Sequences", Proceedings of the National Academy of Science USA, Vol. 78, pp. 3824–3828, 1981, incorporated herein by reference).

TABLE 1

| Amino Acid | Hydrophilicity Value |
|---|---|
| Trp | −3.4 |
| Phe | −2.5 |
| Tyr | −2.3 |
| Leu, Ile | −1.8 |
| Val | −1.5 |
| Met | −1.3 |
| Cys | −1.0 |
| Ala, His | −0.5 |
| Thr | −0.4 |
| Pro, Gly | −0.0 |
| Gln, Asn | 0.2 |
| Ser | 0.3 |
| Arg$^+$, Lys$^+$, Glu$^-$, Asp$^-$ | 3.0 |

Table 1 also indicates which amino acids carry a charge (this characteristic being based on a pH of from about 8–9). The positively charged amino acids are Arg and Lys, the negatively charged amino acids are Glu and Asp, and the remaining amino acids are neutral. In a preferred embodiment of the present invention, the substituting amino acid is either neutral or negatively charged, more preferably negatively charged (i.e., Glu or Asp).

Therefore, for example, the statement "substitute Gln with an equally or more hydrophilic amino acid which is neutral or has a negative charge" means Gln would be substituted with Asn (which is equally hydrophilic to Gln), or Ser, Glu or Asp (which are more hydrophilic than Gln); each of which are neutral or have a negative charge, and have a greater hydrophilicity value as compared to Gln. Likewise, the statement "substitute Pro with a more hydrophilic amino acid which is neutral or has a negative charge" means Pro would be substituted with Gln, Asn, Ser, Glu or Asp.

In one embodiment of the present invention, the BPN' variant has a modified amino acid sequence of wild-type amino acid sequence, wherein the modified amino acid sequence comprises a substitution at one or more positions in one or more of the first, second, third, fourth or fifth loop regions; whereby the BPN' variant has decreased adsorption to, and increased hydrolysis of, an insoluble substrate as compared to the wild-type subtilisin BPN'.

In another embodiment of the present invention, the BPN' variant further comprises one or more substitutions to the sixth loop region.

In a preferred embodiment of the present invention, the substituting amino acid for one or more of the positions in one or more of the loop regions is, with reference to Table 1, neutral or negatively charged and equally or more hydrophylic, preferably more hydrophylic, than the amino acid at the subject position in the wild-type amino acid sequence.

A. Substitutions in the First Loon Region

When a substitution occurs in the first loop region, the substitution occurs at one or more of positions 59, 60, 61, 62, 63, 65 or 66.

When a substitution occurs at position 59, the substituting amino acid is Asn, Asp, Glu or Ser.

When a substitution occurs at position 60, the substituting amino acid is Glu.

When a substitution occurs at position 61, the substituting amino acid is Asp, Gln, Glu or Ser.

When a substitution occurs at position 62, the substituting amino acid is Asp, Gln, Glu or Ser.

When a substitution occurs at position 63, the substituting amino acid is Asp or Glu.

When a substitution occurs at position 65, the substituting amino acid is Asn, Asp, Gln, Glu, Pro or Ser.

When a substitution occurs at position 66, the substituting amino acid is Asn, Asp, Gln, Glu, Gly, Pro or Ser.

B. Substitutions in the Second Loon Region

When a substitution occurs in the second loop region, the substitution occurs at one or more of positions 95, 96, 97, 98, 99, 100, 101, 102, 103, 104, 105,106 or 107.

When a substitution occurs at position 95, the substituting amino acid is Ala, Asn, Asp, Cys, Gln, Glu, Gly, His, Met, Pro, Ser or Thr.

When a substitution occurs at position 96, the substituting amino acid is Ala, Asn, Asp, Cys, Gln, Glu, Gly, His, Ile, Met, Pro, Ser, Thr or Val.

When a substitution occurs at position 97, the substituting amino acid is Asn, Asp, Gln, Glu, Pro or Ser.

When a substitution occurs at position 98, the substituting amino acid is Asn, Asp, Gln, Glu, Gly, His, Pro, Ser or Thr.

When a substitution occurs at position 99, the substituting amino acid is Glu.

When a substitution occurs at position 100, the substituting amino acid is Asn, Asp, Gln, Glu, Pro or Ser.

When a substitution occurs at position 101, the substituting amino acid is Asp or Glu.

When a substitution occurs at position 102, the substituting amino acid is Asn, Asp, Gln, Glu, Pro or Ser.

When a substitution occurs at position 103, the substituting amino acid is Asn, Asp, Glu or Ser.

When a substitution occurs at position 104, the substituting amino acid is Ala, Asn, Asp, Cys, Gln, Glu, Gly, His, Ile, Leu, Met, Pro, Ser, Thr or Val.

When a substitution occurs at position 105, the substituting amino acid is Asp or Glu.

When a substitution occurs at position 106, the substituting amino acid is Ala, Asn, Asp, Cys, Gln, Glu, Gly, His, Ile, Leu, Met, Phe, Pro, Ser, Thr, Tyr or Val.

When a substitution occurs at position 107, the substituting amino acid is Ala, Asn, Asp, Cys, Gln, Glu, Gly, His, Leu, Met, Pro, Ser, Thr or Val.

C. Substitutions in the Third Lood Region

When a substitution occurs in the third loop region, the substitution occurs at one or more of positions 126, 127, 128, 129, 130, 131, 132 or 133.

When a substitution occurs at position 126, the substituting amino acid is Ala, Asn, Asp, Cys, Gln, Glu, Gly, His, Ile, Met, Pro, Ser, Thr or Val.

When a substitution occurs at position 127, the substituting amino acid is Asn, Asp, Gln, Glu, Pro or Ser.

When a substitution occurs at position 128, the substituting amino acid is Asn, Asp, Gln, Glu, Gly or Ser.

When a substitution occurs at position 129, the substituting amino acid is Asn, Asp, Gln, Glu, Gly or Ser.

When a substitution occurs at position 130, the substituting amino acid is Asp or Glu.

When a substitution occurs at position 131, the substituting amino acid is Asn, Asp, Gln, Glu, Gly or Ser.

When a substitution occurs at position 132, the substituting amino acid is Asp or Glu.

When a substitution occurs at position 133, the substituting amino acid is Asn, Asp, Gln, Glu, Gly, His, Pro, Ser or Thr.

D. Substitutions in the Fourth Loop Region

When a substitution occurs in the fourth loop region, the substitution occurs at one or more of positions 154, 155, 156, 157, 158, 159, 160, 161, 162, 163, 164, 165, 166 or 167.

When a substitution occurs at position 154, the substituting amino acid is Asn, Asp, Gln, Glu, Pro or Ser.

When a substitution occurs at position 155, the substituting amino acid is Asp, Gln, Glu or Ser.

When a substitution occurs at position 156, the substituting amino acid is Asp.

When a substitution occurs at position 157, the substituting amino acid is Asn, Asp, Gln, Glu, Pro or Ser.

When a substitution occurs at position 158, the substituting amino acid is Asn, Asp, Gln, Glu, Gly, Pro or Ser.

When a substitution occurs at position 159, the substituting amino acid is Asp or Glu.

When a substitution occurs at position 160, the substituting amino acid is Asn, Asp, Gln, Glu, Pro or Ser.

When a substitution occurs at position 161, the substituting amino acid is Asp or Glu.

When a substitution occurs at position 162, the substituting amino acid is Asp or Glu.

When a substitution occurs at position 163, the substituting amino acid is Asp or Glu.

When a substitution occurs at position 164, the substituting amino acid is Asn, Asp, Gln, Glu, Gly, Pro or Ser.

When a substitution occurs at position 165, the substituting amino acid is Ala, Asn, Asp, Cys, Gln, Glu, Gly, His, Met, Pro, Ser or Thr.

When a substitution occurs at position 166, the substituting amino acid is Asn, Asp, Gln, Glu, Pro or Ser.

When a substitution occurs at position 167, the substituting amino acid is Ala, Asn, Asp, Cys, Gln, Glu, Gly, His, Ile, Leu, Met, Pro, Ser, Thr or Val.

E. Substitutions in the Fifth Loop Region

When a substitution occurs in the fifth loop region, the substitution occurs at one or more of positions 187, 188, 189, 190 or 191.

When a substitution occurs at position 187, the substituting amino acid is Asn, Asp, Gln, Glu, Gly, His, Pro, Ser and Thr.

When a substitution occurs at position 188, the substituting amino acid is Asp or Glu.

When a substitution occurs at position 189, the substituting amino acid is Ala, Asn, Asp, Cys, Gln, Glu, Gly, His, Ile, Leu, Met, Pro, Ser, Thr, Tyr or Val.

When a substitution occurs at position 190, the substituting amino acid is Asp or Glu.

When a substitution occurs at position 191, the substituting amino acid is Asp or Glu.

F. Substitutions in the Sixth Loop Region

When a substitution occurs in the sixth loop region, the substitution occurs at one or more of positions 199, 200, 201, 202, 203, 204, 205, 206, 207, 208, 209, 210, 211, 212, 213, 214, 215, 216, 217, 218, 219 or 220 .

When a substitution occurs at position 199, the substituting amino acid for position 199 is Cys, Ala, His, Thr, Pro, Gly, Gln, Asn, Ser, Asp or Glu.

When a substitution occurs at position 200, the substituting amino acid for position 200 is His, Thr, Pro, Gly, Gln, Asn, Ser, Asp or Glu.

When a substitution occurs at position 201, the substituting amino acid for position 201 is Gly, Gln, Asn, Ser, Asp or Glu.

When a substitution occurs at position 202, the substituting amino acid for position 202 is Pro, Gln, Asn, Ser, Asp or Glu.

When a substitution occurs at position 203, the substituting amino acid for position 203 is Met, Cys, Ala, His, Thr, Pro, Gly, Gln, Asn, Ser, Asp or Glu.

When a substitution occurs at position 204, the substituting amino acid for position 204 is Asp, or Glu.

When a substitution occurs at position 205, the substituting amino acid for position 205 is Leu, Val, Met, Cys, Ala, His, Thr, Pro, Gly, Gln, Asn, Ser, Asp or Glu.

When a substitution occurs at position 206, the substituting amino acid for position 206 is Pro, Asn, Ser, Asp, or Glu.

When a substitution occurs at position 207, the substituting amino acid for position 207 is Asp or Glu.

When a substitution occurs at position 208, the substituting amino acid for position 208 is Pro, Gly, Gln, Asn, Ser, Asp or Glu.

When a substitution occurs at position 209, the substituting amino acid for position 209 is Ile, Val, Met, Cys, Ala, His, Thr, Pro, Gly, Gln, Asn, Ser, Asp or Glu.

When a substitution occurs at position 210, the substituting amino acid for position 210 is Ala, Gly, Gln, Asn, Ser, Asp or Glu.

When a substitution occurs at position 211, the substituting amino acid for position 211 is Ala, Pro, Gln, Asn, Ser, Asp or Glu.

When a substitution occurs at position 212, the substituting amino acid for position 212 is Gln, Ser, Asp or Glu.

When a substitution occurs at position 213, the substituting amino acid for position 213 is Trp, Phe, Tyr, Leu, Ile, Val, Met, Cys, Ala, His, Thr, Pro, Gly, Gln, Asn, Ser, Asp or Glu.

When a substitution occurs at position 214, the substituting amino acid for position 214 is Phe, Leu, Ile, Val, Met, Cys, Ala, His, Thr, Pro, Gly, Gln, Asn, Ser, Asp or Glu.

When a substitution occurs at position 215, the substituting amino acid for position 215 is Thr, Pro, Gln, Asn, Ser, Asp or Glu.

When a substitution occurs at position 216, the substituting amino acid for position 216 is His, Thr, Pro, Gly, Gln, Asn, Ser, Asp or Glu.

When a substitution occurs at position 217, the substituting amino acid for position 217 is Leu, Ile, Val, Met, Cys, Ala, His, Thr, Pro, Gly, Gln, Asn, Ser, Asp or Glu.

When a substitution occurs at position 218, the substituting amino acid for position 218 is Gln, Ser, Asp or Glu.

When a substitution occurs at position 219, the substituting amino acid for position 219 is Pro, Gln, Asn, Ser, Asp or Glu.

When a substitution occurs at position 220, the substituting amino acid for position 220 is Pro, Gly, Gln, Asn, Ser Asp or Glu.

G. Preparation of Enzyme Variants

EXAMPLE 1

Mutant BPN' Genes

A phagemid (pSS-5) containing the wild type subtilisin BPN' gene (Mitchinson, C. and J. A. Wells, (1989), "Protein Engineering of Disulfide Bonds in Subtilisin BPN', Biochemistry, Vol. 28, pp. 4807–4815) is transformed into *Escherichia coli* ung-strain CJ236 and a single stranded uracil-containing DNA template is produced using the VCSM13 helper phage (Kunkel, T. A., J. D. Roberts and R. A. Zakour, "Rapid and efficient site-specific mutagenesis without phenotypic selection", Methods in Enzymology, Vol. 154, pp. 367–382, (1987); as modified by Yuckenberg, P. D., F. Witney, J. Geisselsoder and J. McClary, "Site-directed in vitro mutagenesis using uracil-containing DNA and phagemid vectors", Directed Mutagenesis—A Practical Approach, ed. M. J. McPherson, pp. 27–48, (1991); both of which are incorporated herein by reference). A single primer site-directed mutagenesis modification of the method of Zoller and Smith (Zoller, M. J., and M. Smith, "Oligonucleotide-directed mutagenesis using M13-derived vectors: an efficient and general procedure for the production of point mutations in any fragment of DNA", Nucleic Acids Research, Vol. 10, pp. 6487–6500, (1982), incorporated herein by reference) is used to produce all mutants (basically as presented by Yuckenberg, et al., 1991, above). Oligonucleotides are made using an Applied Biosystem Inc. 380B DNA synthesizer. Mutagenesis reaction products are transformed into *Escherichia coli* strain MM294 (American Type Culture Collection *E. Coli.* 33625). All mutants are confirmed by DNA sequencing and the isolated DNA is transformed into the *Bacillus subtilis* expression strain BG2036 (Yang, M. Y., E. Ferrari and D. J. Henner, (1984), "Cloning of the Neutral Protease Gene of *Bacillus subtillis* and the Use of the Cloned Gene to Create an In Vitro-derived Deletion Mutation", Journal of Bacteriology, Vol. 160, pp. 15–21). For some of the mutants a modified pSS-5 with a frameshift-stop codon mutation at amino acid 217 is used to produce the uracil template. Oligonucleotides are designed to restore the proper reading frame at position 217 and also encoded for random substitutions at positions 59, 60, 61, 62, 63, 64, 65, 66; 95, 96, 97, 98, 99, 100, 101, 102, 103, 104, 105, 106, 107; 126, 127, 128, 129, 130, 131, 132, 133; 154, 155, 156, 157, 158, 159, 160, 161, 162, 163, 164, 165, 166, 167; 187, 188, 189, 190, 191; 199, 200, 201, 202, 203, 204, 205, 206, 207, 208, 209, 210, 211, 212, 213, 214, 215, 216, 217, 218, 219 and 220 (equimolar and/or variable mixtures of all four nucleotides for all three bases at these codons). Mutations that correct for the frameshift-stop and produce a functional enzyme are identified by their ability to digest casein. The random substitutions are determined by DNA sequencing.

EXAMPLE 2

Fermentation

The *Bacillus subtilis* cells (BE2036) containing a subtilisin mutant of interest are grown to mid-log phase in a one liter culture of LB-glucose broth and inoculated into a Biostat ED fermenter (B. Braun Biotech, Inc., Allentown, Pa.) in a total volume of 10 liters. The fermentation media contains Yeast Extract, starch, antifoam, buffers and trace minerals (see Fermentation: A Practical Approach, Ed. B. McNeil and L. M. Harvey, 1990). The broth is kept at a constant pH of 7.0 during the fermentation run. Chloramphenical is added for antibiotic selection of mutagenized plasmid. The cells are grown overnight at 37° C. to an $A_{600}$ of about 60 and harvested.

EXAMPLE 3

Purification

The fermentation broth is taken through the following steps to obtain pure enzyme. The broth is cleared of *Bacillus subtilis* cells by centrifugation, and clarified by removing fine particulates with a 100K cutoff membrane. This is followed by concentration on a 10K cutoff membrane, and flow dialysis to reduce the ionic strength and adjust the pH to 5.5 using 0.025M MES buffer (2 -(N-morpholino) ethanesulfonic acid). The enzyme is further purified by loading it onto either a cation exchange chromatography column or an affinity adsorption chromatography column and eluting it from the column with a NaCl or a propylene glycol gradient (see Scopes, R. K. Protein Purification Principles and Practice, Springer-Verlag, New York (1984), incorporated herein by reference).

The pNA assay (DelMar, E. G., C. Largman, J. W. Brodrick and M. C. Geokas, Anal. Biochem., Vol. 99, pp. 316–320, (1979), incorporated herein by reference) is used to determine the active enzyme concentration for fractions collected during gradient elution. This assay measures the rate at which p-nitroaniline is released as the enzyme hydrolyzes the soluble synthetic substrate, succinyl-alanine-alanine-proline-phenylalanine-p-nitroanilide (sMPF-pNA). The rate of production of yellow color from the hydrolysis reaction is measured at 410 nm on a spectrophotometer and is proportional to the active enzyme concentration. In addition, absorbance measurements at 280 nm are used to determine the total protein concentration. The active enzyme/total-protein ratio gives the enzyme purity, and is used to identify fractions to be pooled for the stock solution.

To avoid autolysis of the enzyme during storage, an equal weight of propylene glycol is added to the pooled fractions obtained from the chromatography column. Upon completion of the purification procedure the purity of the stock enzyme solution is checked with SDS-PAGE (sodium dodecyl sulfate polyacrylamide gel electrophoresis) and the absolute enzyme concentration is determined via an active site titration method using trypsin inhibitor type II-T: turkey egg white purchased from Sigma Chemical Company (St. Louis, Mo.). The measured conversion factors will show which changes made in the enzyme molecule at the various positions result in the enzyme variant having increased activity over the wild-type, against the soluble substrate pNA.

In preparation for use, the enzyme stock solution is eluted through a Sephadex-G25 (Pharmacia, Piscataway, N.J.) size exclusion column to remove the propylene glycol and exchange the buffer. The MES buffer in the enzyme stock solution is exchanged for 0.1 M Tris buffer (Tris (hydroxymethyl-aminomethane) containing 0.01M $CaCl_2$ and pH adjusted to 8.6 with HCl. All experiments are carried out at pH 8.6 in Tris buffer thermostated at 25° C.

H. Characterization of Enzyme Variants

EXAMPLE 4

Model Surface Preparation

Aminopropyl controlled pore glass (CPG) purchased from CPG Inc. (Fairfield, N.J.) is used as a support for covalently attaching the sAAPF-pNA substrate purchased from Bachem, Inc. (Torrence, Calif.). The reaction is carried out in dimethyl sulfoxide and (1-ethyl-3[3-(dimethylamino) propyl] carbodiimide hydrochloride) (EDC) is used as a coupling agent. Upon completion (monitored by pNA assay), the excess solvent is removed, and the CPG:sAPF-pNA is rinsed with dimethyl sulfoxide (DMSO) and doubly-distilled water. This is followed by oven drying with a $N_2$ purge at about 70° C. The reaction scheme and preparation of the immobilized substrate are conducted as described by Brode, P. F. III, and D. S. Rauch, "Subtilisin BPN': Activity on an Immobilized Substrate," Langmuir, Vol. 8, p. 1325–1329, (1992), incorporated herein by reference.

The CPG surface will have 62,000±7,000 pNA molecules/$\mu m^2$. The surface area will remain unchanged from the value of 50.0 $m^2$/g reported by CPG Inc. for the CPG as received. This suggests that the procedure used to add sAAPF-pNA to CPG does not damage the porous structure (mean diameter is 486 Å).

EXAMPLE 5

Surface Hydrolysis Assay

Using CPG:sAAPF-pNA, adsorption of an enzyme variant and hydrolysis of a CPG-bound peptide can be measured in a single experiment. A small volume of enzyme variant stock solution is added to a flask containing Tris buffer and CPG:sAAPF-pNA which has been degassed. The flask is shaken on a wrist-action shaker for a period of 90 minutes during which the shaker is stopped at various time intervals (for example, every 2 minutes during the early stages of adsorption hydrolysis—e.g., the first 20 minutes—and every 10 minutes towards the end of the experiment). The CPG:sAAPF-pNA is allowed to settle and the solution is sampled. Both the experimental procedure and the calculation of the adsorption and hydrolysis are conducted as described by Brode et at, 1992, above.

All enzymes are monitored for stability against autolysis and should show no appreciable autolytic loss over the time course of this experiment. Therefore, enzyme adsorption can be determined by measuring solution depletion. The difference between the initial enzyme variant concentration and the concentration measured at each individual time point gives the amount of enzyme variant adsorbed. The amount of pNA hydrolyzed from the surface is measured by taking an absorbance reading on an aliquot of the sample at 410 nm. The total amount of pNA hydrolyzed is calculated by adding the amount sampled and the amount remaining in the flask. This value is corrected by subtracting the amount of pNA that is hydrolyzed by Tris buffer at pH 8.6 when no enzyme is present. This base-hydrolysis ranges from 7–29% of the total hydrolysis depending on the efficiency of the enzyme.

EXAMPLE 6

Soluble Substrate Kinetic Analysis

The rates of hydrolysis of the soluble substrate sAAPF-pNA are monitored by measuring the adsorbance increase as a function of time at 410 nm on a DU-70 spectrophotometer. The enzyme concentration is held constant and is prepared to be in the range of 6–10 nanomolar while the substrate concentration is varied from 90–700 $\mu M$ sAAPF-pNA for each kinetic determination. An adsorbance data point is taken each second over a period of 900 seconds and the data are transferred to a LOTUS™ spreadsheet (Lotus Development Corporation, Cambridge, Mass.). Analysis for kinetic parameters is conducted by the standard Lineweaver Burk analysis in which the data in the initial part of the run (generally the first minute) are fit to a linear regression curve to give $v_O$. The $v_O$ and $s_O$ data are plotted in the standard inverse fashion to give $K_M$ and $k_{cat}$.

I. Example BPN' Variants

BPN' variants of the present invention which have decreased adsorption to and increased hydrolysis of surface bound substrates are exemplified in Tables 2–25, below. In describing the specific mutations, the original amino acid occurring in wild-type is given first, the position number second, and the substituted amino acid third.

TABLE 2

Loop 1 - Single Mutation Variants

| |
| --- |
| Gln59Asn |
| Gln59Asp |
| Gln59Glu |
| Gln59Ser |
| Asp60Glu |
| Asn61Asp |
| Asn61Gln |
| Asn61Glu |
| Asn61Ser |
| Asn62Asp |
| Asn62Gln |
| Asn62Glu |
| Asn62Ser |
| Ser63Asp |
| Ser63Glu |
| Gly65Asn |
| Gly65Asp |
| Gly65Gln |
| Gly65Glu |
| Gly65Pro |
| Gly65Ser |
| Thr66Asn |
| Thr66Asp |
| Thr66Gln |
| Thr66Glu |
| Thr66Gly |
| Thr66Pro |
| Thr66Ser |

TABLE 3

Loop 1 - Double Mutation Variants

| |
| --- |
| Gln59Ser + Asn62Glu |
| Asp60Glu + Asn61Ser |
| Asn61Glu + Asn62Ser |
| Gln59Ser + Gly65Gln |
| Asn61Gln + Gly65Asn |
| Asn61Ser + Asn62Asp |
| Gln59Glu + Asn61Gln |
| Asp60Glu + Gly65Gln |
| Gln59Asp + Gly65Pro |

TABLE 3-continued

Loop 1 - Double Mutation Variants

Asn61Asp + Gly65Asn
Gln59Ser + Asn62Asp
Gln59Asn + Gly65Gln
Asn62Asp + Thr66Gly
Gln59Asn + Asn62Glu
Asn61Ser + Ser63Glu
Gln59Ser + Asp60Glu
Asp60Glu + Thr66Gln
Asn61Glu + Thr66Gly
Asp60Glu + Asn62Gln
Asn62Gln + Gly65Pro
Asn61Ser + Thr66Ser
Asp60Glu + Gly65Pro
Ser63Glu + Gly65Pro
Asp60Glu + Thr66Ser
Gln59Ser + Asn61Glu
Asn62Asp + Gly65Gln
Asn61Gln + Ser63Asp
Gln59Asp + Gly65Asn
Ser63Asp + Thr66Pro
Ser63Glu + Thr66Asn
Asn62Glu + Thr66Asn
Asn61Asp + Gly65Ser
Gly65Pro + Thr66Ser
Gln59Ser + Asn62Ser
Asp60Glu + GlyG5Ser
Ser63Asp + Gly65Ser
Asn61Gln + Ser63Glu
Asn61Asp + Asn62Ser
Gln59Glu + Gly65Pro
Gln59Ser + Asn61Asp
Gln59Asp + Asn62Ser
Gln59Asn + Gly65Ser
Ser63Glu + Thr66Ser
Asn61Ser + Ser63Asp
Asn62Ser + Gly65Pro

TABLE 4

Loop 1 - Triple Mutation Variants

Gln59Ser + Ser63Asp + Gly65Pro
Asn62Gln + Gly65Ser + Thr66Asp
Gln59Ser + Asp60Glu + Thr66Gln
Gln59Asn + Ser63Glu + Thr66Pro
Asn61Ser + Gly65Asn + Thr66Glu
Ser63Glu + Gly65Ser + Thr66Asn
Asn62Asp + Gly65Ser + Thr66Gly
Gln59Ser + Asn62Asp + Thr66Pro
Gln59Ser + Asp60Glu + Asn61Gln
Asn61Gln + Ser63Asp + Gly65Ser
Asn62Glu + Gly65Asn + Thr66Gln
Asp60Glu + Gly65Asn + Thr66Ser
Asn62Ser + Ser63Asp + Thr66Gln
Gln59Asp + Asn62Gln + Gly65Pro
Asn62Ser + Ser63Glu + Thr66Gly
Asn61Asp + Asn62Ser + Gly65Asn
Asp60Glu + Asn61Gln + Asn62Ser
Asp60Glu + Asn61Gln + Gly65Ser
Asp60Glu + Gly65Pro + Thr66Asn
Gln59Ser + Asn61Glu + Asn62Asp
Asn61Asp + Asn62Asp + Gly65Pro
Asn61Glu + Asn62Glu + Thr66Gln
Gln59Asp + Asp60Glu + Thr66Gln
Gln59Asp + Asp60Glu + Thr66Pro
Asn62Asp + Ser63Asp + Gly65Asn
Asn62Glu + Ser63Glu + Gly65Asn
Asn62Asp + Ser63Glu + Gly65Gln
Gln59Ser + Asn62Asp + Ser63Glu
Asn62Glu + Ser63Asp + Gly65Ser
Asn61Asp + Asn62Asp + Ser63Glu
Gln59Glu + Asp60Glu + Asn61Glu
Asp60Glu + Asn62Glu + Ser63Asp
Asp60Glu + Asn61Glu + Ser63Glu

TABLE 4-continued

Loop 1 - Triple Mutation Variants

Gln59Ser + Asp60Glu + Asn62Glu

TABLE 5

Loop 1 - Quadruple Mutation Variants

Gln59Ser + Asp60Glu + Gly65Gln + Thr66Gln
Gln59Ser + Asn62Ser + Ser63Asp + Gly65Gln
Asp60Glu + Asn62Ser + Gly65Pro + Thr66Gln
Asn62Gln + Ser63Glu + Gly65Pro + Thr66Gln
Asn61Gln + Asn62Gln + Ser63Asp + Gly65Pro
Gln59Asn + Asp60Glu + Asn61Gln + Gly65Asn
Gln59Glu + Asn62Ser + Gly65Pro + Thr66Ser
Gln59Asn + Asn61Asp + Asn62Asp + Thr66Asn
Gln59Asp + Asp60Glu + Asn62Ser + Gly65Ser
Asn61Gln + Asn62Asp + Ser63Glu + Thr66Gln
Asp60Glu + Asn61Asp + Asn62Glu + Gly65Ser
Asn61Asp + Asn62Glu + Gly65Pro + Thr66Ser
Asn61Asp + Asn62Glu + Ser63Asp + Gly65Ser
Gln59Glu + Asp60Glu + Asn61Asp + Gly65Ser
Asp60Glu + Asn62Asp + Ser63Glu + Thr66Pro
Asp60Glu + Asn62Glu + Ser63Glu + Thr66Asn
Asp60Glu + Asn62Glu + Ser63Asp + Gly65Ser
Asp60Glu + Asn61Asp + Ser63Glu + Thr66Asn
Gln59Ser + Asp60Glu + Asn61Asp + Ser63Asp
Asp60Glu + Asn62Asp + Ser63Asp + Gly65Pro
Asp60Glu + Asn61Asp + Ser63Asp + Thr66Gly
Asp60Glu + Asn61Asp + Ser63Glu + Gly65Asn
Gln59Ser + Asp60Glu + Asn62Asp + Thr66Gly
Asp60Glu + Asn62Asp + Gly65Ser + Thr66Pro
Asp60Glu + Asn61Gln + Asn62Glu + Gly65Ser
Gln59Ser + Asp60Glu + Asn62Asp + Gly65Gln
Asp60Glu + Asn61Ser + Asn62Gln + Ser63Glu
Asp60Glu + Asn61Ser + Ser63Asp + Thr66Pro
Gln59Ser + Asp60Glu + Asn61Gln + Ser63Glu
Asp60Glu + Ser63Glu + Gly65Ser + Thr66Asn
Gln59Asn + Asp60Glu + Ser63Asp + Gly65Gln
Asp60Glu + Ser63Glu + Gly65Pro + Thr66Ser

TABLE 6

Loop 2 - Single Mutation Variants

Val95Ala
Val95Asn
Val95Asp
Val95Cys
Val95Gln
Val95Glu
Val95Gly
Val95His
Val95Met
Val95Pro
Val95Ser
Val95Thr
Leu96Ala
Leu96Asn
Leu96Asp
Leu96Cys
Leu96Gln
Leu96Glu
Leu96Gly
Leu96His
Leu96Ile
Leu96Met
Leu96Pro
Leu96Ser
Leu96Thr
Leu96Val
Gly97Asn
Gly97Asp
Gly97Gln

TABLE 6-continued

Loop 2 - Single Mutation Variants

Gly97Glu
Gly97Pro
Gly97Ser
Ala98Asn
Ala98Asp
Ala98Gln
Ala98Glu
Ala98Gly
Ala98His
Ala98Pro
Ala98Ser
Ala98Thr
Asp99Glu
Gly100Asn
Gly100Asp
Gly100Gln
Gly100Glu
Gly100Pro
Gly100Ser
Ser101Asp
Ser101Glu
Gly102Asn
Gly102Asp
Gly102Gln
Gly102Glu
Gly102Pro
Gly102Ser
Gln103Asn
Gln103Asp
Gln103Glu
Gln103Ser
Tyr104Ala
Tyr104Asn
Tyr104Asp
Tyr104Cys
Tyr104Gln
Tyr104Glu
Tyr104Gly
Tyr104His
Tyr104Ile
Tyr104Leu
Tyr104Met
Tyr104Pro
Tyr104Ser
Tyr104Thr
Tyr104Val
Ser105Asp
Ser105Glu
Trp106Ala
Trp106Asn
Trp106Asp
Trp106Cys
Trp106Gln
Trp106Glu
Trp106Gly
Trp106His
Trp106Ile
Trp106Leu
Trp106Met
Trp106Phe
Trp106Pro
Trp106Ser
Trp106Thr
Trp106Tyr
Trp106Val
Ile107Ala
Ile107Asn
Ile107Asp
Ile107Cys
Ile107Gln
Ile107Glu
Ile107Gly
Ile107His
Ile107Leu
Ile107Met
Ile107Pro
Ile107Ser

TABLE 6-continued

Loop 2 - Single Mutation Variants

Ile107Thr
Ile107Val

TABLE 7

Loop 2 - Double Mutation Variants

Val 95Gln + Ser101Glu
Gly 97Ser + Gly100Gln
Ser105Glu + Trp106Gly
Asp 99Glu + Gln103Asn
Ala 98Gln + Trp106Thr
Gly 97Asp + Ile107Thr
Gly100Ser + Gly102Gln
Leu 96Ser + Ser101Glu
Asp 99Glu + Ile107Ala
Leu 96Asn + Asp 99Glu
Gly102Gln + Trp106Asp
Tyr104Leu + Trp106Glu
Tyr104Pro + Ile107Asp
Gly 97Ser + Ser101Asp
Gly100Pro + Ser101Glu
Val 95Asn + Ala 98Asp
Val 95Met + Ile107Gly
Asp 99Glu + Trp106Cys
Gly100Asn + Trp106Thr
Gln103Ser + Trp106Pro
Gly102Asp + Gln103Ser
Gly102Ser + Trp106Gln
Ser101Asp + Gly102Pro
Leu 96Cys + Trp106Asp
Asp 99Glu + Gly102Ser
Gly102Asp + Trp106Val
Gly 97Ser + Trp106Phe
Gln103Asp + Tyr104Thr
Ala 98His + Gly100Gln
Ser105Glu + Trp106Leu
Leu 96His + Tyr104Thr
Gly 97Pro + Ser101Glu
Val 95Thr + Trp106Ile
Gly100Asp + Tyr104Ile
Val 95Pro + Gln103Asn
Gln103Asn + Trp106Ile
Ala 98His + Gly102Pro
Trp106Asn + Ile107His
Val 95Gln + Leu 96Asp
Gly 97Asp + Ala 98Gln
Gly100Ser + Ser101Glu
Val 95Asp + Tyr104Gly
Tyr104Ala + Ser105Asp
Gly100Pro + Ser105Glu
Leu 96Cys + Tyr104Leu
Val 95Gly + Gly100Ser
Gly102Gln + Tyr104Ser
Ala 98Gly + Trp106Phe
Gly100Asp + Trp106Phe
Val 95Glu + Ala 98Gln
Ser101Glu + Tyr104Asn
Leu 96Val + Ser101Asp
Gly102Glu + Gln103Asn
Gly102Glu + Trp106Gly
Ala 98Gln + Gly100Asp
Gly100Gln + Gln103Ser
Gly 97Glu + Tyr104Leu
Ser101Asp + Gly102Ser
Ala 98His + Ser101Asp
Gly 97Asp + Gln103Asn

TABLE 8

Loop 2 - Triple Mutation Variants

Val 95Gln + Leu 96Thr + Ser101Glu
Ala 98His + Gln103Glu + Trp106Cys
Ala 98Gln + Ser101Glu + Tyr104Met
Ser101Asp + Gln103Ser + Ile107Cys
Ala 98Pro + Asp 99Glu + Gly102Pro
Val 95Pro + Gly 97Glu + Gly100Gln
Ser101Glu + Gly102Pro + Ile107His
Leu 96Pro + Gly100Pro + Gly102Asn
Gly100Glu + Gly102Asn + Trp106Tyr
Ala 98Asn + Gln103Glu + Ile107Ser
Gly 97Pro + Gly100Asp + Trp106Met
Gln103Asn + Tyr104Leu + Ser105Asp
Gly 97Pro + Ala 98Gln + Tyr104Cys
Ala 98Gly + Gly100Glu + Gln103Ser
Leu 96Ile + Gly 97Pro + Ser105Asp
Ala 98Pro + Gly100Pro + Ile107Ala
Val 95Pro + Gln103Asp + Trp106Met
Val 95Gln + Ser101Glu + Trp106Phe
Leu 96Val + Ser101Glu + Ile107Pro
Leu 96Gly + Gly 97Glu + Trp106Thr
Gly 97Asp + Tyr104Ser + Trp106His
Gly 97Ser + Gly100Pro + Tyr104Cys
Gln103Ser + Ser105Asp + Ile107His
Ala 98Glu + Tyr104Cys + Trp106Phe
Val 95Gln + Gly100Pro + Gly102Ser
Val 95Ala + Gly102Asp + Tyr104Ser
Val 95Ala + Leu 96Met + Ser105Asp
Gly102Gln + Trp106Leu + Ile107Gly
Leu 96Asn + Gly 97Glu + Ile107Pro
Gly100Pro + Gly102Gln + Gln103Glu
Gly 97Asp + Ala 98Asn + Trp106Leu
Ala 98Gln + Gly100Pro + Trp106His
Leu 96Thr + Gly100Asn + Ser105Glu
Val 95Ser + Leu 96Asn + Gly 97Pro
Gly100Gln + Ser105Glu + Trp106Gln
Gly 97Glu + Tyr104Thr + Trp106Val
Leu 96Ala + Ala 98Gln + Gly100Glu
Val 95His + Gly 97Gln + Ser101Glu
Val 95Pro + Gly102Asn + Gln103Glu
Gln103Asn + Trp106Ile + Ile107Ala
Gly 97Ser + Ala 98Glu + Tyr104Gln
Val 95Glu + Leu 96Ile + Ile107Gln
Leu 96Gln + Ala 98Ser + Asp 99Glu
Leu 96Pro + Ser101Glu + Gly102Pro
Gly 97Asn + Ala 98Pro + Gly100Pro
Gly 97Asn + Ala 98Glu + Gly100Asn
Gly102Pro + Trp106Ala + Ile107Pro
Gly100Ser + Gly102Glu + Trp106Cys
Leu 96Thr + Gly102Glu + Ile107Val
Leu 96Cys + Trp106Leu + Ile107Pro
Leu 96Thr + Ser105Glu + Trp106Tyr
Leu 96Ala + Gly100Asp + Ser101Asp
Gly 97Asn + Ser101Glu + Gly102Asp
Val 95Gln + Ser101Asp + Gly102Asp
Asp 99Glu + Gly100Asp + Trp106Phe
Tyr104Glu + Ser105Asp + Ile107Asp
Leu 96Glu + Ser101Glu + Trp106Val
Tyr104Met + Ser105Asp + Ile107Asp
Gly 97Asp + Gly100Asp + Trp106Pro
Val 95Ala + Gly 97Asp + Asp 99Glu

TABLE 9

Loop 2 - Quadruple Mutation Variants

Leu 96Gln + Gly 97Ser + Ser101Glu + Trp106Val
Val 95Ala + Ala 98Gln + Gly100Asn + Gln103Asp
Val 95Gln + Tyr104Ile + Trp106Gly + Ile107Pro
Val 95Met + Leu 96Gly + Gly100Pro + Trp106Gly
Ala 98Gln + Gly100Pro + Tyr104Thr + Trp106His
Gly 97Pro + Ala 98His + Gly100Pro + Ile107Asp
Ala 98Pro + Gly100Glu + Trp106Ser + Ile107Met
Leu 96Gln + Gly 97Ser + Ser105Asp + Ile107Val
Ala 98Gly + Ser101Asp + Trp106Ala + Ile107Gln

TABLE 9-continued

Loop 2 - Quadruple Mutation Variants

Val 95Ser + Gly 97Ser + Asp 99Glu + Gln103Ser
Leu 96Thr + Gly 97Ser + Asp 99Glu + Tyr104Asn
Val 95Thr + Leu 96Gln + Ala 98Pro + Ser105Glu
Val 95Gly + Gly 97Ser + Tyr104Asn + Trp106Glu
Leu 96Gln + Gly 97Ser + Tyr104Thr + Ile107Pro
Val 95Ser + Leu 96Pro + Gly100Gln + Ser101Asp
Leu 96Met + Gly100Ser + Ser101Asp + Trp106Asn
Leu 96Ile + Ala 98Ser + Gly100Pro + Gly102Glu
Val 95Asn + Ala 98Gly + Gln103Ser + Tyr104Val
Gly 97Asn + Asp 99Glu + Gly102Asn + Trp106His
Gly 97Ser + Gly102Asp + Gln103Asp + Ile107His
Val 95Pro + Gly100Glu + Ser101Glu + Tyr104Gly
Ala 98Pro + Gly100Asp + Ser101Asp + Ile107Cys
Leu 96Gly + Ser101Asp + Gly102Asp + Ile107Gly
Val 95His + Tyr104Asp + Ser105Asp + Trp106Ala
Gly102Pro + Ser105Asp + Trp106Asp + Ile107Thr
Leu 96Glu + Ala 98Gln + Gly102Asp + Tyr104Pro
Ala 98Thr + Asp 99Glu + Gly100Glu + Ser101Glu
Gly 97Ser + Ala 98Glu + Asp 99Glu + Gly100Glu
Leu 96Asp + Gly 97Glu + Gly100Glu + Ile107Asn
Leu 96Asn + Gly100Asp + Ser101Asp + Gly102Glu
Val 95Gly + Ser101Glu + Gly102Asp + Gln103Asp
Val 95His + Leu 96Glu + Gly100Gln + Ser101Glu
Leu 96Glu + Gly100Gln + Ser101Asp + Gly102Ser
Gly 97Asp + Gly100Asp + Gly102Pro + Ile107Gly
Gly 97Glu + Asp 99Glu + Gly100Pro + Tyr104Ser
Leu 96Ile + Gly 97Gln + Gln103Glu + Ser105Glu
Gln103Asp + Ser105Asp + Trp106Asn + Ile107His
Val 95Pro + Ala 98Pro + Gln103Glu + Ser105Asp
Val 95His + Asp 99Glu + Ser101Glu + Gly102Pro
Leu 96Asn + Asp 99Glu + Gly100Asn + Ser101Glu
Ala 98Asp + Asp 99Glu + Ser101Asp + Ile107Pro
Leu 96Thr + Gly 97Glu + Gly100Glu + Gly102Asp
Val 95Glu + Gly102Asp + Tyr104Ser + Ile107Ser
Leu 96Gly + Gly102Asp + Gln103Asp + Ser105Glu
Gly102Glu + Gln103Glu + Ser105Glu + Trp106Cys
Asp 99Glu + Ser101Glu + Gly102Glu + Gln103Asn
Asp 99Glu + Ser101Glu + Gly102Glu + Trp106Gly
Gly102Glu + Gln103Asn + Tyr104Asp + Ile107Thr
Val 95His + Leu 96Val + Gln103Glu + Ile107Glu
Gly 97Ser + Gly102Ser + Gln103Glu + Ile107Glu
Val 95Glu + Leu 96Asp + Gln103Asp + Ile107Asn
Val 95Thr + Gly102Glu + Trp106Tyr + Ile107Asp
Val 95Glu + Gly 97Glu + Ala 98Gly + Gly100Asp
Leu 96Ala + Gly 97Pro + Ala 98Asp + Ser101Asp
Val 95Asp + Leu 96Asp + Tyr104Glu + Ile107Ser
Val 95Pro + Gly102Glu + Tyr104Pro + Ser105Asp
Leu 96Asn + Gly102Asp + Gln103Asn + Ser105Glu
Leu 96Asn + Gly102Asp + Tyr104Ala + Ser105Glu
Leu 96Ser + Gly 97Gln + Gly102Glu + Ser105Asp
Leu 96Thr + Asp 99Glu + Gly102Asp + Ile107Gly

TABLE 10

Loop 3 - Single Mutation Variants

Leu126Ala
Leu126Asn
Leu126Asp
Leu126Cys
Leu126Gln
Leu126Glu
Leu126Gly
Leu126His
Leu126Ile
Leu126Met
Leu126Pro
Leu126Ser
Leu126Thr
Leu126Val
Gly127Asn
Gly127Asp
Gly127Gln
Gly127Glu

TABLE 10-continued

| Loop 3 - Single Mutation Variants |
|---|
| Gly127Pro |
| Gly127Ser |
| Gly128Asn |
| Gly128Asp |
| Gly128Gln |
| Gly128Glu |
| Gly128Pro |
| Gly128Ser |
| Pro129Asn |
| Pro129Asp |
| Pro129Gln |
| Pro129Glu |
| Pro129Gly |
| Pro129Ser |
| Ser130Asp |
| Ser130Glu |
| Gly131Asn |
| Gly131Asp |
| Gly131Gln |
| Gly131Glu |
| Gly131Pro |
| Gly131Ser |
| Ser132Asp |
| Ser132Glu |
| Ala133Asn |
| Ala133Asp |
| Ala133Gln |
| Ala133Glu |
| Ala133Gly |
| Ala133His |
| Ala133Pro |
| Ala133Ser |
| Ala133Thr |

TABLE 11

| Loop 3 - Double Mutation Variants |
|---|
| Leu126Gln + Ser130Glu |
| Gly131Gln + Ala133Asn |
| Pro129Asp + Gly131Gln |
| Gly128Ser + Ser130Glu |
| Leu126Pro + Ala133Gly |
| Gly127Asp + Ala133Gly |
| Leu126Asp + Pro129Gln |
| Gly131Asn + Ala133Gln |
| Gly127Pro + Gly131Glu |
| Gly128Asn + Gly131Asp |
| Pro129Gln + Ser130Glu |
| Gly128Pro + Ser130Asp |
| Gly128Gln + Pro129Ser |
| Gly128Asn + Pro129Gly |
| Leu126Val + Ser130Asp |
| Leu126Val + Pro129Ser |
| Leu126Cys + Pro129Glu |
| Gly127Asp + Ala133Thr |
| Gly128Pro + Pro129Glu |
| Gly127Ser + Gly131Asp |
| Leu126His + Pro129Asp |
| Gly131Pro + Ala133Glu |
| Gly127Ser + Gly128Ser |
| Pro129Asn + Gly131Glu |
| Leu126Val + Pro129Asp |
| Pro129Gly + Ala133Asp |
| Leu126Val + Ser130Glu |
| Pro129Glu + Ala133Pro |
| Pro129Gly + Ser130Asp |
| Leu126His + Gly128Glu |
| Gly128Asn + Ser132Glu |
| Gly127Pro + Ser132Asp |
| Gly127Gln + Pro129Gln |
| Gly128Pro + Pro129Asp |
| Gly128ASn + Ser130Glu |
| Leu126Cys + Pro129Asn |

TABLE 11-continued

| Loop 3 - Double Mutation Variants |
|---|
| Pro129Asn + Ser132Glu |
| Leu126Ser + Ser132Asp |
| Gly128Glu + Gly131Ser |
| Pro129Asn + Ser130Asp |
| Leu126Ser + Ser132Glu |
| Pro129Gln + Gly131Pro |
| Gly127Asp + Gly128Gln |
| Gly128Gln + Pro129Glu |
| Gly127Pro + Pro129Gly |
| Pro129Gln + Ala133Gln |
| Leu126Val + Gly128Asp |
| Gly128Ser + Ser132Glu |
| Leu126Asn + Pro129Gly |
| Leu126Ile + Ala133Gly |
| Gly128Ser + Gly131Gln |
| Gly127Ser + Ser130Asp |
| Leu126Cys + Ser132Asp |
| Gly127Pro + Ser130Glu |
| Leu126His + Ala133Asp |
| Gly131Ser + Ala133Glu |
| Gly131Pro + Ala133Gln |
| Gly131Asp + Ala133Ser |
| Leu126Asp + Ala133Asn |
| Leu126Glu + Pro129Gln |

TABLE 12

| Loop 3 - Triple Mutation Variants |
|---|
| Leu126His + Pro129Glu + Ala133Asn |
| Leu126Asp + Gly128Ser + Gly131Gln |
| Pro129Asn + Gly131Ser + Ser132Glu |
| Gly128Pro + Pro129Asn + Ser130Glu |
| Gly128Gln + Ser130Glu + Ala133Ser |
| Gly131Gln + Ser132Glu + Ala133Gln |
| Gly128Asp + Gly131Ser + Ala133Asn |
| Gly131Ser + Ser132Asp + Ala133Pro |
| Pro129Ser + Gly131Gln + Ala133Glu |
| Gly128Asn + Ser130Glu + Gly131Gln |
| Leu126Gly + Gly127Gln + Gly131Pro |
| Leu126Pro + Gly127Glu + Gly128Pro |
| Leu126Ser + Pro129Ser + Ser132Asp |
| Gly128Ser + Ser132Glu + Ala133Asn |
| Leu126Val + Ser132Glu + Ala133Gln |
| Pro129Gly + Ser130Glu + Gly131Pro |
| Leu126Thr + Gly127Pro + Ala133Asn |
| Leu126His + Ser130Asp + Ala133Pro |
| Leu126Cys + Gly127Ser + Pro129Ser |
| Leu126Gly + Ser132Asp + Ala133Ser |
| Gly128Gln + Pro129Gln + Gly131Asn |
| Gly128Asp + Gly131Asn + Ala133His |
| Leu126Cys + Ser130Glu + Ala133Gly |
| Gly127Ser + Ser130Asp + Ala133Gly |
| Leu126His + Pro129Asn + Ser130Asp |
| Leu126Asn + Gly131Asp + Ala133Gln |
| Leu126Met + Gly128Asn + Ser132Asp |
| Leu126Glu + Gly127Gln + Ala133His |
| Leu126Met + Ser132Asp + Ala133His |
| Ser130Glu + Gly131Gln + Ala133Gln |
| Gly127Pro + Gly128Ser + Ala133Ser |
| Leu126Ala + Pro129Gly + Ser132Glu |
| Gly131Asn + Ser132Asp + Ala133Asn |
| Leu126Val + Gly131Asp + Ala133Ser |
| Leu126Ser + Gly127Asn + Ala133Gln |
| Pro129Gln + Ser130Glu + Ala133His |
| Leu126Met + Gly127Ser + Ser130Asp |
| Leu126Cys + Pro129Asn + Gly131Asp |
| Pro129Ser + Ser130Asp + Ala133Asn |
| Leu126Ser + Pro129Gly + Ser132Glu |
| Gly127Ser + Pro129Gln + Ser132Asp |
| Gly127Pro + Gly128Asn + Pro129Gln |
| Leu126His + Ser132Asp + Ala133Asn |
| Gly128Pro + Pro129Glu + Ala133Thr |
| Pro129Ser + Gly131Glu + Ala133Pro |

TABLE 12-continued

Loop 3 - Triple Mutation Variants

Leu126His + Gly128Pro + Pro129Gln
Leu126Met + Gly127Asp + Gly128Asp
Gly128Pro + Gly131Glu + Ser132Asp
Gly131Asp + Ser132Glu + Ala133Pro
Gly128Glu + Pro129Glu + Ala133Asn
Pro129Ser + Ser132Glu + Ala133Glu
Leu126Asn + Ser130Glu + Gly131Asp
Pro129Asn + Ser130Glu + Gly131Asp
Leu126His + Ser130Glu + Gly131Glu
Pro129Glu + Ser130Asp + Gly131Asn
Gly127Ser + Pro129Asp + Ser130Asp
Ser130Asp + Gly131Asp + Ser132Asp
Gly128Asp + Ser130Glu + Gly131Asn
Leu126Met + Gly128Glu + Ser130Asp
Gly128Asp + Pro129Asn + Ser130Glu

TABLE 13

Loop 3 - Quadruple Mutation Variants

Leu126Ser + Pro129Asn + Ser130Asp + Ala133His
Leu126Met + Pro129Ser + Ser132Glu + Ala133Asn
Gly127Ser + Gly131Gln + Ser132Glu + Ala133Gln
Leu126Asn + Gly127Pro + Gly128Glu + Pro129Gly
Leu126Asn + Pro129Gly + Gly131Asp + Ala133Gly
Leu126Gly + Pro129Gly + Ser132Glu + Ala133Pro
Leu126Gly + Gly127Asp + Pro129Gly + Gly131Pro
Gly127Asn + Pro129Gln + Gly131Asp + Ala133Gly
Leu126Pro + Gly127Ser + Gly128Gln + Ser130Glu
Leu126Ala + Gly127Gln + Pro129Asn + Ser130Glu
Leu126Asn + Gly127Ser + Ser130Glu + Ala133Thr
Gly128Gln + Pro129Gln + Ser130Asp + Gly131Ser
Leu126His + Gly128Ser + Gly131Ser + Ser132Asp
Leu126Gln + Pro129Ser + Ser130Asp + Ala133His
Leu126Val + Gly128Pro + Pro129Asn + Ala133Asp
Leu126Val + Pro129Gly + Ser130Glu + Ala133Thr
Leu126Thr + Gly127Pro + Ser132Glu + Ala133Thr
Gly128Asp + Pro129Gly + Gly131Pro + Ala133Ser
Leu126Asn + Gly128Glu + Pro129Gln + Gly131Pro
Leu126Pro + Gly127Pro + Pro129Ser + Ser130Asp
Gly127Pro + Gly128Gln + Gly131Glu + Ser132Glu
Leu126Ile + Gly127Gln + Gly131Asp + Ser132Glu
Leu126Val + Gly131Asp + Ser132Asp + Ala133Pro
Gly128Asp + Pro129Asp + Gly131Asn + Ala133Pro
Pro129Asn + Gly131Ser + Ser132Asp + Ala133Asp
Leu126Gln + Gly131Pro + Ser132Asp + Ala133Asp
Gly127Pro + Ser130Glu + Gly131Glu + Ala133His
Leu126Gln + Pro129Gln + Ser130Asp + Gly131Glu
Gly127Ser + Ser130Asp + Gly131Glu + Ala133Gln
Leu126Ser + Gly127Pro + Pro129Glu + Ser130Glu
Ser130Glu + Gly131Glu + Ser132Glu + Ala133Ser
Gly127Gln + Ser130Glu + Gly131Asp + Ser132Asp
Gly128Gln + Ser130Glu + Gly131Asp + Ser132Asp
Gly127Asn + Ser130Glu + Gly131Asp + Ser132Asp
Gly127Ser + Pro129Asp + Ser130Asp + Gly131Glu
Gly127Asn + Pro129Asp + Ser130Asp + Gly131Asp
Gly128Asn + Pro129Glu + Ser130Glu + Gly131Asp
Leu126Ser + Gly128Asp + Ser130Glu + Ala133Pro
Gly127Asn + Gly128Asp + Ser130Glu + Ala133Pro
Gly128Glu + Ser130Glu + Gly131Pro + Ala133His
Leu126Val + Ser130Asp + Ser132Asp + Ala133Asn
Pro129Ser + Ser130Glu + Ser132Asp + Ala133Gly
Leu126His + Ser130Glu + Ser132Asp + Ala133His
Leu126Ala + Ser130Glu + Ser132Glu + Ala133Asn
Gly127Pro + Gly128Gln + Ser130Asp + Ser132Glu
Leu126Ser + Ser130Asp + Gly131Pro + Ser132Asn
Ser130Glu + Gly131Pro + Ser132Glu + Ala133Ser
Gly128Gln + Ser130Asp + Gly131Ser + Ser132Glu
Leu126Ala + Pro129Asn + Ser130Asp + Ser132Glu
Gly127Gln + Gly128Pro + Pro129Glu + Gly131Asp
Gly128Gln + Pro129Asp + Gly131Glu + Ala133Asn
Leu126Asn + Pro129Glu + Gly131Asp + Ala133Ser
Leu126Met + Pro129Glu + Gly131Glu + Ala133Thr
Gly127Asp + Gly128Gln + Pro129Asp + Ala133Gln
Leu126His + Pro129Gly + Gly131Glu + Ala133Glu
Gly128Glu + Pro129Gly + Gly131Asp + Ala133Asn
Pro129Gly + Ser130Glu + Ser132Asp + Ala133Glu
Leu126Gln + Ser130Glu + Ser132Glu + Ala133Glu
Leu126Gly + Pro129Asp + Ser130Glu + Ser132Glu
Pro129Asp + Ser130Glu + Gly131Ser + Ser132Asp

TABLE 14

Loop 4 - Single Mutation Variants

Gly154Asn
Gly154Asp
Gly154Gln
Gly154Glu
Gly154Pro
Gly154Ser
Asn155Asp
Asn155Gln
Asn155Glu
Asn155Ser
Glu156Asp
Gly157Asn
Gly157Asp
Gly157Gln
Gly157Glu
Gly157Pro
Gly157Ser
Thr158Asn
Thr158Asp
Thr158Gln
Thr158Glu
Thr158Gly
Thr158Pro
Thr158Ser
Ser159Asp
Ser159Glu
Gly160Asn
Gly160Asp
Gly160Gln
Gly160Glu
Gly160Pro
Gly160Ser
Ser161Asp
Ser161Glu
Ser162Asp
Ser162Glu
Ser163Asp
Ser163Glu
Thr164Asn
Thr164Asp
Thr164Gln
Thr164Glu
Thr164Gly
Thr164Pro
Thr164Ser
Val165Ala
Val165Asn
Val165Asp
Val165Cys
Val165Gln
Val165Glu
Val165Gly
Val165His
Val165Met
Val165Pro
Val165Ser
Val165Thr
Gly166Asn
Gly166Asp
Gly166Gln
Gly166Glu
Gly166Pro
Gly166Ser

TABLE 14-continued

Loop 4 - Single Mutation Variants

Tyr167Ala
Tyr167Asn
Tyr167Asp
Tyr167Cys
Tyr167Gln
Tyr167Glu
Tyr167Gly
Tyr167His
Tyr167Ile
Tyr167Leu
Tyr167Met
Tyr167Pro
Tyr167Ser
Tyr167Thr
Tyr167Val

TABLE 15

Loop 4 Double Mutation Variants

| | | |
|---|---|---|
| Asn155Ser | + | Glu156Asp |
| Gly154Ser | + | Tyr167Gln |
| Gly154Glu | + | Val165Ala |
| Asn155Glu | + | Thr164Pro |
| Gly157Pro | + | Ser159Asp |
| Gly154Ser | + | Ser161Asp |
| Ser161Glu | + | Val166Pro |
| Gly154Gln | + | Ser161Glu |
| Asn155Asp | + | Thr158Pro |
| Thr164Asn | + | Gly166Gln |
| Asn155Glu | + | Tyr167His |
| Glu156Asp | + | Thr158Gly |
| Gly154Pro | + | Gly157Glu |
| Asn155Ser | + | Tyr167Asp |
| Thr158Pro | + | Gly166Asp |
| Thr164Gln | + | Tyr167Glu |
| Gly157Gln | + | Thr158Glu |
| Thr158Asn | + | Ser162Asp |
| Gly154Asn | + | Tyr167Gln |
| Gly157Gln | + | Ser161Asp |
| Thr164Asp | + | Tyr167Ala |
| Gly160Asp | + | Val165His |
| Gly154Gln | + | Gly157Ser |
| Glu156Asp | + | Tyr167Ile |
| Asn155Ser | + | Thr158Asp |
| Gly157Gln | + | Thr164Pro |
| Thr164Ser | + | Tyr167Ile |
| Ser159Glu | + | Tyr167Thr |
| Thr164Glu | + | Val165Gln |
| Thr158Gly | + | Gly160Ser |
| Ser161Asp | + | Gly166Pro |
| Gly154Glu | + | Gly166Ser |
| Gly160Asp | + | Val165Asn |
| Ser162Glu | + | Val165Gln |
| Gly157Asn | + | Ser159Glu |
| Ser161Asp | + | Val165Asn |
| Asn155Asp | + | Val165Pro |
| Glu156Asp | + | Gly166Ser |
| Gly154Pro | + | Ser159Asp |
| Gly154Ser | + | Tyr167Cys |
| Gly160Pro | + | Thr164Asp |
| Ser161Glu | + | Val165Gly |
| Ser162Glu | + | Tyr167Asp |
| Gly154Asn | + | Gly166Glu |
| Ser161Glu | + | Tyr167Ala |
| Gly160Gln | + | Val165Pro |
| Gly154Glu | + | Val165Gly |
| Gly160Ser | + | Ser163Asp |
| Gly157Glu | + | Thr158Asn |
| Gly160Asp | + | Val165Pro |
| Gly160Asp | + | Ser162Asp |
| Thr164Gln | + | Gly166Gln |
| Asn155Ser | + | Thr158Gln |
| Ser161Glu | + | Tyr167Gly |

TABLE 15-continued

Loop 4 Double Mutation Variants

| | | |
|---|---|---|
| Ser162Asp | + | Gly166Ser |
| Gly154Glu | + | Thr158Gly |
| Gly154Ser | + | Thr158Ser |
| Gly157Asp | + | Gly160Pro |
| Ser163Glu | + | Val165His |
| Gly154Pro | + | Gly166Asp |

TABLE 16

Loop 4 Triple Mutation Variants

| | | | | |
|---|---|---|---|---|
| Gly154Gln | + | Asn155Ser | + | Glu156Asp |
| Gly154Ser | + | Gly160Asp | + | Tyr167Gln |
| Asn155Glu | + | Gly157Ser | + | Thr164Pro |
| Gly157Asp | + | Ser159Asp | + | Gly160Ser |
| Glu156Asp | + | Gly160Ser | + | Val165Thr |
| Gly160Pro | + | Ser162Glu | + | Thr164Asp |
| Gly154Ser | + | Glu156Asp | + | Thr158Gln |
| Gly160Asn | + | Ser162Glu | + | Gly166Ser |
| Gly160Ser | + | Val165Gly | + | Gly166Glu |
| Thr158Gln | + | Ser162Asp | + | Tyr167Val |
| Gly157Gln | + | Ser162Glu | + | Tyr167Leu |
| Ser162Glu | + | Thr164Gln | + | Val165Cys |
| Gly157Ser | + | Val165Met | + | Gly166Glu |
| Gly154Ser | + | Glu156Asp | + | Gly166Pro |
| Thr158Ser | + | Ser161Asp | + | Thr164Gly |
| Glu156Asp | + | Gly157Ser | + | Gly160Asn |
| Gly154Gln | + | Asn155Asp | + | Gly166Ser |
| Ser163Glu | + | Val165Thr | + | Tyr167Pro |
| Gly157Asp | + | Thr158Gln | + | Val165Ser |
| Gly157Asn | + | Ser159Asp | + | Gly166Ser |
| Gly160Gln | + | Ser163Glu | + | Val165Met |
| Gly154Asn | + | Asn155Asp | + | Gly157Pro |
| Glu156Asp | + | Thr158Asn | + | Val165Cys |
| Thr158Asn | + | Gly160Glu | + | Thr164Pro |
| Gly154Asn | + | Gly157Pro | + | Thr158Gln |
| Asn155Glu | + | Gly154Ser | + | Thr158Ser |
| Thr158Glu | + | Gly160Ser | + | Tyr167Val |
| Asn155Gln | + | Glu156Asp | + | Thr164Ser |
| Asn155Ser | + | Ser162Glu | + | Val165Met |
| Gly154Gln | + | Thr158Gly | + | Gly166Asp |
| Ser163Glu | + | Val165Ala | + | Gly166Asn |
| Asn155Ser | + | Gly160Glu | + | Thr164Gln |
| Gly157Asp | + | Thr164Ser | + | Gly166Pro |
| Ser163Asp | + | Thr164Glu | + | Tyr167Met |
| Ser163Asp | + | Thr164Asp | + | Val165Met |
| Glu156Asp | + | Gly157Asp | + | Thr164Gln |
| Gly157Gln | + | Gly166Asp | + | Tyr167Glu |
| Ser161Asp | + | Ser162Glu | + | Tyr167His |
| Gly154Asn | + | Ser159Asp | + | Ser162Glu |
| Ser159Asp | + | Ser162Glu | + | Val165Cys |
| Ser159Glu | + | Gly160Ser | + | Ser161Asp |
| Thr158Asp | + | Ser161Glu | + | Ser162Glu |
| Ser161Glu | + | Ser163Asp | + | Thr164Ser |
| Ser161Glu | + | Ser163Glu | + | Val165His |
| Asn155Glu | + | Glu156Asp | + | Thr158Glu |
| Gly157Glu | + | Thr164Glu | + | Val165Gly |
| Ser161Asp | + | Ser163Glu | + | Thr164Glu |
| Gly157Glu | + | Thr158Gln | + | Ser159Glu |
| Gly157Glu | + | Ser159Asp | + | Tyr167Cys |
| Gly157Asp | + | Ser163Glu | + | Thr164Glu |
| Ser159Glu | + | Ser163Asp | + | Thr164Gly |
| Ser159Asp | + | Ser163Asp | + | Thr164Asn |
| Thr158Asp | + | Ser161Asp | + | Ser163Glu |
| Thr158Glu | + | Ser162Asp | + | Thr164Asn |
| Thr158Glu | + | Ser162Asp | + | Val165Thr |
| Gly157Ser | + | Thr158Asp | + | Ser162Glu |
| Thr158Asp | + | Ser163Glu | + | Thr164Asn |
| Thr158Glu | + | Ser163Asp | + | Tyr167Gly |
| Glu156Asp | + | Gly166Glu | + | Tyr167Ile |
| Asn155Glu | + | Gly157Pro | + | Thr164Asp |

TABLE 17

Loop 4 - Quadruple Mutation Variants

| | | | | | | | |
|---|---|---|---|---|---|---|---|
| Ser159Glu | + | Thr164Ser | + | Val165Thr | + | Gly166Pro |
| Asn155Ser | + | Gly157Pro | + | Val165Ser | + | Gly166Glu |
| Gly157Asn | + | Val165Pro | + | Gly166Glu | + | Tyr167Val |
| Thr158Ser | + | Gly160Gln | + | Val165His | + | Gly166Asp |
| Gly154Ser | + | Gly157Pro | + | Ser163Glu | + | Thr164Ser |
| Gly154Ser | + | Gly157Pro | + | Ser163Glu | + | Thr164Ser |
| Gly154Ser | + | Gly157Pro | + | Ser163Glu | + | Thr164Ser |
| Gly154Ser | + | Gly157Pro | + | Ser163Glu | + | Thr164Ser |
| Gly157Gln | + | Gly160Asp | + | Thr164Ser | + | Val165Asn |
| Gly157Asp | + | Gly160Asp | + | Val165Cys | + | Tyr167Leu |
| Glu156Asp | + | Thr158Ser | + | Val165Asp | + | Gly166Pro |
| Glu156Asp | + | Thr158Pro | + | Thr164Gln | + | Val165Pro |
| Asn155Gln | + | Glu156Asp | + | Thr164Gly | + | Val165Thr |
| Thr158Gly | + | Gly160Ser | + | Ser163Asp | + | Tyr167Asp |
| Ser159Asp | + | Gly160Gln | + | Gly166Ser | + | Tyr167Pro |
| Gly154Pro | + | Thr164Gln | + | Val165Gly | + | Gly166Asp |
| Gly154Asn | + | Gly160Pro | + | Ser161Glu | + | Gly166Pro |
| Asn155Ser | + | Gly157Asn | + | Thr164Gln | + | Tyr167Asp |
| Gly157Asn | + | Thr158Asn | + | Ser163Glu | + | Val165Gln |
| Gly160Glu | + | Ser161Asp | + | Val165Met | + | Tyr167Pro |
| Asn155Glu | + | Glu156Asp | + | Thr158Gln | + | Gly166Pro |
| Asn155Asp | + | Glu156Asp | + | Val165Asn | + | Gly166Asn |
| Asn155Asp | + | Glu156Asp | + | Gly160Ser | + | Thr164Asp |
| Gly154Ser | + | Thr158Gln | + | Ser162Gln | + | Ser463Glu |
| Gly154Asn | + | Asn155Gln | + | Ser163Glu | + | Thr164Glu |
| Glu156Asp | + | Gly157Glu | + | Gly160Gln | + | Thr164Gly |
| Glu156Asp | + | Gly157Glu | + | Thr158Ser | + | Val165Cys |
| Gly154Pro | + | Gly157Pro | + | Thr158Asp | + | Ser159Asp |
| Gly154Ser | + | Gly157Asn | + | Thr158Glu | + | Ser159Glu |
| Gly157Pro | + | Gly160Pro | + | Gly166Asp | + | Tyr167Glu |
| Gly154Asn | + | Ser161Glu | + | Ser162Glu | + | Tyr167Asp |
| Gly154Asp | + | Asn155Asp | + | Thr164Gln | + | Gly166Asn |
| Gly154Gln | + | Ser159Glu | + | Gly160Glu | + | Ser161Asp |
| Thr158Ser | + | Ser159Asp | + | Gly160Asp | + | Ser161Asp |
| Asn155Ser | + | Glu156Asp | + | Gly157Asp | + | Thr158Glu |
| Gly157Asn | + | Ser159Asp | + | Ser161Glu | + | Ser162Glu |
| Gly154Asn | + | Glu156Asp | + | Gly157Glu | + | Thr164Glu |
| Gly157Gln | + | Gly160Asp | + | Ser162Asp | + | Val165Thr |
| Gly160Glu | + | Ser162Asp | + | Thr164Asn | + | Gly166Gln |
| Gly154Asp | + | Asn155Ser | + | Glu156Asp | + | Thr164Ser |
| Gly154Asp | + | Glu156Asp | + | Gly157Glu | + | Thr158Gly |
| Gly154Asp | + | Gly157Pro | + | Ser159Asp | + | Ser161Asp |
| Ser159Glu | + | Ser161Asp | + | Gly166Ser | + | Tyr167His |
| Ser159Asp | + | Ser161Asp | + | Gly166Pro | + | Tyr167Ser |
| Glu156Asp | + | Thr158Glu | + | Val165Ala | + | Gly166Gln |
| Glu156Asp | + | Thr158Asp | + | Gly166Pro | + | Tyr167Ala |
| Asn155Gln | + | Thr158Asp | + | Thr164Asp | + | Tyr167Val |
| Ser163Glu | + | Thr164Asp | + | Val165Met | + | Gly166Glu |
| Ser161Asp | + | Ser163Asp | + | Val165Thr | + | Tyr167His |
| Ser161Asp | + | Ser163Glu | + | Thr164Gln | + | Gly166Asp |
| Gly157Pro | + | Ser159Glu | + | Ser161Asp | + | Ser163Glu |
| Gly154Pro | + | Glu156Asp | + | Ser163Asp | + | Thr164Glu |
| Asn155Asp | + | Glu156Asp | + | Thr158Asp | + | Thr164Asn |
| Glu156Asp | + | Ser159Asp | + | Thr164Asp | + | Val165Ala |
| Thr158Gln | + | Ser159Asp | + | Ser163Glu | + | Val165Cys |
| Gly154Gln | + | Ser159Asp | + | Ser163Asp | + | Gly166Pro |
| Asn155Ser | + | Gly160Asp | + | Ser162Glu | + | Thr164Asp |
| Gly154Gln | + | Gly160Asp | + | Ser162Glu | + | Thr164Glu |
| Glu156Asp | + | Gly160Pro | + | Val165Pro | + | Gly166Glu |
| Gly160Glu | + | Ser163Asp | + | Thr164Gly | + | Tyr167Leu |
| Gly160Glu | + | Ser163Glu | + | Thr164Pro | + | Gly166Gln |
| Asn155Asp | + | Thr158Pro | + | Ser163Glu | + | Thr164Asp |
| Asn155Ser | + | Glu156Asp | + | Ser163Asp | + | Gly166Glu |

TABLE 18

Loop 5 - Single Mutation Variants

Ala187Asn
Ala187Asp
Ala187Gln
Ala187Glu
Ala187Gly
Ala187His

TABLE 18-continued

Loop 5 - Single Mutation Variants

Ala187Pro
Ala187Ser
Ala187Thr
Ser188Asp
Ser188Glu
Phe189Ala
Phe189Asn
Phe189Asp
Phe189Cys
Phe189Gln
Phe189Glu
Phe189Gly
Phe189His
Phe189Ile
Phe189Leu
Phe189Met
Phe189Pro
Phe189Ser
Phe189Thr
Phe189Tyr
Phe189Val
Ser190Asp
Ser190Glu
Ser191Asp
Ser191Glu

TABLE 19

Loop 5 Double Mutation Variants

| | | |
|---|---|---|
| Ala187Asp | + | Phe189Gln |
| Ala187Ser | + | Ser188Asp |
| Ser188Glu | + | Phe189Pro |
| Ala187Asp | + | Phe189His |
| Ala187Asn | + | Ser191Glu |
| Ala187Gln | + | Ser191Asp |
| Ala187Glu | + | Phe189Pro |
| Ala187Pro | + | Phe189Asp |
| Ser188Asp | + | Phe189Cys |
| Phe189His | + | Ser191Asp |
| Ser188Glu | + | Phe189Ala |
| Ala187His | + | Ser188Asp |
| Ala187Asn | + | Ser188Glu |
| Ser188Glu | + | Phe189Gln |
| Ala187Asp | + | Phe189Ser |
| Ser188Asp | + | Phe189Val |
| Ala187Gln | + | Ser188Glu |
| Ala187Ser | + | Ser188Glu |
| Ala187Pro | + | Ser191Asp |
| Ser188Glu | + | Phe189Val |
| Phe189Ser | + | Ser191Glu |
| Ala187Gly | + | Ser191Glu |
| Ala187Asn | + | Ser191Asp |
| Ala187Thr | + | Ser191Asp |
| Ala187His | + | Ser188Glu |
| Ser188Glu | + | Phe189Gly |
| Ala187Ser | + | Phe189Ile |
| Ser188Glu | + | Phe189Met |
| Phe189Asn | + | Ser191Asp |
| Ala187Gln | + | Phe189Tyr |
| Ala187Gln | + | Ser191Glu |
| Ala187Ser | + | Phe189Ala |
| Phe189Val | + | Ser191Asp |
| Ser188Glu | + | Phe189Leu |
| Ala187Pro | + | Ser188Glu |
| Phe189Asn | + | Ser191Glu |
| Phe189Ile | + | Ser191Asp |
| Ala187Glu | + | Phe189Met |
| Ala187His | + | Ser191Glu |
| Ser188Asp | + | Phe189Tyr |
| Ser188Gly | + | Phe189Val |
| Ser188Asp | + | Phe189Gln |
| Ala187Gly | + | Phe189Tyr |
| Ala187Gln | + | Phe189Asp |

TABLE 19-continued

Loop 5 Double Mutation Variants

| | | |
|---|---|---|
| Phe189Tyr | + | Ser191Glu |
| Ala187Ser | + | Ser191Asp |
| Ala187Thr | + | Ser188Glu |
| Ala187Asn | + | Ser188Asp |
| Ala187Gly | + | Ser188Asp |
| Ala187Gly | + | Phe189Cys |
| Phe189Cys | + | Ser191Glu |
| Ala187Asp | + | Phe189Gly |
| Ser188Asp | + | Phe189Leu |
| Ser188Asp | + | Phe189Gly |
| Ala187Asn | + | Phe189Asp |
| Ala187Pro | + | Ser191Glu |
| Phe189Met | + | Ser191Asp |
| Ala187Thr | + | Ser188Asp |
| Phe189Ala | + | Ser191Glu |
| Phe189Leu | + | Ser191Glu |

TABLE 20

Loop 5 - Triple Mutation Variants

| | | | | | |
|---|---|---|---|---|---|
| Ala187Pro | + | Phe189Cys | + | Ser191Glu |
| Ala187Thr | + | Phe189Tyr | + | Ser191Glu |
| Ala187Ser | + | Ser188Glu | + | Phe189Ser |
| Ala187Gln | + | Phe189Asn | + | Ser191Glu |
| Ala187Gln | + | Ser188Asp | + | Phe189His |
| Ala187Gln | + | Ser188Glu | + | Phe189His |
| Ala187Gly | + | Ser188Asp | + | Phe189Met |
| Ala187Gly | + | Ser188Asp | + | Phe189Cys |
| Ala187Pro | + | Phe189His | + | Ser191Glu |
| Ala187Pro | + | Phe189Gly | + | Ser191Glu |
| Ala187Asn | + | Ser188Asp | + | Phe189Asn |
| Ala187Gly | + | Ser188Glu | + | Phe189Ser |
| Ala187Gln | + | Phe189Met | + | Ser191Asp |
| Ala187Asp | + | Ser188Asp | + | Phe189Pro |
| Ala187Thr | + | Phe189His | + | Ser191Asp |
| Ala187Asn | + | Ser188Glu | + | Phe189Cys |
| Ala187Gln | + | Phe189Val | + | Ser191Glu |
| Ala187Pro | + | Phe189Met | + | Ser191Glu |
| Ala187Ser | + | Ser188Glu | + | Phe189His |
| Ala187Ser | + | Phe189Gln | + | Ser191Asp |
| Ala187Gln | + | Ser188Asp | + | Phe189Pro |
| Ala187Gly | + | Ser188Glu | + | Phe189Gly |
| Ala187His | + | Phe189Gln | + | Ser191Glu |
| Ala187Thr | + | Ser188Glu | + | Phe189Ile |
| Ala187Pro | + | Phe189Gly | + | Ser191Glu |
| Ala187Thr | + | Phe189Met | + | Ser191Glu |
| Ala187Gly | + | Phe189Thr | + | Ser191Glu |
| Ala187Gln | + | Phe189Leu | + | Ser191Glu |
| Ala187Thr | + | Phe189Thr | + | Ser191Asp |
| Ala187Gln | + | Ser188Asp | + | Phe189Met |
| Ala187Pro | + | Phe189Ser | + | Ser191Glu |
| Ala187Asp | + | Ser188Glu | + | Phe189Val |
| Ala187Glu | + | Ser188Glu | + | Phe189Ser |
| Ala187Asp | + | Ser188Glu | + | Phe189Met |
| Ala187Asp | + | Ser188Asp | + | Phe189Gln |
| Ala187Asp | + | Ser188Glu | + | Phe189Cys |
| Ala187Asp | + | Ser188Glu | + | Phe189Tyr |
| Ala187Glu | + | Ser188Glu | + | Phe189Tyr |
| Ala187Asp | + | Ser188Asp | + | Phe189Gly |
| Ala187Glu | + | Ser188Glu | + | Phe189Leu |
| Ala187Asp | + | Ser188Glu | + | Phe189Ser |
| Ala187Glu | + | Ser188Asp | + | Phe189Gly |
| Ala187Asp | + | Ser188Asp | + | Phe189Pro |
| Ala187Asp | + | Ser188Glu | + | Phe189His |
| Ala187Glu | + | Ser188Glu | + | Phe189Thr |
| Ala187Glu | + | Ser188Asp | + | Phe189Ile |
| Ala187Glu | + | Ser188Asp | + | Phe189Asn |
| Ala187Ser | + | Ser188Glu | + | Phe189Glu |
| Ala187Gly | + | Ser188Asp | + | Phe189Glu |
| Ala187Gly | + | Ser188Glu | + | Phe189Asp |
| Ala187Pro | + | Ser188Glu | + | Phe189Asp |
| Ala187Asp | + | Ser188Glu | + | Phe189Glu |
| Ala187Glu | + | Ser188Asp | + | Phe189Asp |

TABLE 20-continued

Loop 5 - Triple Mutation Variants

| | | | | | |
|---|---|---|---|---|---|
| Ala187Asp | + | Ser188Glu | + | Phe189Asp |
| Ala187Glu | + | Ser188Glu | + | Phe189Glu |
| Ala187Gly | + | Phe189Asp | + | Ser191Asp |
| Ala187Gly | + | Phe189Glu | + | Ser191Glu |
| Ala187Thr | + | Phe189Glu | + | Ser191Glu |
| Ser188Glu | + | Phe189Glu | + | Ser191Glu |
| Ser188Glu | + | Phe189Glu | + | Ser191Asp |

TABLE 21

Loop 5 - Quadruple Mutation Variants

| | | | | | | | |
|---|---|---|---|---|---|---|---|
| Ala187Ser | + | Ser188Glu | + | Phe189Asp | + | Ser191Asp |
| Ala187Pro | + | Ser188Glu | + | Phe189Glu | + | Ser191Glu |
| Ala187His | + | Ser188Glu | + | Phe189Asp | + | Ser191Glu |
| Ala187Gly | + | Ser188Asp | + | Phe189Asp | + | Ser191Glu |
| Ala187His | + | Ser188Glu | + | Phe189Glu | + | Ser191Asp |
| Ala187Thr | + | Ser188Asp | + | Phe189Asp | + | Ser191Glu |
| Ala187Asp | + | Ser188Glu | + | Phe189Glu | + | Ser191Glu |
| Ala187Pro | + | Ser188Asp | + | Phe189Glu | + | Ser191Glu |
| Ala187Pro | + | Ser188Asp | + | Phe189Asp | + | Ser191Asp |
| Ala187Ser | + | Ser188Glu | + | Phe189Asp | + | Ser191Glu |
| Ala187His | + | Ser188Asp | + | Phe189Glu | + | Ser191Asp |
| Ala187Thr | + | Ser188Glu | + | Phe189Asp | + | Ser191Asp |
| Ala187Asp | + | Ser188Asp | + | Phe189Glu | + | Ser191Glu |
| Ala187Asp | + | Ser188Glu | + | Phe189Asp | + | Ser191Glu |
| Ala187Gly | + | Ser188Asp | + | Phe189Glu | + | Ser191Glu |
| Ala187Glu | + | Ser188Asp | + | Phe189Gly | + | Ser191Asp |
| Ala187Glu | + | Ser188Glu | + | Phe189Met | + | Ser191Asp |
| Ala187Asp | + | Ser188Glu | + | Phe189Ile | + | Ser191Glu |
| Ala187Asp | + | Ser188Glu | + | Phe189Leu | + | Ser191Asp |
| Ala187Asp | + | Ser188Glu | + | Phe189Thr | + | Ser191Asp |
| Ala187Glu | + | Ser188Glu | + | Phe189Leu | + | Ser191Asp |
| Ala187Glu | + | Ser188Glu | + | Phe189Tyr | + | Ser191Asp |
| Ala187Glu | + | Ser188Glu | + | Phe189Gln | + | Ser191Asp |
| Ala187Glu | + | Ser188Glu | + | Phe189Cys | + | Ser191Glu |
| Ala187Glu | + | Ser188Glu | + | Phe189Gln | + | Ser191Glu |
| Ala187Glu | + | Ser188Glu | + | Phe189Pro | + | Ser191Glu |
| Ala187Asp | + | Ser188Glu | + | Phe189Ser | + | Ser191Glu |
| Ala187Glu | + | Ser188Glu | + | Phe189Cys | + | Ser191Asp |
| Ala187Asp | + | Ser188Asp | + | Phe189Leu | + | Ser191Glu |
| Ala187Glu | + | Ser188Asp | + | Phe189Ile | + | Ser191Asp |
| Ala187Asp | + | Ser188Asp | + | Phe189His | + | Ser191Glu |
| Ala187Glu | + | Ser188Asp | + | Phe189His | + | Ser191Asp |
| Ala187Glu | + | Ser188Asp | + | Phe189Val | + | Ser191Asp |
| Ala187Asp | + | Ser188Glu | + | Phe189Gly | + | Ser191Glu |
| Ala187Asp | + | Ser188Asp | + | Phe189Cys | + | Ser191Asp |
| Ala187Glu | + | Ser188Glu | + | Phe189Asn | + | Ser191Glu |
| Ala187Asp | + | Ser188Asp | + | Phe189Thr | + | Ser191Glu |
| Ala187Asp | + | Ser188Asp | + | Phe189Ile | + | Ser191Asp |
| Ala187Asp | + | Ser188Glu | + | Phe189Ala | + | Ser191Glu |
| Ala187Asp | + | Ser188Asp | + | Phe189Val | + | Ser191Glu |
| Ala187Glu | + | Ser188Glu | + | Phe189Ala | + | Ser191Glu |
| Ala187Asp | + | Ser188Asp | + | Phe189Ser | + | Ser191Asp |
| Ala187Asp | + | Ser188Glu | + | Phe189Asn | + | Ser191Asp |
| Ala187Asp | + | Ser188Asp | + | Phe189Cys | + | Ser191Glu |
| Ala187Asp | + | Ser188Glu | + | Phe189Cys | + | Ser191Asp |
| Ala187Glu | + | Ser188Asp | + | Phe189Ser | + | Ser191Glu |
| Ala187Asp | + | Ser188Asp | + | Phe189Tyr | + | Ser191Glu |
| Ala187Asp | + | Ser188Glu | + | Phe189Ala | + | Ser191Asp |
| Ala187Gly | + | Ser188Asp | + | Phe189Thr | + | Ser191Asp |
| Ala187His | + | Ser188Asp | + | Phe189Met | + | Ser191Glu |
| Ala187Thr | + | Ser188Asp | + | Phe189Ser | + | Ser191Glu |
| Ala187Ser | + | Ser188Glu | + | Phe189Met | + | Ser191Glu |
| Ala187Ser | + | Ser188Asp | + | Phe189Ser | + | Ser191Asp |
| Ala187Thr | + | Ser188Asp | + | Phe189Tyr | + | Ser191Glu |
| Ala187Ser | + | Ser188Glu | + | Phe189Ala | + | Ser191Glu |
| Ala187Asn | + | Ser188Asp | + | Phe189Gly | + | Ser191Asp |
| Ala187Gln | + | Ser188Asp | + | Phe189Asn | + | Ser191Glu |
| Ala187Asn | + | Ser188Asp | + | Phe189His | + | Ser191Glu |
| Ala187Gly | + | Ser188Asp | + | Phe189Ser | + | Ser191Glu |
| Ala187His | + | Ser188Asp | + | Phe189Val | + | Ser191Asp |

TABLE 22

Multi-loop Double Mutation Variants

Leu 96Gly + Ser204Glu
Gln 59Ser + Asn 62Ser
Val 95Gln + Asn218Asp
Tyr104Cys + Lys213Glu
Gly127Gln + Ala216Pro
Ser188Glu + Gly215Asn
Gly 97Gln + Ile107Ala
Gln206Asp + Tyr217Thr
Asp 60Glu + Gln206Asn
Thr158Asp + Gln206Ser
Pro210Gln + Gly215Asn
Tyr104Glu + Ile107Leu
Tyr167Pro + Gly211Glu
Ile107Leu + Ala187Asp
Gly 97Glu + Thr164Pro
Thr 66Pro + Val203Cys
Ala133Gly + Tyr217Ser
Ser105Glu + Phe189Val
Tyr167Asp + Ala187Thr
Ser161Glu + Ala216Thr
Ser 63Asp + Gln103Ser
Leu 96Gln + Pro129Glu
Ala 98Gly + Tyr214Glu
Leu 96Asn + Asn212Ser
Ser 63Asp + Phe189Leu
Thr158Gln + Lys213Glu
Leu126Gln + Gly160Asp
Ser159Asp + Tyr217Gln
Ser101Asp + Val203Ala
Gly100Asn + Gly215Glu
Gln 59Asp + Gly131Gln
Gly157Glu + Leu209Pro
Trp106Pro + Tyr217Ile
Ala216Ser + Gly219Asp
Thr 66Gln + Leu126Asn
Gly102Gln + Gly219Asp
Asn212Ser + Lys213Asp
Gln206Ser + Lys213Glu
Tyr104Glu + Asn155Gln
Val 95Asp + Leu126Ser
Tyr104Asp + Gly166Gln
Thr 66Pro + Ser204Glu
Asn 61Glu + Phe189Pro
Asp 60Glu + Tyr167Ala
Pro129Gln + Gln206Asp
Gly160Asp + Ala216Asn
Ser161Glu + Gly166Asn
Leu 96Pro + Gly100Asp
Trp106Asn + Val203Asn
Ser101Asp + Gly127Ser
Ala133Gln + Val203Asp
Ser101Asp + Gly202Ser
Ile107Ala + Gly160Asn
Ala133Thr + Tyr214Ile
Phe189Ser + Ser204Asp
Gly 97Asp + Trp106Phe
Gln 59Asn + Glu156Asp
Pro201Ser + Lys213Glu
Ser162Glu + Gly202Gln
Gly 65Ser + Gln206Asp
Lys213Asp + Ala216Pro
Val203Ala + Lys213Asp
Ala216Thr + Tyr217Pro
Gly131Asn + Asn218Glu
Tyr104Glu + Gly131Pro
Gly127Ser + Thr158Asp
Trp106Gly + Ser132Asp
Asn 62Ser + Ala187Ser
Ser163Asp + Phe189Ser
Pro201Gln + Gly215Glu
Gly100Gln + Tyr217Thr
Ser130Glu + Gly154Asn
Asp 60Glu + Tyr214Thr
Asn155Glu + Tyr217Gln
Ala 98Gln + Gly102Asn
Pro201Asn + Gly219Asp
Thr 66Ser + Gly127Gln

TABLE 22-continued

Multi-loop Double Mutation Variants

Leu126Glu + Ala216Thr
Asn 61Ser + Asn155Glu
Thr 66Ser + Gly157Asp
Pro129Ser + Thr164Gln
Ala216Asp + Tyr217Val
Ser130Glu + Tyr217Leu
Asn 62Asp + Tyr214Leu
Val 95Ser + Phe189Val
Gly100Pro + Ser159Asp
Asn155Gln + Ser204Glu
Pro129Asp + Val203Ser
Ser101Glu + Thr158Asn
Ala187Pro + Asn218Asp
Val 95Gly + Ser161Asp
Gly202Pro + Ala216Gln
Gly 97Ser + Gly215Asp
Tyr167Asp + Gln206Ser
Thr 66Ser + Asn212Glu
Ala216Thr + Tyr217Gln
Ala200Asn + Tyr217Ala
Asp 60Glu + Val203Pro
Val 95Thr + Tyr217Met
Val203Asn + Lys213Glu
Gly102Asp + Val203Gly
Ser130Asp + Ala133Thr
Tyr104Ala + Gly166Ser
Leu 96Met + Tyr217Asp
Ser101Asp + Gly102Pro
Ser101Asp + Thr220Pro
Val 95Asn + Ala216Pro
Tyr104Asn + Pro129Asp
Gly202Asn + Gln206Asp
Gln 59Glu + Ile107Cys
Thr 66Glu + Tyr104Pro
Val 95Met + Asp 99Glu
Ser204Glu + Gly211Pro
Pro210Glu + Gly219Ser
Leu126Pro + Ser204Glu
Pro129Asp + Ala200His
Ile107Gly + Gly215Pro
Thr 66Glu + Gln206Asn
Asn155Asp + Leu209His
Gly211Asp + Tyr217Val
Ala216Asp + Thr220Gln
Thr158Gly + Ser204Asp
Gly100Glu + Ile107Ser
Ala 98Ser + Gly154Asn
Gln103Asn + Ala216Glu
Gly154Gln + Pro210Gln
Leu126Pro + Ala216His
Ala216His + Tyr217Leu
Gly154Glu + Tyr217Ser
Gly 97Ser + Tyr167Thr
Trp106Ile + Ala216Gly
Gly102Ser + Phe189Gly
Gly154Glu + Gly219Asn
Lys213Glu + Ala216Pro
Asn 62Asp + Leu126Ser
Thr 66Gly + Gln206Glu
Gly157Pro + Val203Cys
Gln 59Asp + Tyr214Ser
Leu 96Met + Gly100Ser
Ala 98Gly + Lys213Asp
Asn 62Gln + Leu 96Asp
Gly127Asn + Gln206Glu
Gly160Pro + Gly219Asn
Leu 96Thr + Tyr217Ala
Trp106Phe + Tyr217Thr
Gly131Pro + Lys213Glu
Gly 65Gln + Asp 99Glu
Gly127Asn + Gly128Gln
Ala133Asn + Gly154Asn
Ser204Glu + Gly215Ser
Glu156Asp + Pro210Ser
Asp 60Glu + Gln206Ser
Asn 61Gln + Ala216Asn
Pro210Asn + Asn212Asp

TABLE 22-continued

Multi-loop Double Mutation Variants

Ala133Asp + Val203Asn
Gly219Ser + Thr220Gly
Ser191Asp + Val203Thr
Gly160Glu + Ala216Thr
Ser162Glu + Ala216Gln
Ala 98Gln + Tyr217Asn
Val 95Asp + Gln206Asn
Tyr104Ser + Ser204Asp
Gly100Pro + Phe189Gln
Gly 97Asp + Tyr217His
Gln206Ser + Gly211Asn
Ala187Asn + Ser188Asp
Ala 98Gly + Asp 99Glu
Thr164Asn + Phe189Cys
Val203Gln + Gln206Ser
Trp106Cys + Gly157Ser
Thr158Ser + Gly160Ser
Ser188Asp + Tyr217Gly
Gly157Asn + Phe189Met
Ser188Asp + Ala216Asn
Gly128Asn + Gly166Ser
Leu126Asn + Ala216Ser
Gly127Asp + Gln206Asn
Gln 59Glu + Leu 96His
Ser132Asp + Tyr217Ala
Gly166Ser + Gly219Glu
Ser163Glu + Val203Met
Ala 98His + Tyr217Met
Ala 98Pro + Ser130Asp
Gly160Asn + Ser204Glu
Gln206Asn + Gly215Asp
Gln103Ser + Ser130Asp
Ala133Gly + Thr220Gly
Ser132Glu + Ala216Gln
Asn 61Gln + Ile107His
Leu126Ala + Gly131Glu
Gln206Asp + Thr220Gly
Gln206Glu + Tyr217Cys
Gly157Ser + Pro210Asp
Gly166Glu + Tyr214Gln
Ser188Glu + Ala216His
Thr 66Glu + Gly166Gln
Gly102Pro + Gly166Glu
Val 95Gln + Tyr104Ile
Ser191Glu + Gly219Ser
Asp 99Glu + Asn218Gln
Gly100Asn + Ser105Glu
Gly166Pro + Pro210Asn
Gln 59Asn + Thr164Ser
Leu126His + Tyr214Ala
Thr 66Pro + Lys213Asp
Trp106His + Gly211Ser
Tyr167Leu + Ser204Glu
Val 95Thr + Ala133Gly
Ile107Ser + Gln206Glu
Phe189Tyr + Lys213Asp
Gly 65Asn + Asn218Asp
Tyr167Val + Lys213Glu
Gly 97Gln + Ser132Glu
Asp 99Glu + Gly102Pro
Leu126Cys + Ala216Asp
Leu126Cys + Gly127Ser
Ser191Asp + Ala216Asn
Gly100Gln + Gly154Asp
Asn 61Asp + Gly211Ser
Ser161Asp + Phe189Leu
Ile205Gln + Ala216Glu
Asn 62Gln + Tyr217Leu
Ile107Met + Ser161Asp
Leu126Ile + Tyr217Ser
Ala 98His + Ser162Asp
Asn 61Asp + Gly128Ser
Asn155Glu + Gly215Gln
Asn155Gln + Ser204Asp
Asn155Glu + Thr220Gln
Lys213Asp + Tyr217His
Gly127Pro + Ser204Glu

TABLE 22-continued

Multi-loop Double Mutation Variants

Ser204Asp + Tyr217Ala
Glu156Asp + Val203Gly
Gly127Glu + Ala133His
Gly100Asn + Gly131Ser
Gly21lGln + Lys213Asp
Ala187Asp + Phe189Leu
Ala216Glu + Tyr217Cys
Ser204Asp + Ala216Thr
Gly131Ser + Thr158Asp
Gly100Asn + Gln206Asn
Ser105Asp + Gly131Gln
Ser204Asp + Tyr214Val
Tyr214Met + Tyr217Ile
Ser 63Glu + Thr164Asn
Ile107Cys + Ala216Pro
Trp106Gly + Gln206Asp
Gly102Asp + Thr164Pro
Asp 99Glu + Ala216Gln
Lys213Glu + Ala216Gln
Ala133Ser + Pro210Glu
Asp 60Glu + Tyr104Asn
Asn 62Gln + Ile107Cys
Tyr167Ala + Gly211Asp
Glu156Asp + Tyr217Ile
Gly131Pro + Leu209Pro
Lys213Glu + Asn218Gln
Gly160Ser + Val203Glu
Asn155Ser + Tyr167Ala
Asp 60Glu + Phe189Gly
Thr164Gln + Gly219Ser
Ser162Asp + Gln206Asn
Gly100Glu + Tyr104Asn
Gly160Pro + Gln206Ser
Thr 66Gly + Ala216Gly
Tyr104Ile + Gly215Pro
Pro201Gln + Ala216Thr
Gln103Glu + Ala133Asn
Ser163Glu + Phe189His
Gly127Ser + Tyr217Ser
Gln206Asn + Leu209His
Pro210Glu + Ala216Gln
Asn 62Ser + Gln206Asn
Ser161Glu + Gly219Asn
Val203Gly + Asn212Glu
Ala 98Glu + Leu126Met
Val165Gln + Ser204Asp
Gly154Ser + Ala216His
Pro201Gly + Gly211Glu
Ser161Asp + Gly219Gln
Asn155Glu + Thr220Asn
Leu 96Glu + Ile107Leu
Thr158Ser + Gly215Ser
Ser 63Glu + Pro129Ser
Val 95Asn + Ser163Glu
Gly102Asn + Leu126Glu
Thr 66Gly + Ala216Pro
Gly157Ser + Thr158Glu
Ala 98Asp + Ala187Ser
Asp 99Glu + Thr164Gln
Thr 66Ser + Ser105Glu
Gln103Asp + Gly154Pro
Thr 66Glu + Tyr217His
Gly127Gln + Ser204Glu
Phe189Ile + Tyr217Thr
Ala133Gln + Lys213Asp
Ser130Asp + Tyr217Thr
Leu126Ile + Asn212Ser
Gly154Asn + Gln206Asp
Thr 66Pro + Glu156Asp
Gln103Asn + Lys213Asp
Phe189Met + Gln206Asp
Leu126Asn + Gly154Gln
Pro210Gly + Gly215Glu
Leu126Val + Ala216Pro
Gln206Ser + Tyr217His
Leu 96Asn + Lys213Asp
Leu126Pro + Ala216Ser

TABLE 22-continued

Multi-loop Double Mutation Variants

Val203His + Gly211Asp
Tyr167Ala + Tyr217Asp
Trp106Asn + Gln206Asn
Gly127Ser + Ser161Glu
Lys213Glu + Gly219Asn
Val 95Thr + Thr208Gly
Thr158Gly + Ser204Glu
Gly 97Pro + Trp106Tyr
Phe189Ile + Val203His
Leu 96Gln + Lys213Glu
Gln206Glu + Ala216Thr
Gly154Ser + Asn155Glu
Ser132Asp + Tyr214Asn
Pro129Gln + Ala133Pro
Ala 98Asn + Gly127Asp
Gly211Gln + Asn218Asp
Trp106Cys + Ser163Asp
Leu 96His + Ala216Gly
Gly 97Asn + Ser204Asp
Asn 61Ser + Gly157Asp
Pro210Asn + Tyr217His
Asp 60Glu + Tyr104Ala
Thr164Asn + Ala200Gly
Tyr214Val + Ala216Asp
Leu126His + Ala216Ser
Gly128Gln + Asn212Asp
Ser162Glu + Gln206Ser
Gln206Glu + Ala216Ser
Thr164Pro + Thr220Asp
Val203Ser + Gly219Asp
Gln206Asn + Gly219Asp
Ser 63Asp + Ile107Gln
Gly102Gln + Val203Ala
Ser101Glu + Val165Gln
Gln 59Ser + Gly166Glu
Ser101Glu + Tyr217Ser
Gly131Asn + Ala187Glu
Gly102Ser + Tyr214Gly
Thr158Ser + Thr220Glu
Asp 99Glu + Gly215Gln
Val 95Gly + Thr220Asp
Ala200Ser + Tyr214Val
Ser188Glu + Ala216Asp
Tyr214His + Ala216Asp
Thr158Glu + Phe189Asn
Asn155Gln + Ser191Asp
Thr 66Ser + Leu126Ser
Thr 66Gly + Gln206Asp
Ser105Asp + Tyr214Thr
Gly102Pro + Thr164Gln
Trp106Gly + Pro210Gly
Asn155Asp + Thr220Gln

TABLE 23

Multi-loop Triple Mutation Variants

Gln 59Ser + Leu 96Gly + Ser204Glu
Asn 62Ser + Val 95Gln + Asn218Asp
Tyr104Cys + Gly127Gln + Lys213Glu
Ser188Glu + Gly215Asn + Ala216Pro
Gly 97Gln + Ile107Ala + Gly157Glu
Ser162Glu + Pro210Gln + Gly215Asn
Thr 66Pro + Val203Cys + Tyr217Ser
Ser105Glu + Ala133Gly + Phe189Val
Leu 96Asn + Asn212Ser + Tyr214Glu
Gln 59Asp + Gly131Gln + Leu209Pro
Trp106Pro + Gly157Glu + Tyr217Ile
Thr 66Gln + Leu126Asn + Ser188Glu
Asn212Ser + Lys213Asp + Gly219Gln
Val 95Asp + Leu126Ser + Asn155Gln
Asn 61Glu + Thr 66Pro + Phe189Pro
Gly160Asp + Gly166Asn + Ala216Asn
Trp106Asn + Gly127Ser + Val203Asn

TABLE 23-continued

Multi-loop Triple Mutation Variants

Ser101Asp + Ile107Ala + Gly202Ser
Ala133Thr + Phe189Ser + Tyr214Ile
Gln 59Asn + Gly 97Asp + Trp106Phe
Gly157Pro + Pro210Gly + Ala216Glu
Gly160Ser + Asn212Ser + Tyr217Thr
Asn 62Gln + Gln206Asn + Ala216Ser
Pro129Ser + Gly215Glu + Tyr217Pro
Ala 98Asn + Tyr217His + Thr220Gly
Val203Gly + Gly211Glu + Ala216Asn
Gly127Glu + Tyr214Asn + Ala216His
Trp106Pro + Ala133Pro + Gln206Asp
Val 95Ser + Gly128Glu + Tyr217Cys
Ser159Asp + Gly166Gln + Gly219Gln
Leu 96Val + Glu156Asp + Gly157Pro
Ala133Gly + Thr208Pro + Tyr214Pro
Trp106Asn + Gly128Pro + Val203Met
Gly 65Ser + Gly102Asn + Ala187His
Ala200Gln + Gln206Glu + Tyr217His
Gln103Ser + Glu156Asp + Ala216Ser
Gln 59Asn + Ala216Thr + Gly219Pro
Gly102Ser + Pro210Asp + Tyr217Ile
Gly100Glu + Ile107Ser + Thr158Gly
Ala 98Glu + Gly154Gln + Pro210Gln
Gln103Glu + Leu126Pro + Ala216His
Lys213Glu + Ala216His + Tyr217Leu
Gly154Gln + Tyr167Thr + Tyr217Ser
Gly 97Ser + Trp106Ile + Ala216Gly
Gly102Ser + Phe189Gly + Gly219Asn
Gly157Pro + Gly160Asp + Val203Cys
Leu 96Met + Ala 98Gly + Gly100Ser
Gly127Asn + Gly160Pro + Gln206Glu
Leu 96Thr + Tyr217Ala + Gly219Asn
Trp106Phe + Lys213Glu + Tyr217Thr
Gly102Glu + Gly127Asn + Gly128Gln
Ala133Asn + Glyl54Asn + Ser161Asp
Asn 61Gln + Gln206Ser + Ala216Asn
Ser204Asp + Gly219Ser + Thr220Gly
Ala 98Gln + Ser159Glu + Tyr217Asn
Gly 97Asp + Gly100Pro + Phe189Gln
Gln206Ser + Gly211Asn + Tyr217His
Ala 98Gly + Ala187Asn + Ser188Asp
Asp 99Glu + Thr164Asn + Phe189Cys
Trp106Cys + Gly157Ser + Gln206Ser
Gly157Asn + Ser188Asp + Tyr217Gly
Gly166Ser + Ser188Asp + Ala216Asn
Leu126Asn + Gly128Asn + Ala216Ser
Leu 96His + Ser132Asp + Tyr217Ala
Ala 98His + Lys213Glu + Tyr217Met
Ala 98Pro + Ser130Asp + Gly160Asn
Ser130Asp + Ala133Gly + Thr220Gly
Asn 61Gln + Ile107His + Asn218Glu
Gln206Glu + Tyr217Cys + Thr220Gly
Gly157Ser + Pro210Asp + Tyr214Gln
Val 95Gln + Gly102Pro + Gly166Glu
Tyr104Ile + Ser191Glu + Gly219Ser
Asp 99Glu + Gly100Asn + Asn218Gln
Gly131Glu + Gly166Pro + Pro210Asn
Leu126His + Thr164Ser + Tyr214Ala
Thr 66Pro + Gly211Ser + Lys213Asp
Trp106His + Tyr167Leu + Ser204Glu
Val 95Thr + Ala133Gly + Gln206Glu
Gly 97Gln + Gly102Pro + Ser132Glu
Leu126Cys + Ser191Asp + Ala216Asn
Gly100Gln + Gly154Asp + Gly211Ser
Asn 62Gln + Ala216Glu + Tyr217Leu
Leu126Ile + Ser161Asp + Tyr217Ser
Pro129Glu + Asn155Gln + Thr158Gly
Gly127Glu + Ala133His + Val203Gly
Gly131Ser + Gly211Gln + Lys213Asp
Gly131Ser + Thr158Asp + Ala216Thr
Gly100Asn + Ser105Asp + Gln206Asn
Gly 97Glu + Gly160Gln + Thr164Asn
Ile107Cys + Lys213Asp + Ala216Pro
Trp106Gly + Gln206Asp + Ala216His
Ala133Ser + Lys213Glu + Ala216Gln
Asn 62Gln + Ile107Cys + Thr164Asp
Gly131Pro + Leu209Pro + Tyr217Ile

TABLE 23-continued

Multi-loop Triple Mutation Variants

Asn155Ser + Tyr167Ala + Phe189Gly
Asp 60Glu + Thr164Gln + Gly219Ser
Gly160Pro + Ser204Glu + Gln206Ser
Thr 66Gly + Gly100Asp + Ala216Gly
Tyr104Ile + Gly215Pro + Ala216Thr
Gly127Ser + Lys213Asp + Tyr217Ser
Ser188Glu + Gln206Asn + Leu209His
Asn 62Ser + Gln206Asn + Pro210Glu
Ala 98Glu + Leu126Met + Val203Gly
Gly154Ser + Ser161Glu + Ala216His
Pro201Gly + Gly211Glu + Ala216Thr
Ser161Asp + Gly219Gln + Thr220Asn
Asn 62Glu + Thr158Ser + Gly215Ser
Gly102Asn + Leu126Glu + Ala216Pro
Gly127Gln + Ser204Glu + Tyr217Thr
Ala133Gln + Phe189Ile + Lys213Asp
Ser130Asp + Asn212Ser + Tyr217Thr
Leu126Ile + Gly154Asn + Gln206Asp
Thr 66Pro + Gln103Asn + Lys213Asp
Leu126Asn + Gly154Gln + Pro210Gly
Leu126Val + Gly215Glu + Ala216Pro
Gln206Ser + Lys213Asp + Tyr217His
Leu 96Asn + Leu126Pro + Ala216Ser
Ser 63Asp + Trp106Asn + Gln206Asn
Gly127Ser + Ser161Glu + Gly219Asn
Val 95Thr + Thr208Gly + Lys213Glu
Gly 97Pro + Trp106Tyr + Asn218Glu
Leu 96Gln + Phe189Ile + Val203His
Ser132Asp + Ala133Pro + Tyr214Asn
Ala 98Asn + Gly127Asp + Gly211Gln
Leu 96His + Gly 97Asn + Ala216Gly
Pro210Asn + Gly215Glu + Tyr217His
Asp 60Glu + Trp106Tyr + Pro129Gln
Gly157Asn + Phe189Val + Asn218Asp
Gly100Asp + Thr164Asn + Ala200Gly
Leu126His + Gln206Asp + Ala216Ser
Ser 63Asp + Ile107Gln + Val203Ala
Ser101Glu + Gly102Gln + Val165Gln
Asp 99Glu + Thr158Ser + Gly215Gln
Ala200Ser + Ser204Glu + Tyr214Val
Asn155Gln + Thr158Glu + Phe189Asn
Thr 66Gly + Ser105Asp + Tyr214Thr
Gly102Pro + Thr164Gln + Pro210Gly
Trp106Gly + Asn155Asp + Thr220Gln
Thr158Gly + Ala187Gln + Ser204Glu
Gly154Gln + Tyr167Cys + Ser204Glu
Asp 60Glu + Ala 98His + Gly102Pro
Gly131Ser + Ile205Val + Ala216Asp
Gly128Gln + Val165Cys + Gly211Gln
Gly 97Asn + Ile107Gln + Gly166Gln
Gly160Asp + Gly166Pro + Tyr214Ile
Gln 59Asp + Gly154Ser + Asn218Gln
Gly154Ser + Val165His + Ser204Glu
Ser 63Glu + Pro129Ser + Tyr217Gly
Gly157Pro + Thr158Ser + Lys213Glu
Thr164Glu + Gly215Ser + Ala216Asn
Thr 66Pro + Asp 99Glu + Tyr217Cys
Trp106Met + Ala187Ser + Tyr217Ile
Ile107Thr + Glu156Asp + Tyr217Cys
Leu126Pro + Gly131Asn + Tyr217Leu
Tyr167His + Gly219Pro + Thr220Glu
Val 95Pro + Trp106Ile + Tyr217Gly
Val 95His + Gln206Asn + Lys213Glu
Val 95Ala + Ala187Ser + Tyr217Glu
Asp 60Glu + Asn 62Gln + Tyr167Ile
Gly160Asn + Ala187Gly + Gln206Ser
Gly102Gln + Trp106His + Ser163Glu
Asn 62Gln + Ser188Glu + Pro210Gln
Gly100Pro + Gly202Gln + Ala216Ser
Ser105Glu + Ile107Thr + Gly131Pro
Thr 66Gly + Gly131Asp + Phe189Ser
Gln103Asn + Ala187Ser + Ser204Glu
Asp 60Glu + Thr164Pro + Ala216Ser
Gln 59Glu + Asn212Ser + Tyr217Ser
Asn 61Glu + Gly166Gln + Gly215Pro
Asn 62Gln + Gly160Gln + Gly219Ser
Ser105Glu + Tyr167Ala + Tyr217Ser
Gly100Ser + Asn155Ser + Tyr217Asn
Gly 97Pro + Leu126Ala + Gly157Gln
Gly100Ser + Gly131Gln + Phe189Glu
Ser132Asp + Ala187Pro + Gln206Asn
Gln 59Asp + Gln206Asn + Tyr217Ile
Gln103Asn + Ile107Asn + Ala133Ser
Gly128Gln + Pro129Asn + Ala216Asp
Thr 66Glu + Trp106Ala + Ala187Ser
Asp 60Glu + Gly 65Asn + Tyr214Ser
Ser132Asp + Gly157Asn + Ala216Ser
Asn 62Asp + Ile205Thr + Gln206Ser
Gln 59Asn + Gly 65Pro + Val 95Asp
Val 95Ser + Gly102Ser + Lys213Asp
Ala216Pro + Tyr217Pro + Asn218Ser
Ser 63Asp + Gly127Ser + Thr220Asn
Gly 97Asn + Gly154Gln + Ala216Asn
Ala 98His + Trp106Val + Ala216Gln
Gly102Asn + Ile107Gln + Ser162Asp
Ile107Val + Lys213Glu + Ala216Ser
Tyr104Leu + Gln206Glu + Thr220Asn
Pro201Asn + Pro210Asn + Gly211Gln
Gly166Asn + Ile205Asn + Ala216Thr
Ala 98Ser + Gln206Ser + Gly215Ser
Ala133His + Ser188Asp + Tyr217Gly
Ala 98Glu + Gly131Pro + Gly157Pro
Leu 96Ile + Ser188Asp + Val203His
Tyr167Thr + Gln206Ser + Tyr217His
Leu 96Gln + Ser161Glu + Ala216Thr
Gly127Glu + Thr158Pro + Pro201Gly
Gly160Ser + Lys213Glu + Ala216Ser
Tyr104Ser + Leu126His + Tyr214His
Asn 62Ser + Gly160Glu + Ala216His
Leu 96Cys + Thr164Ser + Ser204Asp
Gly131Gln + Phe189Ile + Val203Asp
Asp 60Glu + Gly 65Gln + Thr 66Asn
Gly102Glu + Gly128Ser + Ala216Gln
Asn 62Gln + Val 95Gly + Gln206Asn
Gly 97Pro + Gly154Asp + Asn218Gln
Thr 66Pro + Leu 96Val + Ala216Pro
Gly 97Asn + Asn155Glu + Tyr214Val
Tyr104Ala + Tyr167Glu + Ala216Pro
Gly157Asn + Asn218Glu + Thr220Gly
Ala133His + Thr164Gln + Gly166Ser
Leu126Gln + Ser159Glu + Gly160Asp
Asn 61Asp + Asn 62Asp + Gly128Ser
Thr 66Pro + Gly100Glu + Ser101Glu
Ser204Glu + Ile205Gln + Ala216Glu
Ser204Asp + Ala216Glu + Tyr217Cys
Ser204Asp + Ala216Asp + Thr220Gln
Gln103Asn + Ser204Glu + Ala216Glu
Gly202Gln + Ser204Glu + Asn218Asp
Ser204Glu + Gln206Asp + Ala216Asp
Ser204Asp + Gln206Glu + Ala216Asp
Tyr167Ala + Ser204Asp + Tyr217Asp
Gly211Asp + Lys213Glu + Ala216Thr
Gly211Asp + Lys213Glu + Tyr217Pro
Tyr167Val + Gly211Asp + Lys213Glu
Asp 60Glu + Asn 62Asp + Tyr217Leu
Gly160Glu + Ser162Glu + Ala216Thr
Ser204Glu + Gln206Asp + Tyr217Leu
Ser204Glu + Gln206Asp + Ala216Thr
Ile107Cys + Ser204Glu + Gln206Glu
Ser204Glu + Gln206Glu + Gly215Asn
Ser161Asp + Ser163Asp + Ala216His
Thr164Pro + Gln206Glu + Tyr217Asp
Asp 60Glu + Gln206Asn + Pro210Asp
Asp 60Glu + Tyr104Asn + Pro210Glu
Ala187Glu + Val203Glu + Asn218Glu
Ser130Glu + Gly166Glu + Phe189Tyr
Thr158Asp + Ser162Glu + Gln206Ser
Gly154Asp + Val203Ser + Gly219Asp
Ser188Glu + Ser191Asp + Ala216Asn
Asp 60Glu + Gly 97Glu + Asp 99Glu
Thr164Pro + Ser204Glu + Gly219Glu
Asp 99Glu + Gly102Asp + Ala216Gln
Ser204Glu + Gln206Asn + Gly215Asp
Ser204Asp + Gln206Asp + Tyr214Asp

TABLE 23-continued

Multi-loop Triple Mutation Variants

Thr 66Asp + Gly211Glu + Lys213Asp
Ser101Glu + Leu126Glu + Tyr214His
Asn 61Glu + Leu 96Glu + Ile107Leu
Asp 60Glu + Leu 96Glu + Gly166Pro
Ser101Glu + Gly127Glu + Ala187Gln
Ser 63Glu + Gly131Asn + Lys213Glu
Ser 63Asp + Phe189Leu + Lys213Glu
Ser105Glu + Ser132Glu + Tyr167Gly
Ser204Asp + Ala216Glu + Thr220Glu
Ser204Glu + Lys213Asp + Gly215Asp
Asp 99Glu + Ser101Asp + Tyr104Asp
Ser 63Asp + Pro210Glu + Tyr217Glu
Thr158Gln + Gln206Asp + Lys213Asp
Gln206Glu + Lys213Glu + Ala216His
Gly157Asp + Tyr214Gly + Thr220Asp
Ser 63Glu + Gly100Ser + Tyr217Asp
Gly100Glu + Gln103Asp + Gln206Asn
Gly154Glu + Ser163Asp + Val203Met
Val 95Gly + Lys213Asp + Ala216Glu
Gln 59Asn + Leu126Glu + Pro129Glu
Ser204Glu + Gln206Asp + Lys213Asp
Ala187Asp + Ser204Glu + Gln206Glu
Ser 63Glu + Ser204Glu + Ala216Asp
Asn 61Asp + Ser 63Asp + Ala216Glu
Pro129Glu + Asn155Glu + Ser163Asp
Ser 63Asp + Ile107Leu + Asn212Asp
Gln206Asp + Pro210Asp + Asn212Asp
Glu156Asp + Ser163Glu + Gly219Asp
Ile107Glu + Gly131Ser + Ser132Asp
Gly100Asn + Gly211Asp + Gly215Glu
Gln103Asp + Gly127Glu + Ala216Gln
Ser130Asp + Gly131Asp + Lys213Glu
Gly100Asp + Ser101Glu + Ser163Asp
Pro129Asp + Ser130Asp + Tyr217Glu
Val203Asp + Ser204Glu + Lys213Glu
Ser132Asp + Ala216Glu + Tyr217Glu
Ser101Glu + Ala187Glu + Ser188Glu
Ala 98Asp + Asp 99Glu + Ser204Asp
Ser204Asp + Gln206Asp + Asn212Asp
Gln103Asp + Glu156Asp + Ser191Glu
Ser132Asp + Ser204Glu + Ala216Asp
Ala 98Glu + Ser204Glu + Ala216Glu
Ser204Asp + Lys213Asp + Asn218Glu
Ser204Glu + Gly211Asp + Tyr217Asp
Ser162Asp + Gly166Asp + Asn212Ser
Gly128Glu + Gly166Glu + Gln206Glu
Asp 60Glu + Asn 62Asp + Ser204Asp
Asp 99Glu + Ser101Asp + Gly154Glu
Gln103Ser + Gln206Glu + Gly219Asp
Phe189Asp + Pro210Asp + Lys213Glu
Asn 61Asp + Ser101Glu + Gly128Asp
Thr 66Glu + Gly166Gln + Ala216Glu
Ser101Glu + Ser204Glu + Gln206Asp
Gly157Glu + Ser204Glu + Gln206Glu
Asp 99Glu + Ser204Asp + Gln206Glu
Gly 97Glu + Ser204Glu + Gln206Glu
Ser101Asp + Gly102Ser + Ser105Asp
Ser161Glu + Ser163Asp + Gln206Asp
Ser130Asp + Ser132Glu + Asn212Glu
Ser130Glu + Ser132Glu + Gly160Asp
Pro129Glu + Gly131Glu + Gly215Glu
Asn 62Gln + Thr158Asp + Gly166Glu
Ser132Glu + Gln206Glu + Tyr217Asp
Asp 60Glu + Phe189His + Asn212Glu
Gly131Glu + Lys213Asp + Gly215Glu
Ser159Glu + Ser163Glu + Ser204Glu
Thr158Glu + Ser162Asp + Gly219Asp
Tyr104Glu + Ser132Glu + Asn212Asp
Asp 99Glu + Glu156Asp + Ser159Glu
Ser 63Glu + Ser188Asp + Ser191Asp
Ser188Asp + Ser191Glu + Ala216Asp
Gln 59Glu + Ser188Asp + Ser191Asp
Ser204Lys + Lys213Glu + Gly219Glu
Asp 60Glu + Ser204Asp + Gly219Asp
Leu126Asp + Gly166Asp + Ser204Asp
Thr164Glu + Ser188Glu + Gln206Ser
Asp 60Glu + Gln206Glu + Lys213Asp

TABLE 23-continued

Multi-loop Triple Mutation Variants

Ser105Asp + Leu126Glu + Thr220Asp
Asp 99Glu + Glu156Asp + Ser188Asp
Gln 59Glu + Asn 62Asp + Ala187Glu
Gly166Glu + Val203Asp + Gln206Glu
Asn155Glu + Ala187Glu + Lys213Asp
Thr 66Asp + Ser204Glu + Lys213Asp
Ser 63Asp + Ser188Glu + Asn218Glu
Ser 63Asp + Ser105Asp + Lys213Asp
Ser105Asp + Ser132Glu + Gln206Glu
Ser 63Asp + Gly 97Asp + Asn155Asp
Ser 63Glu + Ser101Asp + Ser105Asp
Thr164Glu + Gln206Glu + Lys213Glu
Leu126Asp + Gln206Asp + Lys213Asp
Gly131Glu + Gln206Asp + Lys213Asp
Ser 63Asp + Trp106Asp + Tyr217Glu
Gly160Glu + Lys213Glu + Ala216Glu
Ala133Glu + Lys213Asp + Ala216Asp
Ser 63Glu + Gln206Asp + Gly215Gln
Lys213Asp + Ala216Asn + Tyr217Glu
Ser130Asp + Ala187Asp + Ser204Glu
Asp 99Glu + Ser188Glu + Asn218Asp
Asn 61Asp + Ser188Glu + Asn218Asp
Gly102Asp + Ser204Glu + Thr220Glu
Gly127Asp + Ser191Glu + Lys213Asp
Thr 66Glu + Gly 97Glu + Tyr217Cys
Gly154Asp + Ala187Glu + Gly215Asp
Gly102Asp + Gly154Glu + Ser188Glu
Gln103Asp + Ser132Asp + Gln206Asp
Tyr167His + Ser191Glu + Asn218Asp
Asp 60Glu + Glu156Asp + Gly160Glu
Gln103Glu + Gly154Glu + Asn218Asp
Asp 60Glu + Asn155Glu + Ser159Asp
Gln103Glu + Ser161Glu + Ser191Asp
Ala 98Asp + Ser132Asp + Gly166Glu
Ser188Asp + Ser204Asp + Tyr214Val

TABLE 24

Multi-loop Quadruple Mutation Variants

| | | | |
|---|---|---|---|
| Gln59Ser | + Asn62Ser | + Leu96Gly | + Ser204Glu |
| Gly127Gln | + Ser188Glu | + Gly215Asn | + Ala216Pro |
| Asn62Gln | + Ile107Ala | + Gln206Asp | + Tyr217Thr |
| Asn61Ser | + Leu96His | + Gly157Pro | + Ala216Gly |
| Leu96Gln | + Gly127Gln | + Glu156Asp | + Thr220Asn |
| Thr158Glu | + Gly202Ser | + Gln206Ser | + Thr220Ser |
| Gly97Asn | + Ser105Asp | + Gly215Ser | + Ala216Ser |
| Leu126Thr | + Gly211Gln | + Lys213Asp | + Ala216Ser |
| Gly100Asp | + Trp106Asn | + Gly127Ser | + Val203Asn |
| Ile107Ala | + Gly160Asn | + Gly166Asp | + Gly202Ser |
| Ala133Thr | + Phe189Ser | + Tyr214Ile | + Ala216Glu |
| Asn62Asp | + Ser163Asp | + Phe189Ser | + Pro201Gln |
| Ala98Gln | + Gly102Asn | + Pro201Asn | + Gly219Asp |
| Thr66Ser | + Leu126Glu | + Gly127Gln | + Ala216Thr |
| Pro129Ser | + Thr164Gln | + Ala216Asp | + Tyr217Val |
| Gly128Gln | + Thr158Gln | + Gln206Asn | + Asn212Asp |
| Gly157Ser | + Gln206Glu | + Tyr217Cys | + Thr220Gly |
| Val95Gln | + Tyr104Ile | + Ser191Glu | + Gly219Ser |
| Gln59Asn | + Gly97Asn | + Gly154Pro | + Asn218Ser |
| Pro129Gly | + Thr158Asn | + Gln206Asn | + Gly211Pro |
| Ala98His | + Trp106His | + Gln206Asn | + Lys213Asp |
| Leu126Ile | + Ser204Glu | + Gln206Asn | + Tyr217Thr |
| Gln59Glu | + Asn62Gln | + Phe189Leu | + Val203Ala |
| Pro129Gln | + Gly154Pro | + Ala187Thr | + Lys213Glu |
| Ser63Glu | + Thr164Asn | + Gln206Ser | + Pro210Asn |
| Leu96Met | + Gln103Asn | + Ala133Ser | + Ser204Glu |
| Trp106Ala | + Gly154Pro | + Ala187Asn | + Gly219Pro |
| Asn62Glu | + Gly102Pro | + Gly160Asn | + Asn218Ser |
| Thr66Gly | + Gly100Asp | + Tyr104Ile | + Ala216Gly |
| Gly102Asp | + Pro201Gln | + Gly215Pro | + Ala216Thr |
| Leu126Met | + Val203Gly | + Asn212Glu | + Gly219Asn |
| Leu96Glu | + Ile107Leu | + Thr158Ser | + Gly215Ser |
| Ser130Asp | + Ala133Gln | + Asn212Ser | + Tyr217Thr |
| Thr66Gly | + Gly100Ser | + Leu126Gly | + Ala216Glu |

TABLE 24-continued

Multi-loop Quadruple Mutation Variants

| | | | | | | | |
|---|---|---|---|---|---|---|---|
| Gln103Ile | + | Tyr104Ile | + | Gly128Gln | + | Tyr217Cys |
| Leu126Pro | + | Ser204Asp | + | Gln206Asn | + | Thr208Asn |
| Pro129Ser | + | Gly157Asn | + | Thr164Glu | + | Ala200Ser |
| Gly128Gln | + | Val165Cys | + | Gly211Gln | + | Lys213Glu |
| Gly160Asn | + | Gly166Pro | + | Gly211Ser | + | Tyr214Ile |
| Gln103Ser | + | Gly166Asn | + | Gly211Ser | + | Gly215Pro |
| Asn61Asp | + | Tyr104Ser | + | Leu126His | + | Tyr214His |
| Gly65Gln | + | Gly131Gln | + | Phe189Ile | + | Val203Asp |
| Asn62Gln | + | Thr66Asp | + | Val95Gly | + | Gln206Asn |
| Thr66Pro | + | Gly97Pro | + | Gly154Asp | + | Ala216Pro |
| Val95Pro | + | Tyr104Gly | + | Gly127Ser | + | Gly215Asp |
| Asp99Glu | + | Trp106Ala | + | Pro201Gln | + | Ala216Gly |
| Asn61Gln | + | Val95Asp | + | Gly102Asn | + | Ala187Asn |
| Ile107Gln | + | Val203Ser | + | Ser204Ser | + | Gly215Ser |
| Val95Thr | + | Gly202Gln | + | Ser204Asp | + | Ala216Asn |
| Thr158Pro | + | Val203Gly | + | Lys213Glu | + | Tyr217Ser |
| Trp106Pro | + | Asn155Asp | + | Gln206Ser | + | Tyr214Ala |
| Gly102Asn | + | Gly157Ser | + | Tyr167Ala | + | Ala216Asn |
| Gly160Asn | + | Val203Thr | + | Pro210Glu | + | Asn218Gln |
| Ile107Ser | + | Gly128Asn | + | Asn155Glu | + | Ala216Gly |
| Gln103Asn | + | Pro129Gly | + | Gly166Gln | + | Thr220Gly |
| Asn61Ser | + | Ser63Asp | + | Thr66Gly | + | Gly154Asp |
| Tyr104Gly | + | Pro129Ser | + | Gln206Ser | + | Gly219Ser |
| Gly102Pro | + | Gly131Asp | + | Asn155Ser | + | Tyr217His |
| Asn61Ser | + | Val95Gln | + | Ser204Asp | + | Ala216Gln |
| Thr158Asn | + | Ala187Gly | + | Tyr217Ala | + | Gly219Asp |
| Gly65Gln | + | Gly97Pro | + | Ser130Glu | + | Pro210Asn |
| Gly128Asn | + | Ser159Glu | + | Pro201Ser | + | Tyr217Val |
| Leu126Asn | + | Asn155Gln | + | Gly202Gln | + | Asn212Ser |
| Thr66Ser | + | Tyr104Val | + | Gly154Glu | + | Gly215Asn |
| Gly102Asn | + | Gly128Gln | + | Ser161Glu | + | Tyr217Met |
| Ser132Glu | + | Thr158Gln | + | Thr164Asn | + | Gln206Asn |
| Asn62Glu | + | Leu96Ile | + | Gly211Ser | + | Gly219Ser |
| Thr208Pro | + | Pro210Gly | + | Ala216Thr | + | Tyr217Met |
| Gly100Gln | + | Gly160Asn | + | Pro201Gly | + | Asn212Asp |
| Tyr104Asp | + | Gly154Pro | + | Ala187Asn | + | Val203Ser |
| Leu96Gln | + | Leu126Thr | + | Ser162Glu | + | Tyr217Val |
| Gly128Asn | + | Ala187Pro | + | Pro201Gly | + | Ser204Glu |
| Gln103Ser | + | Gly157Glu | + | Thr158Gln | + | Ala216Gln |
| Leu126Ser | + | Thr164Glu | + | Val203Pro | + | Gly211Gln |
| Thr164Gly | + | Val203Met | + | Ala216Asp | + | Tyr217Gln |
| Ser159Asp | + | Val203Asn | + | Ile205Asn | + | Pro210Ser |
| Gly65Asn | + | Gln206Asp | + | Ala216Gly | + | Tyr217His |
| Gln103Asn | + | Ile107Cys | + | Thr164Asp | + | Val203Thr |
| Gly128Glu | + | Asn155Gln | + | Thr158Ser | + | Gly160Ser |
| Ala98His | + | Ser162Glu | + | Gln206Asn | + | Tyr217Gly |
| Gly128Ser | + | Thr164Asn | + | Ser204Glu | + | Tyr217Gly |
| Gly127Gln | + | Gly157Ser | + | Ser159Asp | + | Tyr217Val |
| Gly157Asn | + | Gln206Asn | + | Tyr217Val | + | Gly219Pro |
| Thr66Ser | + | Ala133Thr | + | Ser163Asp | + | Thr208Asn |
| Leu96Thr | + | Gly131Asp | + | Gln206Asn | + | Ala216Gly |
| Asn61Ser | + | Ser132Glu | + | Gly211Ser | + | Asn218Gln |
| Gly100Ser | + | Tyr104Ala | + | Ser204Asp | + | Gly211Gln |
| Leu96His | + | Ala98Glu | + | Pro129Gln | + | Ala133Asn |
| Asn62Glu | + | Gly128Gln | + | Ala187Asn | + | Gly215Ser |
| Leu96Ile | + | Gly157Ser | + | Val203Ala | + | Ala216Ser |
| Asn61Gln | + | Val95Thr | + | Gly160Asp | + | Ala216His |
| Leu96Cys | + | Gly128Pro | + | Ser191Glu | + | Thr208Asn |
| Trp106Ala | + | Gly131Gln | + | Val203Ala | + | Tyr214Gln |
| Asn61Ser | + | Ala216Gln | + | Tyr217Leu | + | Gly219Asn |
| Tyr104Gly | + | Ser105Glu | + | Thr158Ser | + | Leu209Thr |
| Ala133Ser | + | Phe189Thr | + | Asn212Glu | + | Tyr217Thr |
| Tyr104Ser | + | Thr158Gly | + | Thr164Glu | + | Ala216Pro |
| Gln59Asn | + | Thr66Asn | + | Thr164Gly | + | Ala187Pro |
| Ile107His | + | Gly157Ser | + | Lys213Glu | + | Tyr217Asn |
| Gly127Ser | + | Gln206Asp | + | Gly215Gln | + | Tyr217Leu |
| Leu126Gly | + | Gly131Gly | + | Tyr167Met | + | Thr220Gln |
| Thr158Gln | + | Lys213Glu | + | Gly215Ser | + | Tyr217Gly |
| Asn61Gln | + | Leu126Gly | + | Thr164Ser | + | Asn218Asp |
| Asn62Asp | + | Pro129Gly | + | Gln206Ser | + | Ala216His |
| Asp60Glu | + | Val95Asn | + | Leu126Pro | + | Val203Thr |
| Gln103Glu | + | Ile107Val | + | Phe189Asn | + | Ala216Thr |
| Ile107Thr | + | Pro129Gln | + | Lys213Glu | + | Tyr217Thr |
| Tyr104His | + | Gly154Gln | + | Gly157Asp | + | Tyr217Ser |
| Gln59Asn | + | Trp106Cys | + | Ala200Thr | + | Ala216Gln |
| Thr66Gln | + | Gly97Ser | + | Gly127Pro | + | Tyr217Asp |
| Gly100Asn | + | Ser204Asp | + | Pro210Ser | + | Tyr214Gly |
| Asn62Ser | + | Ile107Gly | + | Leu126Cys | + | Thr220Gly |
| Leu126His | + | Gly154Asp | + | Asn218Gln | + | Thr220Asn |
| Ser101Glu | + | Gly157Gln | + | Tyr214Pro | + | Ala216His |
| Asn62Gln | + | Ser162Glu | + | Val203Ser | + | Ala216Thr |
| Tyr104Gln | + | Trp106Gly | + | Leu126Asp | + | Asn212Gln |
| Gln59Ser | + | Val95Pro | + | Gly202Asn | + | Tyr217Ser |
| Leu96Pro | + | Gly160Asp | + | Ser161Glu | + | Gly166Asn |
| Ser159Glu | + | Gly160Asp | + | Tyr167Gly | + | Phe189Val |
| Asn212Glu | + | Lys213Glu | + | Ala216Ser | + | Tyr217Gln |
| Thr158Asp | + | Ser159Asp | + | Gly215Asn | + | Ala216Thr |
| Ala98Asp | + | Asp99Glu | + | Thr164Gln | + | Ala187Ser |
| Gly97Pro | + | Gly131Pro | + | Gly154Asp | + | Asn155Asp |
| Gly102Ser | + | Trp106Gln | + | Gly157Glu | + | Phe189Asp |
| Gly100Gln | + | Ser204Glu | + | Tyr214Ile | + | Ala216Glu |
| Val95Pro | + | Ser204Glu | + | Ala216Gly | + | Asn218Glu |
| Ser204Glu | + | Ile205Gln | + | Pro210Gly | + | Asn218Asp |
| Gly97Ser | + | Gly154Asn | + | Gln206Asp | + | Gly215Asp |
| Gly97Asp | + | Ala98Gln | + | Asp99Glu | + | Gly154Ser |
| Thr158Gln | + | Val165Met | + | Gly211Glu | + | Lys213Glu |
| Gly160Glu | + | Ser162Asp | + | Tyr167Ile | + | Gly219Ser |
| Asn61Ser | + | Thr66Ser | + | Asn155Glu | + | Gly157Asp |
| Thr158Asp | + | Ser159Asp | + | Thr164Asp | + | Gly211Asn |
| Val95Asp | + | Gly102Glu | + | Ala187Pro | + | Tyr217Pro |
| Asn62Glu | + | Gly100Asp | + | Thr208Asn | + | Tyr217His |
| Ser204Asp | + | Gln206Glu | + | Gly211Gln | + | Ala216His |
| Gly154Asn | + | Ser204Glu | + | Gln206Asp | + | Tyr217Thr |
| Thr66Gln | + | Ser130Glu | + | Ser132Asp | + | Thr158Pro |
| Asp60Glu | + | Gly65Asn | + | Thr66Glu | + | Tyr214Ser |
| Asp60Glu | + | Gln206Ser | + | Pro210Glu | + | Gly219Ser |
| Thr158Asp | + | Ser163Glu | + | Ser191Glu | + | Ile205Gly |
| Ser204Asp | + | Gly215Glu | + | Ala216Glu | + | Gly219Asp |
| Thr158Asp | + | Ala187Asp | + | Phe189Glu | + | Tyr217Met |
| Gly128Gln | + | Pro129Asn | + | Val203Asp | + | Ala216Asp |
| Gly97Asn | + | Ile107Gln | + | Ser204Glu | + | Gly219Glu |
| Trp106Asn | + | Gly157Gln | + | Ser204Asp | + | Gly219Asp |
| Gly127Asp | + | Gly128Asn | + | Ser130Asp | + | Gly219Gln |
| Val95Ser | + | Pro129Gly | + | Asn155Glu | + | Ser188Glu |
| Asn155Asp | + | Ser188Asp | + | Phe189Asn | + | Ala216Gly |
| Trp106Phe | + | Ser204Asp | + | Gln206Asp | + | Tyr214Asp |
| Asn62Asp | + | Gly97Gln | + | Pro210Asp | + | Gly211Glu |
| Val95Asp | + | Tyr104Asp | + | Leu126Ser | + | Asn155Gln |
| Gly100Asn | + | Gln206Asp | + | Lys213Glu | + | Ala216Asp |
| Gln206Asp | + | Lys213Glu | + | Ala216Glu | + | Tyr217Asn |
| Gly102Gln | + | Asn155Glu | + | Val203Glu | + | Asn218Asp |
| Gln59Glu | + | Thr66Glu | + | Gly102Pro | + | Gly166Gln |
| Leu126Cys | + | Gly157Asp | + | Ser163Asp | + | Ala216His |
| Thr66Asp | + | Gln206Asp | + | Ala216Asp | + | Gly219Pro |
| Asn62Asp | + | Ser63Glu | + | Gly131Asn | + | Lys213Glu |
| Leu126Asn | + | Pro129Asn | + | Ser191Asp | + | Gly219Glu |
| Thr66Asn | + | Gly100Asn | + | Gly127Ser | + | Lys213Glu |
| Ile107Val | + | Phe189Asp | + | Val203Glu | + | Ala216Gln |
| Ser63Asp | + | Val95Ser | + | Lys213Asp | + | Ala216Ser |
| Ile107His | + | Val203Cys | + | Tyr214Glu | + | Tyr217Asp |
| Asn62Ser | + | Ser105Asp | + | Trp106Gly | + | Ser132Asp |
| Ser63Glu | + | Leu96Cys | + | Pro210Glu | + | Ala216Glu |
| Ala187Gly | + | Gly215Glu | + | Tyr217Thr | + | Asn218Glu |
| Gly160Ser | + | Gln206Glu | + | Lys213Glu | + | Ala216Ser |
| Gly131Pro | + | Phe189Leu | + | Gln206Glu | + | Lys213Glu |
| Pro129Asn | + | Ala133Gln | + | Gln206Glu | + | Lys213Glu |
| Ala98His | + | Gly154Glu | + | Ser163Asp | + | Tyr217Met |
| Val203His | + | Gln206Glu | + | Gly211Glu | + | Lys213Asp |
| Leu126Ala | + | Ser204Glu | + | Gln206Asp | + | Lys213Glu |
| Ile107Leu | + | Gly157Asp | + | Val203His | + | Gly219Glu |
| Ala98Glu | + | Gly102Asp | + | Ser105Glu | + | Leu209Thr |
| Thr66Gln | + | Lys213Glu | + | Ala216Glu | + | Asn218Glu |
| Ser204Glu | + | Gln206Asn | + | Pro210Glu | + | Gly215Asp |
| Gly127Asp | + | Ser132Asp | + | Gly154Asp | + | Val165Gln |
| Ser63Glu | + | Val203His | + | Asn212Glu | + | Tyr217Leu |
| Gln206Glu | + | Lys213Glu | + | Tyr217Ala | + | Asn218Glu |
| Gln206Asp | + | Lys213Glu | + | Ala216Asn | + | Asn218Asp |
| Gly157Pro | + | Ser188Glu | + | Ser204Glu | + | Ala216Asp |
| Gln59Glu | + | Thr66Asp | + | Gly100Gln | + | Gly215Glu |
| Trp106Ser | + | Ala187Asp | + | Gln206Asn | + | Tyr217Asp |
| Ser159Glu | + | Asn212Gln | + | Gly215Asp | + | Ala216Glu |
| Gly160Asp | + | Ser161Asp | + | Gln206Asp | + | Tyr214Asn |
| Thr66Glu | + | Tyr167Gln | + | Gln206Asp | + | Gly211Pro |
| Pro129Asn | + | Ser163Glu | + | Tyr217Glu | + | Asn218Glu |

TABLE 24-continued

Multi-loop Quadruple Mutation Variants

| | | | |
|---|---|---|---|
| Asn155Glu | + Glu156Asp | + Ser204Glu | + Tyr214Thr |
| Gln59Asp | + Ser162Asp | + Ser163Glu | + Ala216Thr |
| Leu126Pro | + Ser162Glu | + Ser163Glu | + Tyr217Glu |
| Gly100Glu | + Val203Cys | + Asn212Asp | + Lys213Glu |
| Ser105Glu | + Ala187Ser | + Val203Glu | + Ser204Asp |
| Gln103Asp | + Ser163Glu | + Thr164Glu | + Pro201Gln |
| Val95Gln | + Glu156Asp | + Gly157Asp | + Lys213Glu |
| Ser162Glu | + Thr164Gln | + Ala216Asp | + Tyr217Glu |
| Asp99Glu | + Gly100Glu | + Ser159Glu | + Ala216Thr |
| Ala98Glu | + Asp99Glu | + Trp106Gly | + Gly154Asp |
| Asn62Glu | + Ser63Glu | + Pro129Ser | + Asn155Asp |
| Asn61Glu | + Gln206Glu | + Ala216Glu | + Tyr217Cys |
| Thr66Pro | + Gln103Asp | + Glu156Glu | + Ser191Asp |
| Asp60Glu | + Ser204Asp | + Ala216Asp | + Tyr217Ile |
| Ser105Asp | + Ser204Asp | + Gln206Ser | + Ala216Glu |
| Thr158Asn | + Ser162Asp | + Ser204Asp | + Asn218Asp |
| Gln59Asp | + Gly157Ser | + Ser204Asp | + Asn218Asp |
| Gly97Ser | + Gly128Glu | + Gln206Glu | + Gly215Asp |
| Trp106Asp | + Val203Cys | + Ser204Glu | + Tyr217Glu |
| Ser105Glu | + Ala187Thr | + Ser204Glu | + Tyr217Glu |
| Gly97Asn | + Asn155Glu | + Ser163Glu | + Tyr214Val |
| Val95Asp | + Trp106Glu | + Ala187Pro | + Val203Asp |
| Gln103Asp | + Trp106Glu | + Gly128Asn | + Ser162Asp |
| Gly128Glu | + Ser130Asp | + Ser188Glu | + Ala216Gln |
| Gln103Asp | + Ser105Glu | + Gly154Glu | + Ala216Thr |
| Ser159Glu | + Gly211Asp | + Lys213Asp | + Tyr217Glu |
| Gln59Asn | + Ser188Asp | + Gly211Glu | + Lys213Glu |
| Ile107Glu | + Gly211Glu | + Lys213Asp | + Tyr217Gln |
| Ser159Asp | + Ser162Glu | + Pro210Glu | + Ala216Asn |
| Asp60Glu | + Asn62Asp | + Ser191Asp | + Tyr217Leu |
| Asp60Glu | + Ser63Asp | + Ile107Asn | + Phe189Glu |
| Leu96Cys | + Gly166Asp | + Pro210Asp | + Lys213Asp |
| Val95Glu | + Ala98Asn | + Gly102Glu | + Ser162Glu |
| Ser63Asp | + Tyr167His | + Ala216Glu | + Gly219Glu |
| Tyr104Asp | + Thr158Asp | + Ser191Glu | + Asn218Ser |
| Gly154Pro | + Ser159Glu | + Ser204Asp | + Gln206Asp |
| Gly102Glu | + Ser204Asp | + Gln206Glu | + Tyr217His |
| Asn155Gln | + Ser163Asp | + Ser204Asp | + Gln206Glu |
| Gly131Asp | + Thr158Gln | + Ser204Asp | + Gln206Asp |
| Tyr167Asp | + Ser204Glu | + Gln206Glu | + Tyr217Asn |
| Gly97Asp | + Ala133Gly | + Ser204Asp | + Gln206Asp |
| Gly127Asp | + Ser204Asp | + Gln206Glu | + Tyr214Asn |
| Gly102Glu | + Gly127Gln | + Asn155Asp | + Thr220Asp |
| Gly97Glu | + Ser130Glu | + Tyr167Asp | + Tyr217Val |
| Asn62Glu | + Ala187Gly | + Pro210Asp | + Ala216Glu |
| Ser101Asp | + Ser105Asp | + Ala216His | + Tyr217His |
| Ser130Asp | + Ser132Glu | + Asn212Glu | + Ala216Gln |
| Ser130Glu | + Ser132Glu | + Gly160Asp | + Thr220Gly |
| Gly100Glu | + Tyr104Thr | + Ser130Asp | + Ser132Asp |
| Gln59Ser | + Gly160Asp | + Gln206Glu | + Tyr217Asp |
| Gly127Asp | + Pro129Glu | + Ser188Asp | + Gln206Asn |
| Ser159Asp | + Thr164Glu | + Phe189His | + Lys213Glu |
| Asn61Asp | + Gly97Asp | + Ser159Glu | + Thr220Ser |
| Ser159Glu | + Ser163Glu | + Ser204Glu | + Tyr217Ser |
| Thr158Asp | + Ser162Glu | + Ala187Pro | + Ala216Glu |
| Leu96Val | + Thr158Glu | + Ser162Asp | + Gly219Asp |
| Asp99Glu | + Thr158Asp | + Ser162Asp | + Val203Met |
| Val95Asp | + Gly131Asn | + Ser163Asp | + Ser191Glu |
| Asn61Glu | + Asp99Glu | + Ser204Asp | + Tyr217Gly |
| Asn62Asp | + Gly166Ser | + Ser204Asp | + Gly215Asp |
| Gly102Asp | + Ser105Asp | + Tyr167Ala | + Gly211Glu |
| Ser188Asp | + Ser191Glu | + Ala216Gly | + Tyr217Glu |
| Asp60Glu | + Gly97Asp | + Trp106Asn | + Ser159Glu |
| Thr66Asp | + Leu96Glu | + Phe189Gly | + Gly215Asp |
| Asn62Asp | + Thr66Asp | + Tyr104Pro | + Gly166Asp |
| Asn61Ser | + Ala98Asp | + Asn155Asp | + Ser188Glu |
| Gly100Glu | + Tyr104Glu | + Ser130Asp | + Asn155Gln |
| Asp60Glu | + Leu126Asn | + Gln206Glu | + Lys213Asp |
| Ala98Glu | + Gly154Pro | + Glu156Asp | + Ser188Glu |
| Gly128Gln | + Ala133Glu | + Ala187Glu | + Ser191Asp |
| Ser101Glu | + Gly154Asp | + Gly211Glu | + Tyr214Glu |
| Ser132Glu | + Asn155Asp | + Thr158Gln | + Ala216Thr |
| Asn61Glu | + Asn155Asp | + Ala187Asp | + Asn212Gln |
| Gln103Glu | + Gly160Asn | + Gln206Asp | + Asn218Glu |
| Gln59Glu | + Gly100Glu | + Thr164Pro | + Gly211Asp |
| Ser63Glu | + Ser101Asp | + Gly131Ser | + Val203Pro |
| Gln59Asp | + Thr66Asp | + Tyr104Val | + Ala133Asp |
| Ser63Glu | + Ser101Glu | + Ala133His | + Ala216Glu |
| Asp60Glu | + Val95Ala | + Lys213Glu | + Tyr217Ala |
| Trp106Met | + Ser191Glu | + Lys213Glu | + Gly219Glu |
| Ser63Asp | + Gly160Asp | + Lys213Asp | + Ala216His |
| Gly102Asp | + Gly157Asn | + Ser162Glu | + Ser191Glu |
| Gln59Ser | + Ser105Asp | + Ser162Asp | + Ser191Asp |
| Gly127Pro | + Ser162Glu | + Ser191Glu | + Asn212Asp |
| Ser63Asp | + Ser105Asp | + Ser132Asp | + Ala216His |
| Thr66Glu | + Gly128Gln | + Glu156Asp | + Ala216Asp |
| Gly128Asp | + Gly157Asn | + Pro210Gln | + Thr220Glu |
| Glu156Asp | + Gln206Glu | + Lys213Glu | + Ala216Asn |
| Asp99Glu | + Gly157Pro | + Gln206Asp | + Lys213Glu |
| Ser163Asp | + Gln206Asp | + Lys213Glu | + Tyr217Ala |
| Gly154Glu | + Ser163Glu | + Pro210Gln | + Tyr217Asp |
| Gly154Asp | + Gly157Asn | + Ser163Asp | + Ser204Glu |
| Gly154Ser | + Gly157Asp | + Lys213Glu | + Ala216Glu |
| Gly157Ser | + Thr158Glu | + Lys213Asp | + Ala216Glu |
| Ser101Glu | + Gly154Pro | + Lys213Asp | + Ala216Glu |
| Gly100Asp | + Lys213Glu | + Ala216Asp | + Tyr217Leu |
| Asn62Ser | + Thr158Glu | + Ser204Asp | + Thr220Asp |
| Thr66Asn | + Ile107Val | + Lys213Asp | + Tyr217Asp |
| Gly157Asn | + Pro201Gln | + Lys213Asp | + Tyr217Asp |
| Gly127Glu | + Thr158Pro | + Ala187Asp | + Ser204Glu |
| Asp99Glu | + Ala133Gly | + Ser188Glu | + Thr220Glu |
| Asp60Glu | + Ser188Glu | + Gln206Ser | + Asn218Glu |
| Gln59Asp | + Leu96Glu | + Gly131Gln | + Ser132Asp |
| Ser101Glu | + Pro129Asp | + Thr158Asn | + Val203Ser |
| Ser63Glu | + Ser163Asp | + Ala216Glu | + Tyr217Gln |
| Gly102Gln | + Gly160Glu | + Ser191Glu | + Lys213Glu |
| Val95Glu | + Asp99Glu | + Gly215Glu | + Asn218Gln |
| Ser105Glu | + Ala133Glu | + Val203Glu | + Asn218Gln |
| Gln103Asp | + Ser132Asp | + Ser162Glu | + Gln206Ser |
| Asp60Glu | + Ser101Asp | + Thr164Gly | + Lys213Asp |
| Gln59Asp | + Asp99Glu | + Gln103Asn | + Ala187Pro |
| Asp60Glu | + Ser159Asp | + Tyr167Leu | + Ser188Asp |
| Asn62Glu | + Ser163Asp | + Gly211Glu | + Ala216His |
| Asn62Glu | + Ser132Asp | + Pro210Gly | + Gly211Glu |
| Gly102Asn | + Ser162Asp | + Gln206Asp | + Gly219Asp |
| Ser188Asp | + Ser204Asp | + Tyr217Leu | + Thr220Gln |
| Ser63Glu | + Gly166Gln | + Ala216Thr | + Asn218Glu |
| Gln103Glu | + Gly131Glu | + Tyr217Thr | + Thr220Glu |
| Asp60Glu | + Phe189His | + Asn212Glu | + Ala216Asp |
| Asn155Gln | + Gly215Glu | + Tyr217Pro | + Gly219Asp |
| Gly102Asn | + Leu126Glu | + Ser130Glu | + Lys213Asp |
| Ala98Asp | + Gly166Glu | + Pro210Asp | + Tyr214Gln |
| Asn62Glu | + Asn155Ser | + Lys213Asp | + Tyr217Leu |
| Asp60Glu | + Ser105Asp | + Lys213Glu | + Thr220Gln |
| Asp60Glu | + Gln206Ser | + Lys213Glu | + Asn218Asp |
| Ser63Glu | + Gly97Gln | + Gln103Asp | + Gln206Asp |
| Ser63Glu | + Val95Ala | + Ser130Asp | + Gln206Asp |
| Ser63Glu | + Ile107Met | + Ser191Asp | + Gln206Asp |
| Pro129Asn | + Ser130Asp | + Lys213Glu | + Tyr217Glu |
| Pro129Asn | + Ser191Glu | + Lys213Asp | + Tyr217Glu |
| Gly97Gln | + Gly102Asp | + Pro129Glu | + Phe189Gln |
| Gln59Asn | + Ser162Glu | + Phe189Asp | + Ser204Asp |
| Gly127Pro | + Gly128Glu | + Phe189Glu | + Ser204Asp |
| Leu96Pro | + Ser105Asp | + Ser130Glu | + Ala133Gly |
| Tyr167His | + Ser191Glu | + Asn212Glu | + Asn218Asp |
| Asn61Glu | + Thr158Gln | + Lys213Asp | + Tyr217Asn |
| Gln59Asp | + Gly157Asp | + Gln206Ser | + Asn218Asp |
| Gly154Ser | + Ser163Glu | + Ser188Glu | + Ser204Asp |
| Leu96Asn | + Ser130Asp | + Ser188Asp | + Ser204Glu |
| Ile107Asp | + Ser188Asp | + Ser204Asp | + Gln206Asn |
| Gln206Glu | + Ala216Gly | + Tyr217Leu | + Thr220Asp |
| Gly102Glu | + Leu126Cys | + Ser130Glu | + Tyr214Asp |
| Asn62Glu | + Gly160Asp | + Lys213Glu | + Ala216Gly |
| Ser101Asp | + Trp106Met | + Gly154Asp | + Ser162Asp |
| Asp60Glu | + Gly102Asp | + Gln206Asn | + Ala216Asp |
| Glu156Asp | + Gln206Ser | + Pro210Asp | + Tyr217Asp |
| Pro129Glu | + Ser159Asp | + Gln206Glu | + Tyr217Pro |
| Pro129Asp | + Ser159Glu | + Lys213Asp | + Tyr217His |
| Ser105Asp | + Trp106Leu | + Gly127Glu | + Ser163Glu |
| Ser101Asp | + Ala133Glu | + Ser191Asp | + Val203Asp |
| Ser63Glu | + Ser130Asp | + Tyr217Gln | + Gly219Asp |
| Gly131Asp | + Ser163Asp | + Gly166Asn | + Ser204Asp |
| Ile107Asp | + Gln206Ser | + Asn212Glu | + Ala216Asp |
| Leu126Gly | + Ser130Asp | + Gly154Asn | + Asn218Asp |

TABLE 24-continued

Multi-loop Quadruple Mutation Variants

| | | | | | | |
|---|---|---|---|---|---|---|
| Gln59Asp | + | Ser105Asp | + | Gly166Gln | + | Ser204Asp |
| Asn61Asp | + | Ser105Glu | + | Ala187Gln | + | Ala216Gly |
| Ser105Asp | + | Phe189Ile | + | Lys213Glu | + | Gly219Gln |
| Ser63Glu | + | Gly131Gln | + | Ser204Glu | + | Gly219Asn |
| Gly157Pro | + | Thr164Glu | + | Gln206Asn | + | Lys213Asp |
| Leu96Ile | + | Ser101Asp | + | Gln206Glu | + | Tyr214Ala |
| Thr66Gln | + | Leu96Met | + | Tyr167Glu | + | Ser188Glu |
| Tyr104Cys | + | Gly160Asp | + | Ile205Pro | + | Ala216Glu |
| Asp60Glu | + | Ser130Asp | + | Pro201Gln | + | Ala216Gly |
| Ile107Asp | + | Ser191Asp | + | Gln206Asp | + | Ala216Thr |
| Gln59Asp | + | Val95Asn | + | Ser101Glu | + | Ser163Glu |
| Val95Gln | + | Tyr104Cys | + | Lys213Glu | + | Asn218Asp |
| Asn62Asp | + | Gly97Asn | + | Ala98Ser | + | Ser162Glu |
| Gln103Glu | + | Ser204Asp | + | Gln206Asn | + | Ala216Pro |
| Ser101Asp | + | Ser162Asp | + | Gly166Ser | + | Tyr217Thr |
| Leu126Ile | + | Gly128Asp | + | Pro210Ser | + | Asn218Glu |
| Gly100Glu | + | Gly160Ser | + | Gly166Glu | + | Ala216Thr |
| Gln103Asn | + | Ser132Asp | + | Ser163Glu | + | Ser188Asp |

TABLE 25

Multi-loop Quintuples Mutation Variants

| | | | | | | | | |
|---|---|---|---|---|---|---|---|---|
| Val95Gln | + | Tyr104Cys | + | Gly127Gln | + | Lys213Glu | + | Ala216Pro |
| Asn61Ser | + | Leu96His | + | Gly157Pro | + | Val203Asp | + | Ala216Gly |
| Leu96Gln | + | Gly127Gln | + | Glu156Asp | + | Tyr214Ala | + | Thr220Asn |
| Gly100Gln | + | Tyr167Cys | + | Ser188Glu | + | Val203Gln | + | Ala216His |
| Asn62Ser | + | Trp106Gly | + | Ser132Asp | + | Ala187Ser | + | Phe189Ser |
| Thr66Ser | + | Gly127Gln | + | Pro201Asn | + | Ala216Thr | + | Gly219Asp |
| Gly97Asn | + | Gly154Pro | + | Gln206Asn | + | Pro210Glu | + | Gly211Pro |
| Pro129Gly | + | Ser132Glu | + | Thr158Asn | + | Val165Thr | + | Gln206Asn |
| Gly65Ser | + | Gly97Gln | + | Gly128Ser | + | Lys213Asp | + | Gly219Gln |
| Leu96Met | + | Gln103Asn | + | Ala133Ser | + | Gly154Pro | + | Gly219Pro |
| Asn61Gln | + | Trp106Ala | + | Gly211Pro | + | Asn218Asp | + | Gly219Asn |
| Thr66Gly | + | Tyr104Ile | + | Gly211Glu | + | Gly215Pro | + | Ala216Gly |
| Leu126Ile | + | Ser130Asp | + | Gly154Asn | + | Asn212Ser | + | Tyr217Thr |
| Leu126Val | + | Gln206Ser | + | Pro210Gly | + | Gly215Glu | + | Ala216Pro |
| Leu96Asn | + | Leu126Pro | + | Lys213Asp | + | Ala216Ser | + | Tyr217His |
| Trp106Asn | + | Gly127Ser | + | Ser161Glu | + | Gln206Asn | + | Gly219Asn |
| Ser101Glu | + | Gly102Gln | + | Ile107Gln | + | Val165Gln | + | Val203Ala |
| Asp60Glu | + | Ala98Gly | + | Ile107Ser | + | Gly157Ser | + | Thr164Ser |
| Pro129Glu | + | Gly160Pro | + | Gly166Asn | + | Ala187Pro | + | Gly202Ser |
| Leu96Ile | + | Tyr167Thr | + | Ser188Asp | + | Val203His | + | Gln206Ser |
| Asn61Gln | + | Val95Asp | + | Gly102Asn | + | Gly131Asn | + | Ala187Asn |
| Gly160Asn | + | Val203Thr | + | Pro210Glu | + | Asn218Gln | + | Thr220Gln |
| Gly128Asn | + | Asn155Glu | + | Gly166Gln | + | Ala216Gly | + | Thr220Gly |
| Gly65Ser | + | Val95Met | + | Gly100Asn | + | Gly131Asp | + | Tyr214Gly |
| Tyr104Gly | + | Pro129Ser | + | Ser163Glu | + | Gln206Ser | + | Gly219Ser |
| Asn61Ser | + | Val95Gln | + | Ser204Asp | + | Pro210Gly | + | Ala216Gln |
| Gly65Gln | + | Gly97Pro | + | Ser130Glu | + | Gly154Ser | + | Pro210Asn |
| Trp106Ser | + | Gly128Asn | + | Ser159Glu | + | Pro201Ser | + | Tyr217Val |
| Leu96Met | + | Leu126Asn | + | Asn155Gln | + | Ser188Glu | + | Gly202Gln |
| Gly100Glu | + | Thr158Gln | + | Thr164Asn | + | Gln206Asn | + | Ala216Thr |
| Asn62Glu | + | Leu96Ile | + | Gly97Ser | + | Gly211Ser | + | Gly219Ser |
| Gly102Asp | + | Tyr167Ala | + | Pro210Gly | + | Ala216Thr | + | Tyr217Met |
| Ser132Glu | + | Thr158Pro | + | Phe189Thr | + | Ala200Gln | + | Tyr214Ala |
| Ala98Pro | + | Trp106Pro | + | Gly160Pro | + | Ala216Asn | + | Tyr217Asp |
| Gly127Pro | + | Ala133Asn | + | Thr164Glu | + | Gly211Gln | + | Tyr214Thr |
| Gly100Asn | + | Trp106Pro | + | Gly127Ser | + | Lys213Glu | + | Tyr214Ala |
| Gly157Asn | + | Ser204Asp | + | Gln206Asn | + | Tyr217Val | + | Gly219Pro |
| Leu96Thr | + | Gly131Asp | + | Ala133Thr | + | Gln206Asn | + | Ala216Gly |
| Gly100Ser | + | Tyr104Ala | + | Thr164Asp | + | Gly211Gln | + | Thr220Ser |
| Ser101Asp | + | Pro129Ser | + | Phe189Val | + | Pro201Asn | + | Ala216Ser |
| Thr66Gly | + | Gly102Asn | + | Tyr104His | + | Trp106Thr | + | Ala187Asn |
| Thr66Asn | + | Gly102Glu | + | Trp106Gly | + | Gly166Ser | + | Ala216Thr |
| Gly128Gln | + | Gly154Asn | + | Tyr167Gly | + | Tyr217Leu | + | Asn218Glu |
| Ala133Ser | + | Gly157Ser | + | Phe189Thr | + | Gly202Asn | + | Asn212Glu |
| Tyr104Ser | + | Thr158Gly | + | Thr164Glu | + | Gln206Asn | + | Ala216Pro |
| Gln59Asn | + | Gln103Asn | + | Thr164Gly | + | Ala187Pro | + | Thr220Asp |
| Gly97Gln | + | Gly102Asp | + | Gly127Ser | + | Phe189Gln | + | Tyr217Leu |
| Thr66Asn | + | Gln206Glu | + | Tyr214Ile | + | Ala216Thr | + | Tyr217Cys |
| Asp60Glu | + | Thr66Gly | + | Leu96Gly | + | Ala216His | + | Tyr217Asn |
| Ile107Asp | + | Gly160Asn | + | Val203Pro | + | Gly211Pro | + | Gly219Asn |
| Val95Ser | + | Trp106Cys | + | Val165Gln | + | Pro210Gln | + | Tyr217Glu |
| Trp106Thr | + | Thr158Ser | + | Thr164Pro | + | Ser204Glu | + | Thr220Pro |
| Gly128Pro | + | Ala187Ser | + | Gln206Asn | + | Asn212Ser | + | Gly215Asp |
| Trp106Gln | + | Leu126Gly | + | Thr164Ser | + | Val203Gln | + | Asn218Asp |

TABLE 25-continued

Multi-loop Quintuples Mutation Variants

| | | | | | | | | |
|---|---|---|---|---|---|---|---|---|
| Asp60Glu | + | Val95Gln | + | Leu126Pro | + | Gly157Asn | + | Val203Thr |
| Gln59Asn | + | Trp106Cys | + | Ala200Thr | + | Gly211Gln | + | Ala216Gln |
| Asn62Ser | + | Ile107Gly | + | Leu126Cys | + | Pro210Glu | + | Thr220Gly |
| Asn62Gln | + | Thr158Glu | + | Val203Ser | + | Gly215Ser | + | Ala216Thr |
| Gln59Asn | + | Asp60Glu | + | Trp106Phe | + | Gly154Gln | + | Thr208Pro |
| Thr66Ser | + | Asn155Gln | + | Val203Gln | + | Gln206Glu | + | Tyr217His |
| Gly128Pro | + | Phe189Met | + | Val203Gly | + | Ser204Glu | + | Ala216Glu |
| Gln59Ser | + | Asn62Ser | + | Leu96Gly | + | Ser204Glu | + | Asn218Asp |
| Gln103Ser | + | Gly128Gln | + | Ser204Glu | + | Gly211Asn | + | Asn218Glu |
| Gly97Pro | + | Pro129Gln | + | Gly157Asn | + | Ser204Asp | + | Asn218Glu |
| Leu126Asn | + | Thr158Gln | + | Val165Met | + | Gly211Glu | + | Lys213Glu |
| Gly157Ser | + | Ser204Glu | + | Gln206Asp | + | Tyr217Cys | + | Thr220Gly |
| Ala133Thr | + | Phe189Ser | + | Ser204Asp | + | Gln206Asp | + | Tyr214Ile |
| Gly100Gln | + | Gly154Asn | + | Ser204Glu | + | Gln206Asp | + | Tyr217Thr |
| Gly127Asp | + | Gly128Glu | + | Gly154Glu | + | Gly157Asn | + | Phe189Ser |
| Gly100Gln | + | Trp106Thr | + | Ser130Asp | + | Tyr167Glu | + | Tyr217Thr |
| Glu156Asp | + | Thr158Asp | + | Tyr167Gly | + | Pro201Gln | + | Gly215Ser |
| Gly157Gln | + | Val203Asp | + | Ser204Asp | + | Ala216Pro | + | Gly219Asp |
| Leu126Gly | + | Pro129Glu | + | Gly131Glu | + | Tyr167Met | + | Thr220Gln |
| Leu96Ser | + | Ser130Asp | + | Gly166Glu | + | Ala216Gln | + | Tyr217Ile |
| Asn155Glu | + | Gly160Asn | + | Gly166Glu | + | Tyr217Cys | + | Thr220Asp |
| Asn62Asp | + | Gly97Gln | + | Trp106Gly | + | Pro210Asp | + | Asn212Gln |
| Val95Asp | + | Tyr104Glu | + | Leu126Ser | + | Asn155Gln | + | Gln206Ser |
| Gly154Glu | + | Thr158Asp | + | Phe189Glu | + | Gly215Asn | + | Tyr217Met |
| Ile107Leu | + | Gly154Asp | + | Gly157Glu | + | Val203His | + | Gly219Glu |
| Trp106Ile | + | Asn155Ser | + | Ser159Asp | + | Ser191Glu | + | Ala216Thr |
| Gly100Asp | + | Leu126Asp | + | Gly127Ser | + | Pro129Gln | + | Thr220Ser |
| Ala133Pro | + | Gln206Glu | + | Tyr214Ala | + | Asn218Glu | + | Gly219Ser |
| Thr66Gly | + | Ser101Glu | + | Gly102Asn | + | Leu126Glu | + | Ala216Pro |
| Gly100Gln | + | Gly102Glu | + | Tyr104Glu | + | Asn155Gln | + | Val203Ala |
| Leu126His | + | Ala187Glu | + | Val203Glu | + | Gln206Asp | + | Asn218Glu |
| Asp60Glu | + | Leu96Asn | + | Pro129Gln | + | Gly211Glu | + | Tyr217Met |
| Leu96Cys | + | Ile107Ala | + | Ala133Pro | + | Gly157Asp | + | Gly160Asp |
| Ser63Asp | + | Thr158Gly | + | Gln206Asp | + | Tyr214Asp | + | Tyr217Asp |
| Gln59Asp | + | Asn62Asp | + | Gly100Glu | + | Phe189Tyr | + | Tyr214Met |
| Ser101Glu | + | Gly127Glu | + | Ala187Gln | + | Gln206Asn | + | Tyr217Ile |
| Asn62Asp | + | Ser63Glu | + | Gly100Asp | + | Gly131Asn | + | Lys213Glu |
| Asp60Glu | + | Gly97Asp | + | Ala98Glu | + | Phe189His | + | Gly211Glu |
| Asp60Glu | + | Val95Glu | + | Asp99Glu | + | Ser101Asp | + | Val165Thr |
| Gly102Gln | + | Gly154Glu | + | Asn155Glu | + | Ser191Asp | + | Gln206Asp |
| Asn61Ser | + | Thr66Ser | + | Leu126Glu | + | Asn155Glu | + | Gly157Asp |
| Pro129Asn | + | Ala133Gln | + | Phe189Ile | + | Gln206Glu | + | Lys213Glu |
| Asn61Ser | + | Gln206Asp | + | Lys213Glu | + | Tyr217Ala | + | Gly219Asn |
| Gln59Asn | + | Gly128Asn | + | Ala200Thr | + | Gln206Glu | + | Lys213Glu |
| Phe189Gln | + | Val203Gly | + | Gln206Asp | + | Lys213Asp | + | Tyr217Pro |
| Ala98His | + | Gly154Glu | + | Ser163Asp | + | Val203Met | + | Tyr217Met |
| Leu96Met | + | Pro129Gly | + | Gly154Glu | + | Ser163Glu | + | Tyr217Ser |
| Gly97Pro | + | Ser204Glu | + | Lys213Asp | + | Ala216Glu | + | Gly219Ser |
| Val165Ser | + | Lys213Glu | + | Tyr214Cys | + | Ala216Glu | + | Tyr217Pro |
| Ser191Glu | + | Ser204Glu | + | Gln206Asp | + | Tyr214His | + | Ala216Asp |
| Gly102Pro | + | Asn155Asp | + | Ala216Glu | + | Tyr217His | + | Asn218Glu |
| Asn155Asp | + | Gly215Pro | + | Ala216Glu | + | Tyr217Ser | + | Asn218Glu |
| Gly160Ser | + | Ser204Glu | + | Gln206Glu | + | Lys213Glu | + | Ala216Ser |
| Ala98Thr | + | Ala187Ser | + | Ser204Glu | + | Gln206Glu | + | Lys213Asp |
| Gly127Pro | + | Ser204Glu | + | Gln206Glu | + | Lys213Glu | + | Tyr217Ala |
| Leu126Met | + | Pro129Glu | + | Ser163Glu | + | Phe189Thr | + | Asn218Ser |
| Ser101Asp | + | Ser204Asp | + | Gln206Glu | + | Ala216Asn | + | Tyr217Glu |
| Val95Ala | + | Tyr167Asp | + | Ser204Glu | + | Gln206Glu | + | Tyr217Glu |
| Asn155Glu | + | Glu156Asp | + | Thr164Asp | + | Ser204Glu | + | Tyr214Thr |
| Trp106Pro | + | Gly127Asp | + | Ser130Asp | + | Asn155Asp | + | Gly219Gln |
| Pro129Ser | + | Ser204Asp | + | Gln206Glu | + | Pro210Asp | + | Asn218Glu |
| Tyr104Val | + | Leu126Asp | + | Gly157Asp | + | Ser163Asp | + | Thr164Asp |
| Leu96Asp | + | Gly97Asp | + | Gln103Asp | + | Tyr217Cys | + | Gly219Asp |
| Ser159Glu | + | Asn212Gln | + | Lys213Glu | + | Gly215Asp | + | Ala216Glu |
| Gln59Asp | + | Asn62Glu | + | Ser63Glu | + | Pro129Ser | + | Asn155Asp |
| Gln103Ser | + | Tyr104Ala | + | Val203Asp | + | Gln206Asp | + | Lys213Glu |
| Val95Glu | + | Glu156Asp | + | Gly157Asp | + | Tyr214Gly | + | Thr220Asp |
| Val95Glu | + | Gly215Glu | + | Ala216Glu | + | Tyr217Leu | + | Gly219Ser |
| Ser63Asp | + | Gly160Asp | + | Ser161Glu | + | Val203Ser | + | Tyr217Cys |
| Gly160Asp | + | Ser161Asp | + | Tyr167Met | + | Ser204Asp | + | Tyr217Ala |
| Leu96His | + | Trp106Asp | + | Gln206Asn | + | Asn218Asp | + | Gly219Asp |
| Gly100Glu | + | Ser101Asp | + | Trp106Met | + | Ser162Asp | + | Thr164Pro |
| Ser105Glu | + | Ala187Ser | + | Val203Glu | + | Ser204Asp | + | Ala216Gly |
| Asp60Glu | + | Trp106Asn | + | Val203Glu | + | Ser204Asp | + | Ala216Gln |
| Gln103Asp | + | Ser163Glu | + | Thr164Glu | + | Pro201Gln | + | Ala216Pro |
| Val95Gln | + | Gly100Asn | + | Glu156Asp | + | Gly157Asp | + | Lys213Glu |
| Thr158Asp | + | Ser159Asp | + | Ser204Glu | + | Gly215Asn | + | Tyr217Cys |

TABLE 25-continued

Multi-loop Quintuples Mutation Variants

| | | | | |
|---|---|---|---|---|
| Ser105Asp | + Trp106Glu | + Thr164Asn | + Ala216Asp | + Gly219Ser |
| Gln59Glu | + Asp60Glu | + Tyr104Asn | + Ser191Glu | + Pro201Gln |
| Gln103Asp | + Ser161Glu | + Ser162Asp | + Gln206Ser | + Tyr217HjS |
| Ala98Asp | + Asp99Glu | + Ser105Glu | + Thr164Gln | + Ala187Ser |
| Gly154Asp | + Asn155Asp | + Ser204Glu | + Ala216Gln | + Tyr217Ala |
| Asn61Glu | + Tyr104Ser | + Gln206Glu | + Ala216Glu | + Tyr217Cys |
| Gly157Ser | + Thr158Glu | + Gln206Asp | + Lys213Asp | + Ala216Asp |
| Val95Thr | + Gly157Glu | + Ser188Glu | + Ser204Glu | + Ala216Asp |
| Tyr104His | + Asn155Glu | + Gly157Asn | + Tyr167Glu | + Gly202Ser |
| Gly128Asp | + Gly157Asn | + Pro210Gln | + Asn218Glu | + Thr220Glu |
| Asn62Glu | + Val95Ala | + Gly100Asp | + Lys213Glu | + Tyr217His |
| Gly166Asp | + Gln206Ser | + Gly215Pro | + Tyr217Asp | + Gly219Asp |
| Ser130Asp | + Ser163Asp | + Tyr167Ser | + Ser191Asp | + Tyr217Met |
| Gly97Pro | + Ser132Asp | + Thr158Gly | + Ser204Glu | + Ala216Asp |
| Gly154Asp | + Ser191Asp | + Lys213Asp | + Tyr214Ala | + Tyr217Asn |
| Asn61Gln | + Ile107His | + Ser204Glu | + Lys213Glu | + Asn218Glu |
| Gln59Asp | + Ala98Glu | + Gly102Asp | + Ser105Glu | + Leu209Thr |
| Ala133Gly | + Gly154Asp | + Gln206Glu | + Gly215Glu | + Thr220Gln |
| Gly154Asn | + Gly160Ser | + Gly166Glu | + Gln206Asp | + Gly215Asp |
| Leu96Glu | + Ala98Asn | + Tyr167Asn | + Gln206Glu | + Gly215Glu |
| Ser162Glu | + Thr164Glu | + Thr208Gln | + Ala216Asp | + Tyr217Glu |
| Val95Asp | + Ile107Asp | + Tyr167His | + Ser188Glu | + Thr220Asn |
| Gly154Glu | + Gly166Asp | + Lys213Asp | + Ala216Ser | + Tyr217Cys |
| Gly97Glu | + Asp99Glu | + Glu156Asp | + Tyr167Ala | + Ala216Pro |
| Thr66Gly | + Gln103Asp | + Trp106Glu | + Gly128Asn | + Ser162Asp |
| Gln103Asp | + Ser105Glu | + Thr158Ser | + Leu209Thr | + Lys213Glu |
| Thr66Gln | + Thr164Asp | + Val203His | + Gly211Glu | + Lys213Glu |
| Pro129Asn | + Gly131Gln | + Thr164Glu | + Gly211Glu | + Lys213Asp |
| Ser159Asp | + Ser162Glu | + Gln206Ser | + Pro210Glu | + Tyr214Ala |
| Asp99Glu | + Ser101Asp | + Gly131Asn | + Lys213Glu | + Gly215Ser |
| Gln103Glu | + Tyr104Gly | + Thr164Pro | + Pro210Asp | + Asn212Glu |
| Asn62Ser | + Ser132Asp | + Gly160Glu | + Ser162Glu | + Ala216His |
| Gly160Glu | + Ser162Asp | + Tyr167Ile | + Ser204Glu | + Gly219Ser |
| Asp60Glu | + Ser63Asp | + Ser130Glu | + Gly202Gln | + Gly215Ser |
| Gly154Glu | + Glu156Asp | + Pro210Glu | + Lys213Asp | + Asn218Gln |
| Ser105Asp | + Trp106Gly | + Gly127Asp | + Gly154Asp | + Val165Gln |
| Asn62Glu | + Gly100Glu | + Gly157Asn | + Gly166Glu | + Tyr217Leu |
| Asn62Asp | + Pro129Gly | + Ala133Gly | + Ser204Asp | + Gln206Asp |
| Asp60Glu | + Gly100Asn | + Ser204Asp | + Gln206Glu | + Pro210Ser |
| Ser162Glu | + Thr164Glu | + Val203Thr | + Ser204Glu | + Asn212Ser |
| Gly97Glu | + Ser130Glu | + Tyr167Asp | + Tyr217Val | + Gly219Ser |
| Gly128Glu | + Ser163Glu | + Gly166Glu | + Gln206Glu | + Ala216Ser |
| Asp60Glu | + Asn61Glu | + Ala187Gly | + Lys213Glu | + Ala216Glu |
| Gly97Asp | + Ser101Asp | + Tyr104Glu | + Ser161Glu | + Tyr217Val |
| Ser63Glu | + Ile107Gln | + Gln206Asp | + Ala216Asp | + Thr220Glu |
| Ser130Glu | + Ser132Glu | + Gly160Asp | + Ala216Gln | + Thr220Gly |
| Val95Glu | + Ser130Asp | + Ser132Glu | + Ala200Gly | + Tyr217His |
| Thr66Gly | + Gly100Glu | + Gln103Asp | + Ser132Asp | + Tyr217Asn |
| Asp60Glu | + Gly128Glu | + Gln206Asn | + Pro210Glu | + Ala216Gln |
| Leu126Val | + Thr158Glu | + Val203Met | + Lys213Asp | + Gly215Glu |
| Asp99Glu | + Ser159Glu | + Thr164Glu | + Tyr167Leu | + Gln206Ser |
| Val95Asp | + Pro129Asn | + Thr164Gln | + Ala216Glu | + Asn218Glu |
| Gly154Asp | + Ala187Gly | + Gly215Asp | + Tyr217Thr | + Asn218Glu |
| Asn62Glu | + Gly97Asp | + Gly100Asn | + Ser204Glu | + Tyr217Cys |
| Asn62Glu | + Gly97Asp | + Glu156Asp | + Val203Cys | + Ala216Gly |
| Asn62Asp | + Gly97Asp | + Ser204Asp | + Tyr214Leu | + Tyr217Leu |
| Glu156Asp | + Ser163Asp | + Gln206Ser | + Gly215Asp | + Ala216Asp |
| Ser159Glu | + Ser163Glu | + Phe189His | + Ser204Glu | + Tyr217Ser |
| Gly100Pro | + Asn155Gln | + Ser159Asp | + Ser163Asp | + Ser204Glu |
| Gly102Asp | + Ala187Asp | + Ser188Asp | + Val203His | + Ser204Asp |
| Asp99Glu | + Thr158Asp | + Ser162Asp | + Val203Met | + Ala216Thr |
| Val95Cys | + Gly97Pro | + Ser163Glu | + Ser191Asp | + Ser204Asp |
| Leu96Glu | + Asp99Glu | + Ser159Glu | + Gln206Asn | + Ala216Thr |
| Gly127Pro | + Ser162Glu | + Ser191Glu | + Gly211Glu | + Asn212Asp |
| Ser63Glu | + Ser191Asp | + Gln206Asp | + Ala216Asp | + Tyr217Gln |
| Ser63Glu | + Phe189Ile | + Val203Met | + Gln206Asp | + Gly211Glu |
| Trp106Tyr | + Phe189Asp | + Pro210Asp | + Lys213Asp | + Asn218Glu |
| Ser191Glu | + Gln206Glu | + Ala216Gly | + Tyr217Leu | + Thr220Asp |
| Val95Gly | + Thr158Asp | + Ser161Asp | + Ala187Pro | + Asn218Asp |
| Thr66Glu | + Gly166Glu | + Phe189Val | + Ser191Glu | + Gly219Ser |
| Asp60Glu | + Asp99Glu | + Gln206Glu | + Gly211Pro | + Ala216Glu |
| Asp6iAsp | + Ser63Asp | + Gln103Glu | + Lys213Asp | + Tyr217Pro |
| Tyr104Glu | + Gly128Gln | + Ser132Glu | + Asn212Asp | + Ala216Ser |
| Asn62Asp | + Ser204Asp | + Gly215Glu | + Ala216Gln | + Tyr217Leu |
| Asn61Asp | + Gly100Asp | + Trp106Ala | + Asn212Gln | + Lys213Asp |
| Gly127Glu | + Gly157Gln | + Ser204Asp | + Lys213Asp | + Ala216Glu |
| Leu96Glu | + Gly97Ser | + Gly100Glu | + Gln206Asp | + Lys213Asp |

TABLE 25-continued

| Multi-loop Quintuples Mutation Variants | | | | | | | | | |
|---|---|---|---|---|---|---|---|---|---|
| Asp60Glu | + | Leu96Cys | + | Gly97Glu | + | Ser204Glu | + | Gly215Asn |
| Tyr167Pro | + | Ser204Asp | + | Lys213Glu | + | Ala216His | + | Gly219Glu |
| Gly97Ser | + | Ser105Asp | + | Asn155Glu | + | Gly166Asp | + | Val203Asn |
| Gly102Asn | + | Gly160Asn | + | Thr164Glu | + | Gln206Asn | + | Thr220Asp |
| Asn61Ser | + | Ala98Asp | + | Asn155Asp | + | Ser188Glu | + | Val203Ser |
| Glu156Asp | + | Ser204Asp | + | Gln206Glu | + | Lys213Glu | + | Ala216Pro |
| Asp99Glu | + | Gly157Pro | + | Ser204Glu | + | Gln206Asp | + | Lys213Glu |
| Ser130Asp | + | Gly160Asn | + | Ser204Glu | + | Gln206Asn | + | Gly215Asp |
| Gly127Glu | + | Glu156Asp | + | Ser204Glu | + | Gln206Asp | + | Tyr214Pro |
| Ala98Glu | + | Asp99Glu | + | Trp106Gly | + | Gly154Asp | + | Asn218Glu |
| Gln59Ser | + | Val95Glu | + | Ala98Asn | + | Ser105Glu | + | Gln206Glu |
| Gly97Pro | + | Gly128Glu | + | Lys213Asp | + | Ala216Glu | + | Asn218Glu |
| Gln103Asp | + | Ile107Asp | + | Gly157Pro | + | Tyr167Glu | + | Ala216His |
| Asp60Glu | + | Gln206Glu | + | Lys213Asp | + | Gly215Pro | + | Asn218Glu |
| Ser130Glu | + | Thr164Glu | + | Val203Met | + | Ser204Asp | + | Gln206Asp |
| Asp60Glu | + | Ser63Glu | + | Gly154Asp | + | Gly166Ser | + | Ser188Asp |
| Leu96His | + | Ser130Glu | + | Glu156Asp | + | Tyr167Glu | + | Lys213Glu |
| Gln59Ser | + | Glu156Asp | + | Gly160Glu | + | Gly211Glu | + | Lys213Glu |
| Gly127Glu | + | Asn155Asp | + | Ala187His | + | Ala216Glu | + | Tyr217His |
| Gln103Glu | + | Gly160Asn | + | Gln206Glu | + | Tyr214Gly | + | Asn218Glu |
| Ser63Asp | + | Gly202Pro | + | Lys213Asp | + | Gly215Gln | + | Asn218Asp |
| Asp60Glu | + | Leu96Glu | + | Thr158Gln | + | Gly166Pro | + | Gln206Asp |
| Gly97Asp | + | Gln103Asp | + | Phe189Ala | + | Gln206Ser | + | Lys213Asp |
| Asn62Asp | + | Thr66Glu | + | Tyr104Pro | + | Ser132Asp | + | Asn212Asp |
| Ala98Pro | + | Pro129Asp | + | Ser130Asp | + | Lys213Glu | + | Tyr217Glu |
| Ser63Asp | + | Glu156Asp | + | Gln206Glu | + | Lys213Glu | + | Ala216Pro |
| Asp60Glu | + | Gly102Gln | + | Ser105Glu | + | Thr164Gln | + | Gly211Glu |
| Asp60Glu | + | Thr158Gln | + | Lys213Glu | + | Ala216Gln | + | Tyr217Val |
| Ile107Asp | + | Gly131Asp | + | Ala216Asp | + | Tyr217His | + | Asn218Asp |
| Ser63Asp | + | Gly100Glu | + | Gln103Asp | + | Gln206Asn | + | Gly219Asp |
| Asn155Glu | + | Gly157Glu | + | Gln206Asn | + | Pro210Asp | + | Ala216Glu |
| Ser63Asp | + | Ile107Met | + | Pro129Asn | + | Ser191Asp | + | Gly219Glu |
| Ser63Asp | + | Val95Ala | + | Asp99Glu | + | Leu126Thr | + | Ser163Asp |
| Thr66Glu | + | Gly100Gln | + | Gln103Asp | + | Lys213Asp | + | Ala216Asn |
| Thr158Asp | + | Ser161Asp | + | Gln206Asp | + | Tyr217Cys | + | Gly219Asp |
| Ser63Glu | + | Ser162Asp | + | Ala187Gln | + | Gly211Asn | + | Lys213Asp |
| Gly97Ser | + | Ser101Asp | + | Val203Cys | + | Tyr214Glu | + | Tyr217Asp |
| Val95Glu | + | Asp99Glu | + | Ser204Asp | + | Gly215Glu | + | Asn218Gln |
| Gln59Glu | + | Thr66Asp | + | Ser163Asp | + | Pro201Gln | + | Gly215Glu |
| Ala98His | + | Ser101Glu | + | Gly166Gln | + | Ser188Asp | + | Val203Asp |
| Ser63Asp | + | Gly160Asp | + | Val203Ala | + | Ser204Asp | + | Gln206Glu |
| Gly127Glu | + | Ser162Glu | + | Ser163Glu | + | Lys213Asp | + | Ala216His |
| Ser162Asp | + | Ala187Glu | + | Pro201Gln | + | Gln206Asp | + | Tyr217Glu |
| Gly157Glu | + | Phe189Tyr | + | Val203Glu | + | Ser204Glu | + | Lys213Glu |
| Gly160Glu | + | Ser161Asp | + | Tyr167Glu | + | Gly202Asn | + | Gln206Glu |
| Asp60Glu | + | Ser159Asp | + | Thr164Glu | + | Phe189His | + | Lys213Glu |
| Tyr104Cys | + | Ser162Glu | + | Lys213Glu | + | Asn218Asp | + | Gly219Glu |
| Tyr104Asp | + | Gly128Asn | + | Ser130Asp | + | Gly157Ser | + | Ser204Glu |
| Ser132Glu | + | Gly157Ser | + | Ser163Asp | + | Asn212Asp | + | Lys213Glu |
| Gly97Asp | + | Ala98Asp | + | Pro129Glu | + | Tyr167Leu | + | Gln206Asp |
| Ser101Glu | + | Thr158Gln | + | Ala187Glu | + | Ser188Glu | + | Gln206Glu |
| Asp99Glu | + | Gly100Asp | + | Asn155Asp | + | Gly166Gln | + | Ser204Glu |
| Ser130Glu | + | Ser161Glu | + | Ser162Asp | + | Thr164Asn | + | Gly211Asp |
| Gln59Asn | + | Tyr104Asp | + | Thr158Asp | + | Ser191Glu | + | Asn218Glu |
| Asp60Glu | + | Ser101Glu | + | Ser204Glu | + | Gln206Ser | + | Pro210Asp |
| Ser130Asp | + | Ser159Asp | + | Ser163Glu | + | Pro210Gln | + | Tyr217Asp |
| Asn61Asp | + | Gly100Asp | + | Trp106Pro | + | Gly128Glu | + | Tyr217Asp |
| Gly102Pro | + | Gly131Asp | + | Ser188Asp | + | Ser204Glu | + | Gln206Glu |
| Glu156Asp | + | Ser204Asp | + | Gln206Asp | + | Asn212Asp | + | Ala216His |
| Thr66Pro | + | Gln103Asp | + | Glu156Asp | + | Ser191Glu | + | Gln206Asp |
| Gly131Pro | + | Phe189Leu | + | Ser191Glu | + | Gln206Glu | + | Lys213Glu |
| Ala98Glu | + | Gly157Ser | + | Gln206Asp | + | Lys213Asp | + | Gly215Gln |
| Tyr104Leu | + | Thr158Glu | + | Gly202Ser | + | Gln206Glu | + | Lys213Glu |
| Ser63Glu | + | Ala98Gln | + | Gly102Asn | + | Ser130Asp | + | Tyr217Glu |
| Thr158Glu | + | Gly166Asn | + | Pro210Glu | + | Lys213Glu | + | Thr220Glu |
| Trp106Thr | + | Gly154Ser | + | Gly157Asp | + | Lys213Glu | + | Ala216Glu |
| Ala98Ser | + | Ala187Glu | + | Lys213Asp | + | Gly215Gln | + | Ala216Asp |
| Tyr104Pro | + | Ser159Asp | + | Gly202Asn | + | Lys213Glu | + | Ala216Glu |
| Leu126Asn | + | Asn155Glu | + | Thr164Asn | + | Lys213Asp | + | Ala216Glu |
| Ser161Asp | + | Val203His | + | Ser204Asp | + | Gly211Asp | + | Tyr217Asp |
| Asn61Asp | + | Ser163Asp | + | Val203His | + | Ser204Glu | + | Tyr217Asp |
| Val95Asp | + | Trp106Glu | + | Ser161Glu | + | Ala187Pro | + | Ser204Asp |
| Leu96Glu | + | Gly100Asp | + | Trp106Cys | + | Ser188Glu | + | Gln206Asp |
| Ser101Glu | + | Ser204Asp | + | Gly211Glu | + | Lys213Glu | + | Gly215Asn |
| Asp99Glu | + | Ser159Glu | + | Ser162Glu | + | Ser204Asp | + | Gly219Asn |
| Leu96Ala | + | Gln103Asp | + | Leu126Val | + | Gly128Asp | + | Ser204Asp |
| Ala98Glu | + | Ser105Glu | + | Gly154Glu | + | Glu156Asp | + | Phe189Pro |

TABLE 25-continued

Multi-loop Quintuples Mutation Variants

| | | | | | | | | |
|---|---|---|---|---|---|---|---|---|
| Asn61Glu | + | Ser159Glu | + | Gln206Ser | + | Pro210Glu | + | Ala216Glu |
| Gly97Asp | + | Ser101Asp | + | Ala133Glu | + | Gln206Glu | + | Gly219Pro |
| Leu126Ala | + | Gly131Glu | + | Ser204Glu | + | Pro210Asp | + | Lys213Glu |
| Val95Glu | + | Ala98Asn | + | Gly102Glu | + | Ser162Asp | + | Ser204Glu |
| Asn61Glu | + | Gly100Asn | + | Pro129Asp | + | Ser163Glu | + | Asn218Ser |
| Gly102Asp | + | Gly127Ser | + | Thr158Asp | + | Gly160Glu | + | Lys213Glu |
| Ser130Asp | + | Asn155Gln | + | Thr158Glu | + | Ser191Asp | + | Gly215Glu |
| Ala133Asp | + | Ser159Glu | + | Ser161Asp | + | Ser204Asp | + | Ala216Gln |
| Ser132Glu | + | Thr164Asp | + | Ser204Asp | + | Gln206Glu | + | Tyr217Pro |
| Gly157Glu | + | Tyr167Asp | + | Ser204Glu | + | Gln206Glu | + | Ala216Asn |
| Thr66Ser | + | Ser130Glu | + | Thr158Glu | + | Ser204Glu | + | Gln206Glu |
| Asp99Glu | + | Ser159Glu | + | Ser204Glu | + | Gln206Glu | + | Tyr217Pro |
| Thr66Ser | + | Ser105Asp | + | Ser159Glu | + | Ser204Glu | + | Gln206Asp |
| Asp60Glu | + | Gly127Asp | + | Ser204Glu | + | Gln206Glu | + | Tyr214Asn |
| Ser63Glu | + | Ser130Asp | + | Gln206Asp | + | Ala216Gly | + | Asn218Asp |
| Pro129Gly | + | Ser159Glu | + | Ser188Glu | + | Phe189Cys | + | Ser204Asp |
| Gly131Asp | + | Glu156Asp | + | Ser162Glu | + | Ala187Pro | + | Tyr214Gly |
| Gly102Asp | + | Trp106Glu | + | Ser159Glu | + | Pro210Gln | + | Thr220Asp |
| Gly131Asp | + | Ser161Asp | + | Ser163Asp | + | Gly166Asn | + | Ser204Asp |
| Gln59Asn | + | Ser188Asp | + | Gln206Asp | + | Gly211Glu | + | Tyr217Glu |
| Ala98Glu | + | Gly157Asp | + | Thr164Asp | + | Phe189Thr | + | Lys213Asp |
| Gln103Asp | + | Trp106Tyr | + | Gly160Asp | + | Lys213Glu | + | Gly215Asp |
| Val95Asp | + | Gly131Gln | + | Ser159Asp | + | Ala216Asp | + | Asn218Asp |
| Ser101Asp | + | Gln103Glu | + | Ser161Glu | + | Gln206Glu | + | Ala216His |
| Thr66Glu | + | Gly128Pro | + | Gly154Asp | + | Thr164Asp | + | Ser204Glu |
| Val95Asp | + | Gly131Glu | + | Ser163Asp | + | Ser191Glu | + | Gln206Asn |
| Val95Ser | + | Ala98Glu | + | Ser101Asp | + | Gly131Asp | + | Phe189Asp |
| Asn62Asp | + | Leu126His | + | Gly131Pro | + | Lys213Glu | + | Tyr217Asp |
| Ser63Asp | + | Ser130Glu | + | Thr158Pro | + | Ala216Glu | + | Tyr217Ile |
| Gln59Asp | + | Gly157Asp | + | Gln206Glu | + | Tyr214Val | + | Asn218Asp |
| Val95Glu | + | Asp99Glu | + | Gly215Asp | + | Ala216Asn | + | Tyr217Ile |
| Ser132Glu | + | Gly154Gln | + | Gly157Glu | + | Ser161Asp | + | Tyr214Ser |
| Ser101Asp | + | Gly131Pro | + | Ser188Asp | + | Ser191Glu | + | Gln206Glu |
| Thr66Asp | + | Leu96Glu | + | Glu156Asp | + | Val203His | + | Gly215Asp |
| Asn62Glu | + | Gly166Gln | + | Ser188Glu | + | Gly211Glu | + | Ala216His |
| Ile107Asp | + | Ala187Asp | + | Ser191Asp | + | Gln206Asp | + | Ala216Thr |
| Ser105Asp | + | Ser159Glu | + | Ser191Asp | + | Lys213Asp | + | Ala216Thr |
| Asn155Asp | + | Ser163Asp | + | Val165Asn | + | Gln206Ser | + | Lys213Glu |
| Ser101Glu | + | Gly131Asn | + | Asn155Glu | + | Ala187Glu | + | Lys213Asp |
| Gln59Glu | + | Gly160Asp | + | Ser188Asp | + | Val203Glu | + | Tyr217Ile |
| Ala133Asp | + | Ser161Glu | + | Thr164Asp | + | Ser204Asp | + | Asn218Ser |
| Gln103Glu | + | Tyr104Cys | + | Ser161Glu | + | Thr164Asp | + | Lys213Glu |
| Ser63Glu | + | Gly160Asp | + | Tyr167Met | + | Lys213Asp | + | Asn218Asp |
| Ser101Glu | + | Leu126Glu | + | Ser188Glu | + | Lys213Asp | + | Ala216Asn |
| Asp60Glu | + | Leu96Glu | + | Gly128Asn | + | Ser130Glu | + | Gln206Glu |
| Gln103Ser | + | Ser130Asp | + | Ala133Gly | + | Gln206Asp | + | Gly219Asp |
| Gly102Asn | + | Ser162Asp | + | Gln206Asp | + | Tyr217Gly | + | Gly219Asp |
| Thr66Gln | + | Asp99Glu | + | Gln103Glu | + | Val203Ser | + | Tyr217Asp |
| Asp99Glu | + | Gln103Asp | + | Gly157Asn | + | Lys213Asp | + | Ala216Gln |
| Thr66Asp | + | Pro129Asp | + | Ser159Glu | + | Lys213Asp | + | Tyr217His |
| Ser63Asp | + | Gly97Asp | + | Tyr167Ala | + | Ser188Asp | + | Ser204Glu |
| Gly102Pro | + | Tyr104Ala | + | Glu156Asp | + | Tyr167Glu | + | Ser204Glu |
| Gln59Glu | + | Asn62Gln | + | Gln103Glu | + | Gly131Glu | + | Phe189Leu |
| Asp60Glu | + | Ser162Glu | + | Ala200Gln | + | Val203Glu | + | Gly211Asp |
| Asp60Glu | + | Ile107Glu | + | Gly157Asp | + | Gly160Glu | + | Phe189Ser |
| Ser101Asp | + | Gly102Ser | + | Tyr104Glu | + | Phe189Asp | + | Lys213Glu |
| Ser101Asp | + | Ser105Asp | + | Val203Asp | + | Ala216His | + | Tyr217His |
| Ser132Asp | + | Asn155Glu | + | Gly211Pro | + | Lys213Glu | + | Asn218Asp |
| Gln103Asp | + | Gly128Asp | + | Ser163Asp | + | Ala187Glu | + | Tyr217Ile |
| Leu96Ile | + | Gly128Asp | + | Ser191Glu | + | Gly202Asn | + | Gln206Glu |
| Thr66Glu | + | Gln103Asp | + | Ser204Glu | + | Lys213Asp | + | Gly219Ser |
| Ala98Asp | + | Ser132Asp | + | Gly166Glu | + | Pro210Asp | + | Tyr214Gln |
| Ser63Glu | + | Pro129Glu | + | Val203Met | + | Lys213Glu | + | Gly219Asp |
| Gln59Glu | + | Gly97Asp | + | Gly128Asp | + | Ser159Glu | + | Ala216Ser |
| Ser63Glu | + | Gln103Glu | + | Ile107Ser | + | Glu156Asp | + | Lys213Asp |
| Gly102Asp | + | Gly157Asn | + | Ser162Glu | + | Ser191Glu | + | Ser204Glu |
| Ser105Asp | + | Ser162Asp | + | Ser191Asp | + | Pro210Gly | + | Gly211Glu |
| Asp60Glu | + | Val95Glu | + | Trp106Gly | + | Pro129Glu | + | Ser159Asp |
| Ser101Glu | + | Trp106Asp | + | Thr164Glu | + | Ser204Asp | + | Pro210Ser |
| Gln59Glu | + | Gly100Gln | + | Gly157Asp | + | Gly211Asp | + | Tyr217Glu |
| Gly97Asp | + | Gly130Asp | + | Gln206Asp | + | Lys213Asp | + | Ala216Asn |
| Tyr104Asp | + | Gly154Asp | + | Gly160Asn | + | Ser163Asp | + | Ser204Glu |
| Ser132Glu | + | Gly154Glu | + | Ser163Glu | + | Pro210Gly | + | Asn212Asp |
| Leu96Thr | + | Ala133Glu | + | Asn155Glu | + | Lys213Glu | + | Ala216Asp |
| Asp60Glu | + | Asp99Glu | + | Leu126Gly | + | Ser130Asp | + | Ser162Glu |

II. Cleaning Compositions

In another embodiment of the present invention, an effective amount of one or more of the enzyme variants are included in compositions useful for cleaning a variety of surfaces in need of proteinaceous stain removal. Such cleaning compositions include detergent compositions for cleaning hard surfaces, unlimited in form (e.g., liquid and granular); detergent compositions for cleaning fabrics, unlimited in form (e.g., granular, liquid and bar formulations); dishwashing compositions (unlimited in form); oral cleaning compositions, unlimited in form (e.g., dentifrice, toothpaste and mouthwash formulations); denture cleaning compositions, unlimited in form (e.g., liquid, tablet); and contact lens cleaning compositions, unlimited in form (e.g., liquid, tablet).

The cleaning compositions also comprise, in addition to the BPN' variants described hereinbefore, one or more cleaning composition materials compatible with the protease enzyme. the term "cleaning composition material", as used herein, means any liquid, solid or gaseous material selected for the particular type of cleaning composition desired and the form of the product (e.g., liquid, granule, bar, spray, stick, paste, gel), which materials are also compatible with the BPN' variant used in the composition. the specific selection of cleaning composition materials are readily made by considering the surface material to be cleaned, the desired form of the composition for the cleaning condition during use (e.g., through the wash detergent use). The term "compatible", as used herein, means the cleaning composition materials do not reduce the proteolytic activity of the BPN' variant to such an extent that the protease is not effective as desired during normal use situations. Specific cleaning composition materials are exemplified in detail hereinafter.

As used herein, "effective amount of enzyme variant" refers to the quantity of enzyme variant necessary to achieve the enzymatic activity necessary in the specific cleaning composition. Such effective amounts are readily ascertained by one of ordinary skill in the art and is based on many factors, such as the particular enzyme variant used, the cleaning application, the specific composition of the cleaning composition, and whether a liquid or dry (e.g., granular, bar) composition is required, and the like. Preferably the cleaning compositions comprise from about 0.0001% to about 10% of one or more enzyme variants of the present invention, more preferably from about 0.001% to about 1%, more preferably still from about 0.01% to about 0.1%. Several examples of various cleaning compositions wherein the enzyme variants may be employed are discussed in further detail below. All parts, percentages and ratios used herein are by weight unless otherwise specified.

As used herein, "non-fabric cleaning compositions" include hard surface cleaning compositions, dishwashing compositions, oral cleaning compositions, denture cleaning compositions and contact lens cleaning compositions.

A. Cleaning Compositions for Hard Surfaces, Dishes and Fabrics

The enzyme variants of the present invention can be used in a variety of detergent compositions where high sudsing and good insoluble substrate removal are desired. Thus the enzyme variants can be used with various conventional ingredients to provide fully-formulated hard-surface cleaners, dishwashing compositions, fabric laundering compositions and the like. Such compositions can be in the form of liquids, granules, bars and the like. Such compositions can be formulated as modern "concentrated" detergents which contain as much as 30%–60% by weight of surfactants.

The cleaning compositions herein can optionally, and preferably, contain various anionic, nonionic, zwitterionic, etc., surfactants. Such surfactants are typically present at levels of from about 5% to about 35% of the compositions.

Nonlimiting examples of surfactants useful herein include the conventional $C_{11}$–$C_{18}$ alkyl benzene sulfonates and primary and random alkyl sulfates, the $C_{10}$–$C_{18}$ secondary (2,3) alkyl sulfates of the formulas $CH_3(CH_2)x(CHOSO_3)^-M^+)CH_3$ and $CH_3(CH_2)y(CHOSO_3^-M^+)CH_2CH_3$ wherein x and (y+1) are integers of at least about 7, preferably at least about 9, and M is a water-solubilizing cation, especially sodium, the $C_{10}$–$C_{18}$ alkyl alkoxy sulfates (especially EO 1–5 ethoxy sulfates), $C_{10}$–$C_{18}$ alkyl alkoxy carboxylates (especially the EO 1–5 ethoxycarboxylates), the $C_{10}$–$C_{18}$ alkyl polyglycosides, and their corresponding sulfated polyglycosides, $C_{12}$–$C_{18}$ alpha-sulfonated fatty acid esters, $C_{12}$–$C_{18}$ alkyl and alkyl phenol alkoxylates (especially ethoxylates and mixed ethoxyipropoxy), $C_{12}$–$C_{18}$ betaines and sulfobetaines ("sultaines"), $C_{10}$–$C_{18}$ amine oxides, and the like. The alkyl alkoxy sulfates (AES) and alkyl alkoxy carboxylates (AEC) are preferred herein. (Use of such surfactants in combination with the aforesaid amine oxide and/or betaine or sultaine surfactants is also preferred, depending on the desires of the formulator.) Other conventional useful surfactants are listed in standard texts. Particularly useful surfactants include the $C_{10}$–$C_{18}$ N-methyl glucamides disclosed in U.S. Pat. No. 5,194,639, Connor et al., issued Mar. 16, 1993, incorporated herein by reference.

A wide variety of other ingredients useful in detergent cleaning compositions can be included in the compositions herein, including other active ingredients, carriers, hydrotropes, processing aids, dyes or pigments, solvents for liquid formulations, etc. If an additional increment of sudsing is desired, suds boosters such as the $C_{10}$–$C_{16}$ alkolamides can be incorporated into the compositions, typically at about 1% to about 10% levels. The $C_{10}$–$C_{14}$ monoethanol and diethanol amides illustrate a typical class of such suds boosters. Use of such suds boosters with high sudsing adjunct surfactants such as the amine oxides, betaines and sultaines noted above is also advantageous. If desired, soluble magnesium salts such as $MgCl_2$, $MgSO_4$, and the like, can be added at levels of, typically, from about 0.1% to about 2%, to provide additionally sudsing.

The liquid detergent compositions herein can contain water and other solvents as carriers. Low molecular weight primary or secondary alcohols exemplified by methanol, ethanol, propanol, and isopropanol are suitable. Monohydric alcohols are preferred for solubilizing surfactants, but polyols such as those containing from about 2 to about 6 carbon atoms and from about 2 to about 6 hydroxy groups (e.g., 1,3-propanediol, ethylene glycol, glycerine, and 1,2-propanediol) can also be used. The compositions may contain from about 5% to about 90%, typically from about 10% to about 50% of such carriers.

The detergent compositions herein will preferably be formulated such that during use in aqueous cleaning operations, the wash water will have a pH between about 6.8 and about 11.0. Finished products thus are typically formulated at this range. Techniques for controlling pH at recommended usage levels include the use of buffers, alkalis, acids, etc., and are well known to those skilled in the art.

When formulating the hard surface cleaning compositions and fabric cleaning compositions of the present invention, the formulator may wish to employ various builders at levels from about 5% to about 50% by weight. Typical builders include the 1–10 micron zeolites, polycarboxylates such as citrate and oxydisuccinates, layered silicates, phosphates, and the like. Other conventional builders are listed in standard formularies.

Likewise, the formulator may wish to employ various additional enzymes, such as cellulases, lipases, amylases and proteases in such compositions, typically at levels of from about 0.001% to about 1% by weight. Various detersive and fabric care enzymes are well-known in the laundry detergent art.

Various bleaching compounds, such as the percarbonates, perborates and the like, can be used in such compositions, typically at levels from about 1% to about 15% by weight. If desired, such compositions can also contain bleach activators such as tetraacetyl ethylenediamine, nonanoyloxybenzene sulfonate, and the like, which are also known in the art. Usage levels typically range from about 1% to about 10% by weight.

Various soil release agents, especially of the anionic oligoester type, various chelating agents, especially the aminophosphonates and ethylenediaminedisuccinates, various clay soil removal agents, especially ethoxylated tetraethylene pentamine, various dispersing agents, especially polyacrylates and polyasparatates, various brighteners, especially anionic brighteners, various suds suppressors, especially silicones and secondary alcohols, various fabric softeners, especially smectite clays, and the like can all be used in such compositions at levels ranging from about 1% to about 35% by weight. Standard formularies and published patents contain multiple, detailed descriptions of such conventional materials.

Enzyme stabilizers may also be used in the cleaning compositions. Such enzyme stabilizers include propylene glycol (preferably from about 1% to about 10%), sodium formate (preferably from about 0.1% to about 1%) and calcium formate (preferably from about 0.1% to about 1%).

1. Hard Surface Cleaning Compositions

As used herein "hard surface cleaning composition" refers to liquid and granular detergent compositions for cleaning hard surfaces such as floors, walls, bathroom tile, and the like. Hard surface cleaning compositions of the present invention comprise an effective amount of one or more enzyme variants of the present invention, preferably from about 0.001% to about 10%, more preferably from about 0.01% to about 5%, more preferably still from about 0.05% to about 1% by weight of active enzyme of the composition. In addition to comprising one or more of the enzyme variants, such hard surface cleaning compositions typically comprise a surfactant and a water-soluble sequestering builder. In certain specialized products such as spray window cleaners, however, the surfactants are sometimes not used since they may produce a filmy/streaky residue on the glass surface.

The surfactant component, when present, may comprise as little as 0.1% of the compositions herein, but typically the compositions will contain from about 0.25% to about 10%, more preferably from about 1% to about 5% of surfactant.

Typically the compositions will contain from about 0.5% to about 50% of a detergency builder, preferably from about 1% to about 10%.

Preferably the pH should be in the range of about 8 to 12. Conventional pH adjustment agents such as sodium hydroxide, sodium carbonate or hydrochloric acid can be used if adjustment is necessary.

Solvents may be included in the compositions. Useful solvents include, but are not limited to, glycol ethers such as diethyleneglycol monohexyl ether, diethyleneglycol monobutyl ether, ethyleneglycol monobutyl ether, ethyleneglycol monohexyl ether, propyleneglycol monobutyl ether, dipropyleneglycol monobutyl ether, and diols such as 2,2,4-trimethyl-1,3-pentanediol and 2-ethyl-1,3-hexanediol. When used, such solvents are typically present at levels of from about 0.5% to about 15%, preferably from about 3% to about 11%.

Additionally, highly volatile solvents such as isopropanol or ethanol can be used in the present compositions to facilitate faster evaporation of the composition from surfaces when the surface is not rinsed after "full strength" application of the composition to the surface. When used, volatile solvents are typically present at levels of from about 2% to about 12% in the compositions.

The hard surface cleaning composition embodiment of the present invention is illustrated by the following examples.

EXAMPLES 7–12

| | Liquid Hard Surface Cleaning Compositions | | | | | |
|---|---|---|---|---|---|---|
| | | | Example No. | | | |
| Component | 7 | 8 | 9 | 10 | 11 | 12 |
| Ser105Glu | 0.05 | 0.50 | 0.02 | 0.03 | 0.10 | 0.03 |
| Gly127Gln + Ala216Pro | — | — | — | — | 0.20 | 0.02 |
| Na$_2$DIDA* | | | | | | |
| EDTA** | — | — | 2.90 | 2.90 | — | — |
| Na Citrate | — | — | — | — | 2.90 | 2.90 |
| NaC$_{12}$ Alkyl-benzene sulfonate | 1.95 | — | 1.95 | — | 1.95 | — |
| NaC$_{12}$ Alkylsulfate | — | 2.20 | — | 2.20 | — | 2.20 |
| NaC$_{12 (ethoxy)}$*** sulfate | — | 2.20 | — | 2.20 | — | 2.20 |
| C$_{12}$ Dimethylamine oxide | — | 0.50 | — | 0.50 | — | 0.50 |
| Na Cumene sulfonate | 1.30 | — | 1.30 | — | 1.30 | — |
| Hexyl Carbitol*** | 6.30 | 6.30 | 6.30 | 6.30 | 6.30 | 6.30 |
| Water**** | | | balance to 100% | | | |

*Disodium N-diethyleneglycol-N,N-iminodiacetate
**Na$_4$ ethylenediamine diacetic acid
***Diethyleneglycol monohexyl ether
****All formulas adjusted to pH 7

In Examples 7–10, the BPN' variants recited in Tables 2–25, among others, are substituted for Ser105Glu, with substantially similar results.

In Examples 11–12, any combination of the BPN' variants recited in Tables 2–25, among others, are substituted for Gly127Gln+Ala216Pro, with substantially similar results.

EXAMPLES 13–18

| | Spray Compositions for Cleaning Hard Surfaces and Removing Household Mildew | | | | | |
|---|---|---|---|---|---|---|
| | | | Example No. | | | |
| Component | 13 | 14 | 15 | 16 | 17 | 18 |
| Tyr104Ile + Gly215Pro | 0.50 | 0.05 | 0.60 | 0.30 | 0.20 | 0.30 |
| Asp99Glu | — | — | — | — | 0.30 | 0.10 |
| Sodium octyl sulfate | 2.00 | 2.00 | 2.00 | 2.00 | 2.00 | 2.00 |
| Sodium dodecyl sulfate | 4.00 | 4.00 | 4.00 | 4.00 | 4.00 | 4.00 |
| Sodium hydroxide | 0.80 | 0.80 | 0.80 | 0.80 | 0.80 | 0.80 |
| Silicate (Na) | 0.04 | 0.04 | 0.04 | 0.04 | 0.04 | 0.04 |
| Perfume | 0.35 | 0.35 | 0.35 | 0.35 | 0.35 | 0.35 |
| Water | | | balance to 100% | | | |

Product pH is about 7.

In Examples 13–16, the BPN' variants recited in Tables 2–25, among others, are substituted for Tyr104Ile+Gly215Pro, with substantially similar results.

In Examples 17–18, any combination of the BPN' variants recited in Tables 2–25, among others, are substituted for Tyr104Ile+Gly215Pro and Asp99Glu, with substantially similar results.

2. Dishwashing Compositions

In another embodiment of the present invention, dishwashing compositions comprise one or more enzyme variants of the present invention. As used herein, "dishwashing composition" refers to all forms for compositions for cleaning dishes, including but not limited to, granular and liquid forms. The dishwashing composition embodiment of the present invention is illustrated by the following examples.

EXAMPLES 19–24

| | Dishwashing Composition | | | | | |
|---|---|---|---|---|---|---|
| | Example No. | | | | | |
| Component | 19 | 20 | 21 | 22 | 23 | 24 |
| Glu59Ser + Leu96Gly + Ser204Glu | 0.05 | 0.50 | 0.02 | 0.40 | 0.10 | 0.03 |
| Lys96Gly + Ser204Glu | — | — | — | — | 0.40 | 0.02 |
| $C_{12}$–$C_{14}$ N-methyl-glucamide | 0.90 | 0.90 | 0.90 | 0.90 | 0.90 | 0.90 |
| $C_{12}$ ethoxy (1) sulfate | 12.00 | 12.00 | 12.00 | 12.00 | 12.00 | 12.00 |
| 2-methyl undecanoic acid | 4.50 | 4.50 | 4.50 | 4.50 | 4.50 | 4.50 |
| $C_{12}$ ethoxy (2) carboxylate | 4.50 | 4.50 | 4.50 | 4.50 | 4.50 | 4.50 |
| $C_{12}$ alcohol ethoxylate (4) | 3.00 | 3.00 | 3.00 | 3.00 | 3.00 | 3.00 |
| $C_{12}$ amine oxide | 3.00 | 3.00 | 3.00 | 3.00 | 3.00 | 3.00 |
| Sodium cumene sulfonate | 2.00 | 2.00 | 2.00 | 2.00 | 2.00 | 2.00 |
| Ethanol | 4.00 | 4.00 | 4.00 | 4.00 | 4.00 | 4.00 |
| $Mg^{++}$ (as $MgCl_2$) | 0.20 | 0.20 | 0.20 | 0.20 | 0.20 | 0.20 |
| $Ca^{++}$ (as $CaCl_2$) | 0.40 | 0.40 | 0.40 | 0.40 | 0.40 | 0.40 |
| Water | balance to 100% | | | | | |

Product pH is adjusted to 7.

In Examples 19–22, the BPN' variants recited in Tables 2–25, among others, are substituted for Gln59SSer+Leu96Gly+Ser204Glu, with substantially similar results.

In Examples 23–24, any combination of the BPN' variants recited in Tables 2–25, among others, are substituted for Gln59SSer+Leu96Gly+Ser204Glu and Lys96Gly+Ser204Glu, with substantially similar results.

3. Fabric Cleaning Compositions

In another embodiment of the present invention, fabric cleaning compositions comprise one or more enzyme variants of the present invention. As used herein, "fabric cleaning composition" refers to all forms for detergent compositions for cleaning fabrics, including but not limited to, granular, liquid and bar forms. Preferred fabric cleaning compositions are those in the liquid form.

a. Granular Fabric Cleaning Compositions

The granular fabric cleaning compositions of the present invention contain an effective amount of one or more enzyme variants of the present invention, preferably from about 0.001% to about 10%, more preferably from about 0.005% to about 5%, more preferably from about 0.01% to about 1% by weight of active enzyme of the composition. In addition to one or more enzyme variants, the granular fabric cleaning compositions typically comprise at least one surfactant, one or more builders, and, in some cases, a bleaching agent.

The granular fabric cleaning composition embodiment of the present invention is illustrated by the following examples.

EXAMPLES 25–28

| | Granular Fabric Cleaning Composition | | | |
|---|---|---|---|---|
| | Example No. | | | |
| Component | 25 | 26 | 27 | 28 |
| Ser101Asp | 0.10 | 0.20 | 0.03 | 0.05 |
| Thr66Glu | — | — | 0.02 | 0.05 |
| $C_{13}$ linear alkyl benzene sulfonate | 22.00 | 22.00 | 22.00 | 22.00 |
| Phosphate (as sodium tripolyphosphates) | 23.00 | 23.00 | 23.00 | 23.00 |
| Sodium carbonate | 23.00 | 23.00 | 23.00 | 23.00 |
| Sodium silicate | 14.00 | 14.00 | 14.00 | 14.00 |
| Zeolite | 8.20 | 8.20 | 8.20 | 8.20 |
| Chelant (diethylaenetriamine pentaacetic acid) | 0.40 | 0.40 | 0.40 | 0.40 |
| Sodium sulfate | 5.50 | 5.50 | 5.50 | 5.50 |
| Water | balance to 100% | | | |

In Examples 25–26, the BPN' variants recited in Tables 2–25, among others, are substituted for Ser101Asp, with substantially similar results.

In Examples 27–28, any combination of the BPN' variants recited in Tables 2–25, among others, are substituted for Ser101Asp and Thr66Glu, with substantially similar results.

EXAMPLES 29–32

| | Granular Fabric Cleaning Composition | | | |
|---|---|---|---|---|
| | Example No. | | | |
| Component | 29 | 30 | 31 | 32 |
| Val95Asp + Leu126Ser + Asn155Gln | 0.10 | 0.20 | 0.03 | 0.05 |
| Gly65Ser + Gly102Asn + Val203Glu | — | — | 0.02 | 0.05 |
| $C_{12}$ alkyl benzene sulfonate | 12.00 | 12.00 | 12.00 | 12.00 |
| Zeolite A (1–10 micrometer) | 26.00 | 26.00 | 26.00 | 26.00 |
| 2-butyl octanoic acid | 4.00 | 4.00 | 4.00 | 4.00 |
| $C_{12}$–$C_{14}$ secondary (2,3) alkyl sulfate, Na salt | 5.00 | 5.00 | 5.00 | 5.00 |
| Sodium citrate | 5.00 | 5.00 | 5.00 | 5.00 |
| Optical brightener | 0.10 | 0.10 | 0.10 | 0.10 |
| Sodium sulfate | 17.00 | 17.00 | 17.00 | 17.00 |
| Water and minors | balance to 100% | | | |

In Examples 29–30, the BPN' variants recited in Tables 2–25, among others, are substituted for Val95Asp+Leu126Ser+Asn155Gln, with substantially similar results.

In Examples 31–32, any combination of the BPN' variants recited in Tables 2–25, among others, are substituted for Val95Asp+Leu126Ser+Asn155Gln and Gly65Ser+Gly102Asn+Val203Glu, with substantially similar results.

EXAMPLES 33–36

Granular Fabric Cleaning Composition

| Component | \#33 | \#34 | \#35 | \#36 |
|---|---|---|---|---|
| Ser63Glu | 0.10 | 0.20 | 0.03 | 0.05 |
| Leu96Asn + Lys213Asp | — | — | 0.02 | 0.05 |
| $C_{13}$ linear alkyl benzene sulfonate | 22.00 | 22.00 | 22.00 | 22.00 |
| Phosphate (as sodium tripolyphosphates) | 23.00 | 23.00 | 23.00 | 23.00 |
| Sodium carbonate | 23.00 | 23.00 | 23.00 | 23.00 |
| Sodium silicate | 14.00 | 14.00 | 14.00 | 14.00 |
| Zeolite | 8.20 | 8.20 | 8.20 | 8.20 |
| Chelant (diethylaenetriamine-pentaacetic acid) | 0.40 | 0.40 | 0.40 | 0.40 |
| Sodium sulfate | 5.50 | 5.50 | 5.50 | 5.50 |
| Water | \multicolumn{4}{c}{balance to 100%} | | | |

In Examples 33–34, the BPN' variants recited in Tables 2–25, among others, are substituted for Ser63Glu, with substantially similar results.

In Examples 35–36, any combination of the BPN' variants recited in Tables 2–25, among others, are substituted for Ser63Glu and Leu96Asn+Lys213Asp, with substantially similar results.

EXAMPLES 37–40

Granular Fabric Cleaning Composition

| Component | 37 | 38 | 39 | 40 |
|---|---|---|---|---|
| Asn62Ser + Ser163Asp + Phe189Ser + Ala216Glu | 0.10 | 0.20 | 0.03 | 0.05 |
| Gly97Ser + Trp106Ile + Tyr217Leu | — | — | 0.02 | 0.05 |
| $C_{12}$ alkyl benzene sulfonate | 12.00 | 12.00 | 12.00 | 12.00 |
| Zeolite A (1–10 micrometer) | 26.00 | 26.00 | 26.00 | 26.00 |
| 2-butyl octanoic acid | 4.00 | 4.00 | 4.00 | 4.00 |
| $C_{12}$–$C_{14}$ secondary (2,3) alkyl sulfate, Na salt | 5.00 | 5.00 | 5.00 | 5.00 |
| Sodium citrate | 5.00 | 5.00 | 5.00 | 5.00 |
| Optical brightener | 0.10 | 0.10 | 0.10 | 0.10 |
| Sodium sulfate | 17.00 | 17.00 | 17.00 | 17.00 |
| Water and minors | | balance to 100% | | |

In Examples 37–38, the BPN' variants recited in Tables 2–25, among others, are substituted for Asn62Ser+Ser163Asp+Phe189Ser+Ala216Glu, with substantially similar results.

In Examples 39–40, any combination of the BPN' variants recited in Tables 2–25, among others, are substituted for Asn62Ser+Ser163Asp+Phe189Ser+Ala216Glu and Gly97Ser+Trp106Ile+Tyr217Leu, with substantially similar results.

EXAMPLES 41–42

Examples 41–42
Granular Fabric Cleaning Composition

| Component | 41 | 42 |
|---|---|---|
| Linear alkyl benzene sulphonate | 11.4 | 10.70 |
| Tallow alkyl sulphate | 1.80 | 2.40 |
| $C_{14-15}$ alkyl sulphate | 3.00 | 3.10 |
| $C_{14-15}$ alcohol 7 times ethoxylated | 4.00 | 4.00 |
| Tallow alcohol 11 times ethoxylated | 1.80 | 1.80 |
| Dispersant | 0.07 | 0.1 |
| Silicone fluid | 0.80 | 0.80 |
| Trisodium citrate | 14.00 | 15.00 |
| Citric acid | 3.00 | 2.50 |
| Zeolite | 32.50 | 32.10 |
| Maleic acid acrylic acid copolymer | 5.00 | 5.00 |
| Diethylene triamine penta methylene phosphonic acid | 1.00 | 0.20 |
| Ala98Asp + Ala187Ser | 0.30 | 0.30 |
| Lipase | 0.36 | 0.40 |
| Amylase | 0.30 | 0.30 |
| Sodium silicate | 2.00 | 2.50 |
| Sodium sulphate | 3.50 | 5.20 |
| Polyvinyl pyrrolidone | 0.30 | 0.50 |
| Perborate | 0.5 | 1 |
| Phenol sulphonate | 0.1 | 0.2 |
| Peroxidase | 0.1 | 0.1 |
| Minors | Up to 100 | Up to 100 |

EXAMPLES 43–44

Examples 43–44
Granular Fabric Cleaning Composition

| Component | 43 | 44 |
|---|---|---|
| Sodium linear $C_{12}$ alkyl benzene-sulfonate | 6.5 | 8.0 |
| Sodium sulfate | 15.0 | 18.0 |
| Zeolite A | 26.0 | 22.0 |
| Sodium nitrilotriacetate | 5.0 | 5.0 |
| Polyvinyl pyrrolidone | 0.5 | 0.7 |
| Tetraacetylethylene diamine | 3.0 | 3.0 |
| Boric acid | 4.0 | — |
| Perborate | 0.5 | 1 |
| Phenol sulphonate | 0.1 | 0.2 |
| Gln59Ser + Asn62Ser + Leu96Gly + Ser204Gln | 0.4 | 0.4 |
| Fillers (e.g., silicates; carbonates; perfumes; water) | Up to 100 | Up to 100 |

EXAMPLE 45

Example 45
Compact Granular Fabric Cleaning Composition

| Component | Weight % |
|---|---|
| Alkyl Sulphate | 8.0 |
| Alkyl Ethoxy Sulphate | 2.0 |
| Mixture of $C_{25}$ and $C_{45}$ alcohol 3 and 7 times ethoxylated | 6.0 |

Example 45
Compact Granular Fabric Cleaning Composition

| Component | Weight % |
| --- | --- |
| Polyhydroxy fatty acid amide | 2.5 |
| Zeolite | 17.0 |
| Layered silicate/citrate | 16.0 |
| Carbonate | 7.0 |
| Maleic acid acrylic acid copolymer | 5.0 |
| Soil release polymer | 0.4 |
| Carboxymethyl cellulose | 0.4 |
| Poly(4-vinylpyridine)-N-oxide | 0.1 |
| Copolymer of vinylimidazole and vinylpyrrolidone | 0.1 |
| PEG2000 | 0.2 |
| Val95Gln + Tyr104Glu + Gly127Gln + Lys213Glu + Ala216Asp | 0.5 |
| Lipase | 0.2 |
| Cellulase | 0.2 |
| Tetracetylethylene diamine | 6.0 |
| Percarbonate | 22.0 |
| Ethylene diamine disuccinic acid | 0.3 |
| Suds suppressor | 3.5 |
| Disodium-4,4'-bis(2-morpholino-4-anilino-s-triazin-6-ylamino)stilbene-2,2'-disulphonate | 0.25 |
| Disodium-4,4'-bis(2-sulfostyril)biphenyl | 0.05 |
| Water, Perfume and Minors | Up to 100 |

EXAMPLE 46

Example 46
Granular Fabric Cleaning Composition

| Component | Weight % |
| --- | --- |
| Linear alkyl benzene sulphonate | 7.6 |
| $C_{16}$–$C_{18}$ alkyl sulfate | 1.3 |
| $C_{14-15}$ alcohol 7 times ethoxylated | 4.0 |
| Coco-alkyl-dimethyl hydroxyethyl ammonium chloride | 1.4 |
| Dispersant | 0.07 |
| Silicone fluid | 0.8 |
| Trisodium citrate | 5.0 |
| Zeolite 4A | 15.0 |
| Maleic acid acrylic acid copolymer | 4.0 |
| Diethylene triamine penta methylene phosphonic acid | 0.4 |
| Perborate | 15.0 |
| Tetraacetylethylene diamine | 5.0 |
| Smectite clay | 10.0 |
| Poly (oxy ethylene) (MW 300,000) | 0.3 |
| Ser63Glu + Thr104Asn + Gln206Ser + Tyr217Thr | 0.4 |
| Lipase | 0.2 |
| Amylase | 0.3 |
| Cellulase | 0.2 |
| Sodium silicate | 3.0 |
| Sodium carbonate | 10.0 |
| Carboxymethyl cellulose | 0.2 |
| Brighteners | 0.2 |
| Water, perfume and minors | Up to 100 |

EXAMPLE 47

Example 47
Granular Fabric Cleaning Composition

| Component | Weight % |
| --- | --- |
| Linear alkyl benzene sulfonate | 6.92 |
| Tallow alkyl sulfate | 2.05 |
| $C_{14-15}$ alcohol 7 times ethoxylated | 4.4 |
| $C_{12-15}$ alkyl ethoxy sulfate - 3 times ethoxylated | 0.16 |
| Zeolite | 20.2 |
| Citrate | 5.5 |
| Carbonate | 15.4 |
| Silicate | 3.0 |
| Maleic acid acrylic acid copolymer | 4.0 |
| Carboxymethyl Cellulase | 0.31 |
| Soil release polymer | 0.30 |
| Asn62Ser + Trp106Gly + Ser132Asp + Ala187Ser + Phe189Ser | 0.2 |
| Lipase | 0.36 |
| Cellulase | 0.13 |
| Perborate tetrahydrate | 11.64 |
| Perborate monohydrate | 8.7 |
| Tetraacetylethylene diamine | 5.0 |
| Diethylene tramine penta methyl phosphonic acid | 0.38 |
| Magnesium, sulfate | 0.40 |
| Brightener | 0.19 |
| Perfume, silicone, suds suppressors | 0.85 |
| Minors | Up to 100 | b. Liquid Fabric Cleaning Compositions

Liquid fabric cleaning compositions of the present invention comprise an effective amount of one or more enzyme variants of the present invention, preferably from about 0.005% to about 5%, more preferably from about 0.01% to about 1%, by weight of active enzyme of the composition. Such liquid fabric cleaning compositions typically additionally comprise an anionic surfactant, a fatty acid, a water-soluble detergency builder and water.

The liquid fabric cleaning composition embodiment of the present invention is illustrated by the following examples.

EXAMPLES 48–52

Examples 48–52
Liquid Fabric Cleaning Compositions

| Component | Example No. | | | | |
| --- | --- | --- | --- | --- | --- |
| | 48 | 49 | 50 | 51 | 52 |
| Ser161Glu + Gly219Asn | 0.05 | 0.03 | 0.30 | 0.03 | 0.10 |
| Asn62Ser + Ile107Ala + Glu206Asp + Tyr217Thr | — | — | — | 0.01 | 0.20 |
| $C_{12}$–$C_{14}$ alkyl sulfate, Na | 20.00 | 20.00 | 20.00 | 20.00 | 20.00 |
| 2-butyl octanoic acid | 5.00 | 5.00 | 5.00 | 5.00 | 5.00 |
| Sodium citrate | 1.00 | 1.00 | 1.00 | 1.00 | 1.00 |
| $C_{10}$ alcohol ethoxylate (3) | 13.00 | 13.00 | 13.00 | 13.00 | 13.00 |
| Monethanolamine | 2.50 | 2.50 | 2.50 | 2.50 | 2.50 |
| Water/propylene glycol/ethanol (100:1:1) | balance to 100% | | | | |

In Examples 48–50 the BPN' variants recited in Tables 2–25, among others, are substituted for Ser161Glu+Gly219Asn, with substantially similar results.

In Examples 51–52, any combination of the BPN' variants recited in Tables 2–25, among others, are substituted for Ser161Glu+Gly219Asn and Asn62Ser+Ile107Ala+Glu206Asp+Tyr217Thr, with substantially similar results.

EXAMPLES 53–57

Examples 53–57
Liquid Fabric Cleaning Compositions

| Component | \multicolumn{5}{c}{Example No.} | | | | |
|---|---|---|---|---|---|
| | 53 | 54 | 55 | 56 | 57 |
| Ser101Asp + Ile107Ala + Gly202Ser | 0.05 | 0.03 | 0.30 | 0.03 | 0.10 |
| Val95Thr + Thr208Gly | — | — | — | 0.01 | 0.20 |
| $C_{12}$–$C_{14}$ alkyl sulfate, Na | 20.00 | 20.00 | 20.00 | 20.00 | 20.00 |
| 2-butyl octanoic acid | 5.00 | 5.00 | 5.00 | 5.00 | 5.00 |
| Sodium citrate | 1.00 | 1.00 | 1.00 | 1.00 | 1.00 |
| $C_{10}$ alcohol ethoxylate (3) | 13.00 | 13.00 | 13.00 | 13.00 | 13.00 |
| Monethanolamine | 2.50 | 2.50 | 2.50 | 2.50 | 2.50 |
| Water/propylene glycol/ethanol (100:1:1) | \multicolumn{5}{c}{balance to 100%} | | | | |

In Examples 53–55 the BPN' variants recited in Tables 2–25, among others, are substituted for Ser101Asp+Ile107Ala+Gly202Ser, with substantially similar results.

In Examples 56–57, any combination of the BPN' variants recited in Tables 212, among others, are substituted for Ser101Asp+Ile 107Ala+Gly202Ser and Val95Thr+Thr208Gly, with substantially similar results.

EXAMPLES 58–59

Examples 58–59
Granular Fabric Cleaning Composition

| Component | Example No. | |
|---|---|---|
| | 58 | 59 |
| $C_{12-14}$ alkenyl succinic acid | 3.0 | 8.0 |
| Citric acid monohydrate | 10.0 | 15.0 |
| Sodium $C_{12-15}$ alkyl sulphate | 8.0 | 8.0 |
| Sodium sulfate of $C_{12-15}$ alcohol 2 times ethoxylated | — | 3.0 |
| $C_{12-15}$ alcohol 7 times ethoxylated | — | 8.0 |
| $C_{12-15}$ alcohol 5 times ethoxylated | 8.0 | — |
| Diethylene triamine penta (methylene phosphonic acid) | 0.2 | — |
| Oleic acid | 1.8 | — |
| Ethanol | 4.0 | 4.0 |
| Propanediol | 2.0 | 2.0 |
| Asp60Glu + Gln206Asn | 0.2 | 0.2 |
| Polyvinyl pyrrolidone | 1.0 | 2.0 |
| Suds suppressor | 0.15 | 0.15 |
| NaOH | \multicolumn{2}{c}{up to pH 7.5} | |
| Perborate | 0.5 | 1 |
| Phenol sulphonate | 0.1 | 0.2 |
| Peroxidase | 0.4 | 0.1 |
| Waters and minors | \multicolumn{2}{c}{up to 100 parts} | |

In each of Examples 58 and 59 herein, the BPN' variants recited in Tables 2–25, among others, are substituted for Asp60Glu+Gln206Asn, with substantially similar results.

EXAMPLES 60–62

Examples 60–62
Liquid Fabric Cleaning Composition

| Component | Example No. | | |
|---|---|---|---|
| | 60 | 61 | 62 |
| Citric Acid | 7.10 | 3.00 | 3.00 |
| Fatty Acid | 2.00 | — | 2.00 |
| Ethanol | 1.93 | 3.20 | 3.20 |
| Boric Acid | 2.22 | 3.50 | 3.50 |
| Monoethanolamine | 0.71 | 1.09 | 1.09 |
| 1,2 Propanediol | 7.89 | 8.00 | 8.00 |
| NaCumene Sulfonate | 1.80 | 3.00 | 3.00 |
| NaFormate | 0.08 | 0.08 | 0.08 |
| NaOH | 6.70 | 3.80 | 3.80 |
| Silicon anti-foam agent | 1.16 | 1.18 | 1.18 |
| Asn61Glu | 0.0145 | — | — |
| Gly97Glu + Thr164Pro | — | 0.0145 | — |
| Asn62Glu + Thr158Ser + Gly215Ser | — | — | 0.0145 |
| Lipase | 0.200 | 0.200 | 0.200 |
| Cellulase | — | 7.50 | 7.50 |
| Soil release polymer | 0.29 | 0.15 | 0.15 |
| Anti-foaming agents | 0.06 | 0.085 | 0.085 |
| Brightener 36 | 0.095 | — | — |
| Brightener 3 | — | 0.05 | 0.05 |
| $C_{12}$ alkyl benzenesulfonic acid | 9.86 | — | — |
| $C_{12-15}$ alkyl polyethoxylate (2.5) sulfate | 13.80 | 18.00 | 18.00 |
| $C_{12}$ glucose amide | — | 5.00 | 5.00 |
| $C_{12-13}$ alkyl polyethoxylate (9) | 2.00 | 2.00 | 2.00 |
| Water, perfume and minors | \multicolumn{3}{c}{balance to 100%} | | | c. Bar Fabric Cleaning Compositions

Bar fabric cleaning compositions of the present invention suitable for hand-washing soiled fabrics contain an effective amount of one or more enzyme variants of the present invention, preferably from about 0.001% to about 10%, more preferably from about 0.01% to about 1% by weight of the composition.

The bar fabric cleaning composition embodiment of the present invention is illustrated by the following examples.

EXAMPLES 63–66

Examples 63–66
Bar Fabric Cleaning Compositions

| Component | Example No. | | | |
|---|---|---|---|---|
| | 63 | 64 | 65 | 66 |
| Gly97Glu + Thr164Pro | 0.3 | — | 0.1 | 0.02 |
| Ala98Ser + Gly154Asn | — | — | 0.4 | 0.03 |
| $C_{12}$–$C_{16}$ alkyl sulfate, Na | 20.0 | 20.0 | 20.0 | 20.00 |
| $C_{12}$–$C_{14}$ N-methyl glucamide | 5.0 | 5.0 | 5.0 | 5.00 |
| $C_{11}$–$C_{13}$ alkyl benzene sulfonate, Na | 10.0 | 10.0 | 10.0 | 10.00 |
| Sodium carbonate | 25.0 | 25.0 | 25.0 | 25.00 |
| Sodium pyrophosphate | 7.0 | 7.0 | 7.0 | 7.00 |
| Sodium tripolyphosphate | 7.0 | 7.0 | 7.0 | 7.00 |
| Zeolite A (0.1–10µ) | 5.0 | 5.0 | 5.0 | 5.00 |
| Carboxymethylcellulose | 0.2 | 0.2 | 0.2 | 0.20 |
| Polyacrylate (MW 1400) | 0.2 | 0.2 | 0.2 | 0.20 |
| Coconut monethanolamide | 5.0 | 5.0 | 5.0 | 5.00 |
| Brightener, perfume | 0.2 | 0.2 | 0.2 | 0.20 |
| $CaSO_4$ | 1.0 | 1.0 | 1.0 | 1.00 |

-continued

Examples 63–66
Bar Fabric Cleaning Compositions

| | Example No. | | | |
|---|---|---|---|---|
| Component | 63 | 64 | 65 | 66 |
| MgSO$_4$ | 1.0 | 1.0 | 1.0 | 1.00 |
| Water | 4.0 | 4.0 | 4.0 | 4.00 |
| Filler* | | balance to 100% | | |

*Can be selected from convenient materials such as CaCO$_3$, talc, clay, silicates, and the like.

In Examples 63–64 the BPN' variants recited in Tables 2–25, among others, are substituted for Gly97Glu+Thr164Pro, with substantially similar results.

In Examples 65–66, any combination of the BPN' variants recited in Tables 2–25, among others, are substituted for Gly97Glu+Ghr164Pro and Ala98Ser+Gly154Asn, with substantially similar results.

EXAMPLES 67–70

Examples 67–70
Bar Fabric Cleaning Compositions

| | Example No. | | | |
|---|---|---|---|---|
| Component | 67 | 68 | 69 | 70 |
| Val203Glu | 0.3 | — | 0.1 | 0.02 |
| Gly100Glu + Ile107Ser | — | 0.3 | 0.4 | 0.03 |
| C$_{12}$–C$_{16}$ alkyl sulfate, Na | 20.0 | 20.0 | 20.0 | 20.00 |
| C$_{12}$–C$_{14}$ N-methyl glucamide | 5.0 | 5.0 | 5.0 | 5.00 |
| C$_{11}$–C$_{13}$ alkyl benzene sulfonate, Na | 10.0 | 10.0 | 10.0 | 10.00 |
| Sodium carbonate | 25.0 | 25.0 | 25.0 | 25.00 |
| Sodium pyrophosphate | 7.0 | 7.0 | 7.0 | 7.00 |
| Sodium tripolyphosphate | 7.0 | 7.0 | 7.0 | 7.00 |
| Zeolite A (0.1–.10μ) | 5.0 | 5.0 | 5.0 | 5.00 |
| Carboxymethylcellulose | 0.2 | 0.2 | 0.2 | 0.20 |
| Polyacrylate (MW 1400) | 0.2 | 0.2 | 0.2 | 0.20 |
| Coconut monethanolamide | 5.0 | 5.0 | 5.0 | 5.00 |
| Brightener, perfume | 0.2 | 0.2 | 0.2 | 0.20 |
| CaSO$_4$ | 1.0 | 1.0 | 1.0 | 1.00 |
| MgSO$_4$ | 1.0 | 1.0 | 1.0 | 1.00 |
| Water | 4.0 | 4.0 | 4.0 | 4.00 |
| Filler* | | balance to 100% | | |

*Can be selected from convenient materials such as CaCO$_3$, talc, clay, silicates, and the like.

In Example 67, the BPN' variants recited in Tables 2–25, among others, are substituted for Val203Glu, with substantially similar results.

In Example 68, the BPN' variants recited in Tables 2–25, among others, are substituted for Gly100Glu+Ile107Ser, with substantially similar results.

In Examples 69–70, any combination of the BPN' variants recited in Tables 2–25, among others, are substituted for Val203Glu and Gly100Glu+Ile107Ser, with substantially similar results.

B. Additional Cleaning Compositions

In addition to the hard surface cleaning, dishwashing and fabric cleaning compositions discussed above, one or more enzyme variants of the present invention may be incorporated into a variety of other cleaning compositions where hydrolysis of an insoluble substrate is desired. Such additional cleaning compositions include but are not limited to, oral cleaning compositions, denture cleaning compositions, and contact lens cleaning compositions.

1. Oral Cleaning Compositions

In another embodiment of the present invention, a pharmaceutically-acceptable amount of one or more enzyme variants of the present invention are included in compositions useful for removing proteinaceous stains from teeth or dentures. As used herein, "oral cleaning compositions" refers to dentifrices, toothpastes, toothgels, toothpowders, mouthwashes, mouth sprays, mouth gels, chewing gums, lozenges, sachets, tablets, biogels, prophylaxis pastes, dental treatment solutions, and the like. Preferably, the oral cleaning compositions comprise from about 0.0001% to about 20% of one or more enzyme variants of the present invention, more preferably from about 0.001% to about 10%, more preferably still from about 0.01% to about 5%, by weight of the composition, and a pharmaceutically-acceptable carrier. As used herein, "pharmaceutically-acceptable" means that drugs, medicaments or inert ingredients which the term describes are suitable for use in contact with the tissues of humans and lower animals without undue toxicity, incompatibility, instability, irritation, allergic response, and the like, commensurate with a reasonable benefit/risk ratio.

Typically, the pharmaceutically-acceptable oral cleaning carrier components of the oral cleaning components of the oral cleaning compositions will generally comprise from about 50% to about 99.99%, preferably from about 65% to about 99.99%, more preferably from about 65% to about 99%, by weight of the composition.

The pharmaceutically-acceptable carrier components and optional components which may be included in the oral cleaning compositions of the present invention are well known to those skilled in the art. A wide variety of composition types, carrier components and optional components useful in the oral cleaning compositions are disclosed in U.S. Pat. No. 5,096,700, Seibel, issued Mar. 17, 1992; U.S. Pat. No. 5,028,414, Sampathkumar, issued Jul. 2, 1991; and U.S. Pat. No. 5,028,415, Benedict, Bush and Sunberg, issued Jul. 2, 1991; all of which are incorporated herein by reference.

The oral cleaning composition embodiment of the present invention is illustrated by the following examples.

EXAMPLES 71–74

Examples 71–74
Dentifrice Composition

| | Example No. | | | |
|---|---|---|---|---|
| Component | 71 | 72 | 73 | 74 |
| Gln59Asp + Ala98Glu + Gly102Asp + Ser105Glu + Leu109Thr | 2.000 | 3.500 | 1.500 | 2.000 |
| Sorbitol (70% aqueous solution) | 35.000 | 35.000 | 35.000 | 35.000 |
| PEG-6* | 1.000 | 1.000 | 1.000 | 1.000 |
| Silica dental abrasive** | 20.000 | 20.000 | 20.000 | 20.000 |
| Sodium fluoride | 0.243 | 0.243 | 0.243 | 0.243 |
| Titanium dioxide | 0.500 | 0.500 | 0.500 | 0.500 |
| Sodium saccharin | 0.286 | 0.286 | 0.286 | 0.286 |
| Sodium alkyl sulfate (27.9% aqueous solution) | 4.000 | 4.000 | 4.000 | 4.000 |
| Flavor | 1.040 | 1.040 | 1.040 | 1.040 |

-continued

Examples 71–74
Dentifrice Composition

| Component | Example No. | | | |
|---|---|---|---|---|
| | 71 | 72 | 73 | 74 |
| Carboxyvinyl Polymer*** | 0.300 | 0.300 | 0.300 | 0.300 |
| Carrageenan**** | 0.800 | 0.800 | 0.800 | 0.800 |
| Water | balance to 100% | | | |

*PEG-6 = Polyethylene glycol having a molecular weight of 600.
**Precipitated silica identified as Zeodent 119 offered by J. M. Huber.
***Carbopol offered by B. F. Goodrich Chemical Company.
****Iota Carrageenan offered by Hercules Chemical Company.

In Examples 71–74 the BPN' variants recited in Tables 2–25, among others, are substituted for Gln59Asp+Ala98Glu+Gly102Asp+Ser105Glu+Leu209Thr, with substantially similar results.

EXAMPLES 75–78

Examples 75–78
Mouthwash Composition

| Component | Example No. | | | |
|---|---|---|---|---|
| | 75 | 76 | 77 | 78 |
| Leu96Thr + Gly128Asp + Ala133Glu + Asn155Glu + Lys213Asp + Ala216GAsp | 3.00 | 7.50 | 1.00 | 5.00 |
| SDA 40 Alcohol | 8.00 | 8.00 | 8.00 | 8.00 |
| Flavor | 0.08 | 0.08 | 0.08 | 0.08 |
| Emulsifier | 0.08 | 0.08 | 0.08 | 0.08 |
| Sodium Fluoride | 0.05 | 0.05 | 0.05 | 0.05 |
| Glycerin | 10.00 | 10.00 | 10.00 | 10.00 |
| Sweetener | 0.02 | 0.02 | 0.02 | 0.02 |
| Benzoic acid | 0.05 | 0.05 | 0.05 | 0.05 |
| Sodium hydroxide | 0.20 | 0.20 | 0.20 | 0.20 |
| Dye | 0.04 | 0.04 | 0.04 | 0.04 |
| Water | balance to 100% | | | |

In Examples 75–78, the BPN' variants recited in Tables 2–25, among others, are substituted for Leu96Thr+Gly128Asp+Ala133Glu+Asn155Glu+Lys213Asp+Ala216Asp, with substantially similar results.

EXAMPLES 79–82

Examples 79–82
Lozenge Composition

| Component | Example No. | | | |
|---|---|---|---|---|
| | 79 | 80 | 81 | 82 |
| Ser132Asp + Tyr217Leu | 0.01 | 0.03 | 0.10 | 0.02 |
| Sorbitol | 17.50 | 17.50 | 17.50 | 17.50 |
| Mannitol | 17.50 | 17.50 | 17.50 | 17.50 |
| Starch | 13.60 | 13.60 | 13.60 | 13.60 |
| Sweetener | 1.20 | 1.20 | 1.20 | 1.20 |
| Flavor | 11.70 | 11.70 | 11.70 | 11.70 |
| Color | 0.10 | 0.10 | 0.10 | 0.10 |
| Corn Syrup | balance to 100% | | | |

In Examples 79–82, the BPN' variants recited in Tables 2–25, among others, are substituted for Ser132Asp+Tyr217Leu, with substantially similar results.

EXAMPLES 83–86

Examples 83–86
Chewing Gum Composition

| Component | Example No. | | | |
|---|---|---|---|---|
| | 83 | 84 | 85 | 86 |
| Thr66Pro + Gln103Asn + Lys213Asp | 0.03 | 0.02 | 0.10 | 0.05 |
| Sorbitol crystals | 38.44 | 38.40 | 38.40 | 38.40 |
| Paloja-T gum base* | 20.00 | 20.00 | 20.00 | 20.00 |
| Sorbitol (70% aqueous solution) | 22.00 | 22.00 | 22.00 | 22.00 |
| Mannitol | 10.00 | 10.00 | 10.00 | 10.00 |
| Glycerine | 7.56 | 7.56 | 7.56 | 7.56 |
| Flavor | 1.00 | 1.00 | 1.00 | 1.00 |

*Supplied by L. A. Dreyfus Company.

In Examples 83–86, the BPN' variants recited in Tables 2–25, among others, are substituted for Thr66Pro+Gln103Asn+Lys213Asp, with substantially similar results.

2. Denture Cleaning Compositions

In another embodiment of the present invention, denture cleaning compositions for cleaning dentures outside of the oral cavity comprise one or more enzyme variants of the present invention. Such denture cleaning compositions comprise an effective amount of one or more of the enzyme variants, preferably from about 0.0001% to about 50% of one or more of the enzyme variants, more preferably from about 0.001% to about 35%, more preferably still from about 0.01% to about 20%, by weight of the composition, and a denture cleansing carrier. Various denture cleansing composition formats such as effervescent tablets and the like are well known in the art (see for example U.S. Pat. No. 5,055,305, Young, incorporated herein by reference), and are generally appropriate for incorporation of one or more of the enzyme variants for removing proteinaceous stains from dentures.

The denture cleaning composition embodiment of the present invention is illustrated by the following examples.

EXAMPLES 87–90

Examples 87–90
Two-layer Effervescent Denture Cleansing Tablet

| Component | Example No. | | | |
|---|---|---|---|---|
| | 87 | 88 | 89 | 90 |
| Acidic Layer | | | | |
| Gln59Glu + Ser63Glu + Val95Met + Gly97Pro + Tyr217Ala | 1.0 | 1.5 | 0.01 | 0.05 |
| Tartaric acid | 24.0 | 24.0 | 24.00 | 24.00 |
| Sodium carbonate | 4.0 | 4.0 | 4.00 | 4.00 |
| Sulphamic acid | 10.0 | 10.0 | 10.00 | 10.00 |
| PEG 20,000 | 4.0 | 4.0 | 4.00 | 4.00 |
| Sodium bicarbonate | 24.5 | 24.5 | 24.50 | 24.50 |
| Potassium persulfate | 15.0 | 15.0 | 15.00 | 15.00 |
| Sodium acid pyrophosphate | 7.0 | 7.0 | 7.00 | 7.00 |
| Pyrogenic silica | 2.0 | 2.0 | 2.00 | 2.00 |
| TAED* | 7.0 | 7.0 | 7.00 | 7.00 |
| Ricinoleylsulfosuccinate | 0.5 | 0.5 | 0.50 | 0.50 |
| Flavor | 1.0 | 1.0 | 1.00 | 1.00 |

-continued

Examples 87–90
Two-layer Effervescent Denture Cleansing Tablet

| | Example No. | | | |
|---|---|---|---|---|
| Component | 87 | 88 | 89 | 90 |
| Alkaline Layer | | | | |
| Sodium perborate monohydrate | 32.0 | 32.0 | 32.00 | 32.00 |
| Sodium bicarbonate | 19.0 | 19.0 | 19.00 | 19.00 |
| EDTA | 3.0 | 3.0 | 3.00 | 3.00 |
| Sodium tripolyphosphate | 12.0 | 12.0 | 12.00 | 12.00 |
| PEG 20,000 | 2.0 | 2.0 | 2.00 | 2.00 |
| Potassium persulfate | 26.0 | 26.0 | 26.00 | 26.00 |
| Sodium carbonate | 2.0 | 2.0 | 2.00 | 2.00 |
| Pyrogenic silica | 2.0 | 2.0 | 2.00 | 2.00 |
| Dye/flavor | 2.0 | 2.0 | 2.00 | 2.00 |

*Tetraacetylethylene diamine

In Examples 87–90, the BPN' variants recited in Tables 2–25, among others, are substituted for Gln59Glu+Ser63Glu+Val95Met+Gly97Pro+Tyr217Ala, with substantially similar results.

3. Contact Lens Cleaning Compositions

In another embodiment of the present invention, contact lens cleaning compositions comprise one or more enzyme variants of the present invention. Such contact lens cleaning compositions comprise an effective amount of one or more of the enzyme variants, preferably from about 0.01% to about 50% of one or more of the enzyme variants, more preferably from about 0.01% to about 20%, more preferably still from about 1% to about 5%, by weight of the composition, and a contact lens cleaning carrier. Various contact lens cleaning composition formats such as tablets, liquids and the like are well known in the art (see for example U.S. Pat. No. 4,863,627, Davies, Meaken and Rees, issued Sep. 5, 1989; U.S. Pat. Re. 32,672, Huth, Lam and Kirai, reissued May 24, 1988; U.S. Pat. No. 4,609,493, Schäfer, issued Sep. 2, 1986; U.S. Pat. No. 4,690,793, Ogunbiyi and Smith, issued Sep. 1, 1987; U.S. Pat. No. 4,614,549, Ogunbiyi, Riedhammer and Smith, issued Sep. 30, 1986; and U.S. Pat. No. 4,285,738, Ogata, issued Aug. 25, 1981; each of which are incorporated herein by reference), and are generally appropriate for incorporation of one or more enzyme variants of the present invention for removing proteinaceous stains from contact lens.

The contact lens cleaning composition embodiment of the present invention is illustrated by the following examples.

EXAMPLES 91–94

Enzymatic Contact Lens Cleaning Solution

| | Example No. | | | |
|---|---|---|---|---|
| Component | 91 | 92 | 93 | 94 |
| Ser191Glu + Gly219Ser | 0.01 | 0.5 | 0.1 | 2.0 |
| Glucose | 50.00 | 50.0 | 50.0 | 50.0 |
| Nonionic surfactant (polyoxyethlene-polyoxypropylene copolymer) | 2.00 | 2.0 | 2.0 | 2.0 |
| Anionic surfactant (polyoxyethylene-alkylphenylether sodium sulfricester) | 1.00 | 1.0 | 1.0 | 1.0 |
| Sodium chloride | 1.00 | 1.0 | 1.0 | 1.0 |
| Borax | 0.30 | 0.3 | 0.3 | 0.3 |
| Water | balance to 100% | | | |

In Examples 91–94, the BPN' variants recited in Tables 2–25, among others, are substituted for Ser191Glu+Gly219Ser, with substantially similar results.

While particular embodiments of the subject invention have been described, it will be obvious to those skilled in the art that various changes and modifications of the subject invention can be made without departing from the spirit and scope of the invention. It is intended to cover, in the appended claims, all such modifications that are within the scope of the invention.

What is claimed is:

1. An isolated BPN' variant having a modified amino acid sequence of the Subtilisin BPN' wild-type amino acid sequence set forth in SEQ ID NO:1, the wild-type amino acid sequence comprising a first loop region, a second loop region, a third loop region, a fourth loop region and a fifth loop region; wherein the modified amino acid sequence comprises a substitution at one or more positions in one of the loop regions; wherein A. when the substitution occurs in the first loop region, the substitution occurs at one of positions 59, 61, 62, 63, 65 or 66; wherein
  a. when a substitution occurs at position 59, the substituting amino acid is Asn or Asp;
  b. when a substitution occurs at position 61, the substituting amino acid is Gln;
  c. when a substitution occurs at position 62, the substituting amino acid is Gln;
  d. when a substitution occurs at position 63, the substituting amino acid is Glu;
  e. when a substitution occurs at position 65, the substituting amino acid is Asn, Asp, Gln, Glu, Pro or Ser; and
  f. when a substitution occurs at position 66, the substituting amino acid is Asn, Asp, Gln, Glu, Pro or Ser;

B. when the substitution occurs in the second loop region, the substitution occurs at one of positions 95, 96, 97, 98, 100, 102, 103, 106 or 107; wherein
  a. when a substitution occurs at position 95, the substituting amino acid is Ala, Asn, Asp, Gln, Glu, Gly, His, Pro, Ser or Thr;
  b. when a substitution occurs at position 96, the substituting amino acid is Ala, Asn, Gln, Glu, Gly, His, Ile, Pro, Ser, Thr or Val;
  c. when a substitution occurs at position 97, the substituting amino acid is Gln, Pro or Ser;
  d. when a substitution occurs at position 98, the substituting amino acid is Asn, Gln, Gly, His, Ser or Thr;
  e. when a substitution occurs at position 100, the substituting amino acid is Asn, Gln, Pro or Ser;
  f. when a substitution occurs at position 102, the substituting amino acid is Asn, Asp, Gln, Glu, Pro or Ser;

g. when a substitution occurs at position 103, the substituting amino acid is Asn;
h. when a substitution occurs at position 106, the substituting amino acid is Cys or Met; and
i. when a substitution occurs at position 107, the substituting amino acid is Gln, His, or Thr;

C. when the substitution occurs in the third loop region, the substitution occurs at one of positions 126, 127, 129, 131, 132 or 133; wherein
  a. when a substitution occurs at position 126, the substituting amino acid is Asn, Asp, Gln, Glu, His, Pro, Ser, or Thr;
  b. when a substitution occurs at position 127, the substituting amino acid is Pro;
  c. when a substitution occurs at position 129, the substituting amino acid is Asn, Gln, or Ser;
  d. when a substitution occurs at position 131, the substituting amino acid is Asn, Gln, or Ser;
  e. when a substitution occurs at position 132, the substituting amino acid is Asp or Glu; and
  f. when a substitution occurs at position 133, the substituting amino acid is Asn, Asp, Gln, Glu, Gly, His, Pro, Ser or Thr;

D. when the substitution occurs in the fourth loop region the substitution occurs at one of positions 154, 157, 158, 160, 164, or 167; wherein
  a. when a substitution occurs at position 154, the substituting amino acid is Asn, Asp, Gln, Glu, Pro or Ser;
  b. when a substitution occurs at position 157, the substituting amino acid is Asn, Asp, Gln, Glu, Pro or Ser;
  c. when a substitution occurs at position 158, the substituting amino acid is Asn, Gln, Pro or Ser;
  d. when a substitution occurs at position 160, the substituting amino acid is Asn, Gln or Pro;
  e. when a substitution occurs at position 164, the substituting amino acid is Asn, Gln, Pro, or Ser; and
  f. when a substitution occurs at position 167, the substituting amino acid is His, Ile, Leu, or Pro;

E. when the substitution occurs in the fifth loop region, the substitution occurs at one of positions 187, 190 or; wherein
  a. when a substitution occurs at position 187, the substituting amino acid is Asn, Asp, Gln, Glu, Gly, His, Pro, Ser and Thr; and
  b. when a substitution occurs at position 190, the substituting amino acid is Asp or Glu;

whereby the BPN' variant has decreased adsorption to, and increased hydrolysis of, an insoluble substrate as compared to wild-type subtilisin BPN' and wherein an amino acid substitution at the subtilisin BPN' positions 59, 95, 96 or 187 is combined with at least one further substitution at a corresponding position selected from subtilisin BPN' positions 60, 61, 65, 66, 105, 106, 130, 132, 133, 188, 190, 200, 201, 202, 203, 205, 207, 210, 211, 212, 216 and 220.

2. The BPN' variant of claim 1, wherein the substitution occurs in the first loop region.

3. The BPN' variant of claim 1, wherein the substitution occurs in the second loop region.

4. The BPN' variant of claim 1, wherein the substitution occurs in the third loop region.

5. The BPN' variant of claim 1, wherein the substitution occurs in the fourth loop region.

6. The BPN' variant of claim 1, wherein the substitution occurs in the fifth loop region.

7. The BPN' variant of claim 1, wherein the wild-type amino acid sequence further comprises a sixth loop region, wherein the modified amino acid sequence further comprises one or more substitutions in the sixth loop region; wherein the substitution(s) in the sixth loop region occurs at one or more of positions 199, 200, 201, 202, 203, 204, 205, 206, 207, 208, 209, 210, 211, 212, 213, 214, 215, 216, 218, 219 or 220; wherein
  a. when a substitution occurs at position 199, the substituting amino acid is Cys, Ala, His, Thr, Pro, Gly, Gln, Asn, Ser, Asp or Glu;
  b. when a substitution occurs at position 200, the substituting amino acid is His, Thr, Pro, Gly, Gln, Asn, Ser, Asp or Glu;
  c. when a substitution occurs at position 201, the substituting amino acid is Gly, Gln, Asn, Ser, Asp or Glu;
  d. when a substitution occurs at position 202, the substituting amino acid is Pro, Gln, Asn, Ser, Asp or Glu;
  e. when a substitution occurs at position 203, the substituting amino acid is Met, Cys, His, Pro, Gly, Gln, Asn, Ser, Asp or Glu;
  f. when a substitution occurs at position 204, the substituting amino acid is Glu;
  g. when a substitution occurs at position 205, the substituting amino acid is Leu, Met, Cys, Ala, His, Thr, Pro, Gly, Gln, Asn, Ser, Asp or Glu;
  h. when a substitution occurs at position 206, the substituting amino acid is Pro, Asn or Ser;
  i. when a substitution occurs at position 207, the substituting amino acid is Asp or Glu;
  j. when a substitution occurs at position 208, the substituting amino acid is Pro, Gly, Gln, Asn or Ser;
  k. when a substitution occurs at position 209, the substituting amino acid is Ile, Val, Met, Cys, Ala, His, Thr, Pro, Gly, Gln, Asn, Ser, Asp or Glu;
  l. when a substitution occurs at position 210, the substituting amino acid is Gly, Gln, Asn, Ser, Asp or Glu;
  m. when a substitution occurs at position 211, the substituting amino acid is Ala, Pro, Gln, Asn, Ser, Asp or Glu;
  n. when a substitution occurs at position 212, the substituting amino acid is Gln, Ser, Asp or Glu;
  o. when a substitution occurs at position 213, the substituting amino acid is Trp, Phe, Tyr, Leu, Ile, Val, Met, Cys, Ala, His, Pro, Gly, Gln, Asn, Ser or Glu;
  p. when a substitution occurs at position 214, the substituting amino acid is Phe, Leu, Ile, Val, Met, Cys, Ala, His, Pro, Gly, Gln or Asn;
  q. when a substitution occurs at position 215, the substituting amino acid is Thr, Pro, Gln, Asn, Ser, Asp or Glu;
  r. when a substitution occurs at position 216, the substituting amino acid is His, Thr, Pro, Gly, Gln, Asn, Ser, Asp or Glu;
  s. when a substitution occurs at position 218, the substituting amino acid is Glu;
  t. when a substitution occurs at position 219, the substituting amino acid is Pro, Gln, Asn, Ser, Asp or Glu; and
  u. when a substitution occurs at position 220, the substituting amino acid is Pro, Gly, Gln, Asn, Asp or Glu;

whereby the BPN' variant has decreased adsorption to, and increased hydrolysis of, an insoluble substrate as compared to wild-type subtilisin BPN' and wherein an amino acid substitution at the subtilisin BPN' position 204 is combined with at least one further substitution at a corresponding position selected from subtilisin BPN' positions 60, 61, 65, 66, 105, 106, 130, 132, 133, 188, 190, 200, 201, 202, 203, 205, 207, 210, 211, 212, 216 and 220.

8. An isolated BPN' variant having a modified amino acid sequence of the Subtilisin BPN' wild-type amino acid sequence set forth in SEQ ID NO:1, the wild-type amino acid sequence comprising a first loop region, a second loop region, a third loop region, a fourth the loop region and a fifth loop region; wherein the modified amino acid sequence comprises a substitution at two or more positions in one or more of the loop regions; wherein A. when a substitution occurs in the first loop region, the substitution occurs at one or more of positions 59, 60, 61, 62, 63, 65 or 66; wherein
  a. when a substitution occurs at position 59, the substituting amino acid is Asn, Asp, Glu or Ser;
  b. when a substitution occurs at position 60, the substituting amino acid is Glu;
  c. when a substitution occurs at position 61, the substituting amino acid is Asp, Gln, Glu or Ser;
  d. when a substitution occurs at position 62, the substituting amino acid is Asp, Gln, Glu or Ser;
  e. when a substitution occurs at position 63, the substituting amino acid is Asp or Glu;
  f. when a substitution occurs at position 65, the substituting amino acid is Asn, Asp, Gln, Glu, Pro or Ser; and
  g. when a substitution occurs at position 66, the substituting amino acid is Asn, Asp, Gln, Glu, Gly, Pro or Ser;

B. when a substitution occurs in the second loop region, the substitution occurs at one or more of positions 95, 96, 97, 98, 99, 100, 101, 102, 103, 104, 105, 106 or 107; wherein
  a. when a substitution occurs at position 95, the substituting amino acid is Ala, Asn, Asp, Cys, Gln, Glu, Gly, His, Met, Pro, Ser or Thr;
  b. when a substitution occurs at position 96, the substituting amino acid is Ala, Asn, Asp, Cys, Gln, Glu, Gly, His, Ile, Met, Pro, Ser, Thr or Val;
  c. when a substitution occurs at position 97, the substituting amino acid is Asn, Asp, Gln, Glu, Pro or Ser; but when position 97 is substituted the variant is not a double, triple, quadruple, or quintuple mutation variant having substitutions at positions selected from the group consisting of 104, 156, 166, and 189;
  d. when a substitution occurs at position 98, the substituting amino acid is Asn, Asp, Gln, Glu, Gly, His, Pro, Ser or Thr; but when position 97 is substituted with Asp and the variant is a double mutation variant, position 98 is not substituted with Asp; and when position 98 is substituted the variant is not a double, triple, quadruple, or quintuple mutation variant having substitutions at positions selected from the group consisting of 104, 156, 166, and 189;
  e. when a substitution occurs at position 99, the substituting amino acid is Glu; but when position 99 is substituted the variant is not a double, triple, quadruple, or quintuple mutation variant having substitutions at positions selected from the group consisting of 104, 156, 166, and 189;
  f. when a substitution occurs at position 100, the substituting amino acid is Asn, Asp, Gln, Glu, Pro or Ser; but when position 100 is substituted the variant is not a double, triple, quadruple, or quintuple mutation variant having substitutions at positions selected from the group consisting of 104, 156, 166, and 189;
  g. when a substitution occurs at position 101, the substituting amino acid is Asp or Glu; but when position 101 is substituted the variant is not a double, triple, quadruple, or quintuple mutation variant having substitutions at positions selected from the group consisting of 104, 156, 166, and 189;
  h. when a substitution occurs at position 102, the substituting amino acid is Asn, Asp, Gln, Glu, Pro or Ser; but when position 102 is substituted the variant is not a double, triple, quadruple, or quintuple mutation variant having substitutions at positions selected from the group consisting of 104, 156, 166, and 189;
  i. when a substitution occurs at position 103, the substituting amino acid is Asn, Asp, Glu or Ser; but when position 103 is substituted the variant is not a double, triple, quadruple, or quintuple mutation variant having substitutions at positions selected from the group consisting of 104, 156, 166, and 189;
  j. when a substitution occurs at position 104, the substituting amino acid is Ala, Asn, Asp, Cys, Gln, Glu, Gly, His, Ile, Leu, Met, Pro, Ser, Thr or Val;
  k. when a substitution occurs at position 105, the substituting amino acid is Asp or Glu;
  l. when a substitution occurs at position 106, the substituting amino acid is Ala, Asn, Asp, Cys, Gln, Glu, Gly, His, Ile, Leu, Met, Phe, Pro, Ser, Thr, Tyr or Val; and
  m. when a substitution occurs at position 107, the substituting amino acid is Ala, Asn, Asp, Cys, Gln, Glu, Gly, His, Leu, Met, Pro, Ser, Thr or Val; but when position 107 is substituted the variant is not a double, triple, quadruple, quintuple, or sextuple mutation variant having substitutions at positions selected from the group consisting of 104, 155, 156, 166, and 189;

C. when a substitution occurs in the third loop region, the substitution occurs at one or more of positions 126, 127, 128, 129, 130, 131, 132 or 133; wherein
  a. when a substitution occurs at position 126, the substituting amino acid is Ala, Asn, Asp, Cys, Gln, Glu, Gly, His, Ile, Met, Pro, Ser, Thr or Val; but when position 126 is substituted the variant is not a double, triple, quadruple, quintuple, or sextuple mutation variant having substitutions at positions selected from the group consisting of 104, 155, 156, 166, and 189;
  b. when a substitution occurs at position 127, the substituting amino acid is Asn, Asp, Gln, Glu, Pro or Ser; but when position 127 is substituted the variant is not a double, triple, quadruple, quintuple, or sextuple mutation variant having substitutions at positions selected from the group consisting of 104, 155, 156, 166, and 189;
  c. when a substitution occurs at position 128, the substituting amino acid is Asn, Asp, Gln, Glu, Gly or Ser; but when position 128 is substituted the variant is not a double, triple, quadruple, quintuple, or sextuple mutation variant having substitutions at positions selected from the group consisting of 104, 155, 156, 166, and 189;
  d. when a substitution occurs at position 129, the substituting amino acid is Asn, Asp, Gln, Glu, Gly or Ser; but when position 129 is substituted the variant is not a double, triple, quadruple, quintuple, or sextuple mutation variant having substitutions at positions selected from the group consisting of 104, 155, 156, 166, and 189;
  e. when a substitution occurs at position 130, the substituting amino acid is Asp or Glu;
  f. when a substitution occurs at position 131, the substituting amino acid is Asn, Asp, Gln, Glu, Gly or Ser;

g. when a substitution occurs at position 132, the substituting amino acid is Asp or Glu; and h. when a substitution occurs at position 133, the substituting amino acid is Asn, Asp, Gln, Glu, Gly, His, Pro, Ser or Thr;

D. when a substitution occurs in the fourth loop region, the substitution occurs at one or more of positions 154, 155, 156, 157, 158, 159, 160, 161, 162, 163, 164, 165, 166 or 167; wherein a. when a substitution occurs at position 154, the substituting amino acid is Asn, Asp, Gln, Glu, Pro or Ser; but when position 154 is substituted the variant is not a double, triple, quadruple, or quintuple mutation variant having substitutions at positions selected from the group consisting of 104, 156, 166, and 189;

b. when a substitution occurs at position 155, the substituting amino acid is Asp, Gln, Glu or Ser;

c. when a substitution occurs at position 156, the substituting amino acid is Asp;

d. when a substitution occurs at position 157, the substituting amino acid is Asn, Asp, Gln, Glu, Pro or Ser; but when position 157 is substituted the variant is not a double, triple, quadruple, or quintuple mutation variant having substitutions at positions selected from the group consisting of 104, 156, 166, and 189;

e. when a substitution occurs at position 158, the substituting amino acid is Asn, Asp, Gln, Glu, Gly, Pro or Ser; but when position 158 is substituted the variant is not a double, triple, quadruple, or quintuple mutation variant having substitutions at positions selected from the group consisting of 104, 156, 166, and 189;

f. when a substitution occurs at position 159, the substituting amino acid is Asp or Glu; but when position 159 is substituted the variant is not a double, triple, quadruple, or quintuple mutation variant having substitutions at positions selected from the group consisting of 104, 156, 166, and 189;

g. when a substitution occurs at position 160, the substituting amino acid is Asn, Asp, Gln, Glu, Pro or Ser; but when position 160 is substituted the variant is not a double, triple, quadruple, or quintuple mutation variant having substitutions at positions selected from the group consisting of 104, 156, 166, and 189;

h. when a substitution occurs at position 161, the substituting amino acid is Asp or Glu; but when position 161 is substituted the variant is not a double, triple, quadruple, or quintuple mutation variant having substitutions at positions selected from the group consisting of 104, 156, 166, and 189;

i. when a substitution occurs at position 162, the substituting amino acid is Asp or Glu; but when position 162 is substituted the variant is not a double, triple, quadruple, or quintuple mutation variant having substitutions at positions selected from the group consisting of 104, 156, 166, and 189;

j. when a substitution occurs at position 163, the substituting amino acid is Asp or Glu; but when position 163 is substituted the variant is not a double, triple, quadruple, or quintuple mutation variant having substitutions at positions selected from the group consisting of 104, 156, 166, and 189;

k. when a substitution occurs at position 164, the substituting amino acid is Asn, Asp, Gln, Glu, Gly, Pro or Ser; but when position 164 is substituted the variant is not a double, triple, quadruple, or quintuple mutation variant having substitutions at positions selected from the group consisting of 104, 156, 166, and 189;

l. when a substitution occurs at position 165, the substituting amino acid is Ala, Asn, Asp, Cys, Gln, Glu, Gly, His, Met, Pro, Ser or Thr; but when position 165 is substituted the variant is not a double, triple, quadruple, or quintuple mutation variant having substitutions at positions selected from the group consisting of 104, 156, 166, and 189;

m. when a substitution occurs at position 166, the substituting amino acid is Asn, Asp, Gln, Glu, Pro or Ser; and n. when a substitution occurs at position 167, the substituting amino acid is Ala, Asn, Asp, Cys, Gln, Glu, Gly, His, Ile, Leu, Met, Pro, Ser, Thr or Val; but when position 167 is substituted the variant is not a double, triple, quadruple, or quintuple mutation variant having substitutions at positions selected from the group consisting of 104, 156, 166, and 189; and E. when a substitution occurs in the fifth loop region, the substitution occurs at one or more of positions 187, 188, 189, 190 or 191; wherein a. when a substitution occurs at position 187, the substituting amino acid is Asn, Asp, Gln, Glu, Gly, His, Pro, Ser and Thr;

b. when a substitution occurs at position 188, the substituting amino acid is Asp or Glu;

c. when a substitution occurs at position 189, the substituting amino acid is Ala, Asn, Asp, Cys, Gln, Glu, Gly, His, Ile, Leu, Met, Pro, Ser, Thr, Tyr or Val;

d. when a substitution occurs at position 190, the substituting amino acid is Asp or Glu; and e. when a substitution occurs at position 191, the substituting amino acid is Asp or Glu;

whereby the BPN' variant has decreased adsorption to, and increased hydrolysis of, an insoluble substrate as compared to wild-type subtilisin BPN' and wherein aspartate and glutamate substitutions at both subtilisin BPN' positions 62 and 129 are combined with at least one further substitution at a corresponding position selected from BPN' positions 60, 61, 65, 66, 105, 106, 130, 132, 133, 188, 190, 200, 201, 202, 205, 207, 210, 211, 212, 216 and 220; and wherein aspartate and glutamate substitutions at both subtilisin BPN' positions 62 and 166 are combined with at least one further substitution at a corresponding position selected from BPN' positions 60, 61, 65, 66, 105, 106, 130, 132, 133, 188, 190, 200, 201, 202, 205, 207, 210, 211, 212, 216 and 220.

9. The BPN' variant of claim 8, wherein two or more substitutions occur in the first loop region.

10. The BPN' variant of claim 8, wherein two or more substitutions occur in the second loop region.

11. The BPN' variant of claim 8, wherein two or more substitutions occur in the third loop region.

12. The BPN' variant of claim 8, wherein two or more substitutions occur in the fourth loop region.

13. The BPN' variant of claim 8, wherein two or more substitutions occur in the fifth loop region.

14. The BPN' variant of claim 8, wherein the wild-type amino acid sequence further comprises a sixth loop region, wherein the modified amino acid sequence further comprises one or more substitutions in the sixth loop region; wherein the substitution(s) in the sixth loop region occurs at one or more of positions 199, 200, 201, 202, 203, 204, 205, 206, 207, 208, 209, 210, 211, 212, 213, 214, 215, 216, 218, 219 or 220; wherein a. when a substitution occurs at position 199, the substituting amino acid is Cys, Ala, His, Thr, Pro, Gly, Gln, Asn, Ser, Asp or Glu;

b. when a substitution occurs at position 200, the substituting amino acid is His, Thr, Pro, Gly, Gln, Asn, Ser, Asp or Glu;

c. when a substitution occurs at position 201, the substituting amino acid is Gly, Gln, Asn, Ser, Asp or Glu;
d. when a substitution occurs at position 202, the substituting amino acid is Pro, Gln, Asn, Ser, Asp or Glu;
e. when a substitution occurs at position 203, the substituting amino acid is Met, Cys, His, Pro, Gly, Gln, Asn, Ser, Asp or Glu;
f. when a substitution occurs at position 204, the substituting amino acid is Glu;
g. when a substitution occurs at position 205, the substituting amino acid is Leu, Met, Cys, Ala, His, Thr, Pro, Gly, Gln, Asn, Ser, Asp or Glu;
h. when a substitution occurs at position 206, the substituting amino acid is Pro, Asn or Ser;
i. when a substitution occurs at position 207, the substituting amino acid is Asp or Glu;
j. when a substitution occurs at position 208, the substituting amino acid is Pro, Gly, Gln, Asn or Ser;
k. when a substitution occurs at position 209, the substituting amino acid is Ile, Val, Met, Cys, Ala, His, Thr, Pro, Gly, Gln, Asn, Ser, Asp or Glu;
l. when a substitution occurs at position 210, the substituting amino acid is Gly, Gln, Asn, Ser, Asp or Glu;
m. when a substitution occurs at position 211, the substituting amino acid is Ala, Pro, Gln, Asn, Ser, Asp or Glu;
n. when a substitution occurs at position 212, the substituting amino acid is Gln, Ser, Asp or Glu;
o. when a substitution occurs at position 213, the substituting amino acid is Trp, Phe, Tyr, Leu, Ile, Val, Met, Cys, Ala, His, Pro, Gly, Gln, Asn, Ser or Glu; but when position 213 is substituted the variant is not a double, triple, quadruple, quintuple, or sextuple mutation variant having substitutions at positions selected from the group consisting of 104, 155, 156, 166, and 189;
p. when a substitution occurs at position 214, the substituting amino acid is Phe, Leu, Ile, Val, Met, Cys, Ala, His, Pro, Gly, Gln or Asn; but when position 214 is substituted the variant is not a double, triple, quadruple, quintuple, or sextuple mutation variant having substitutions at positions selected from the group consisting of 104, 155, 156, 166, and 189;
q. when a substitution occurs at position 215, the substituting amino acid is Thr, Pro, Gln, Asn, Ser, Asp or Glu; but when position 215 is substituted the variant is not a double, triple, quadruple, quintuple, or sextuple mutation variant having substitutions at positions selected from the group consisting of 104, 155, 156, 166, and 189;
r. when a substitution occurs at position 216, the substituting amino acid is His, Thr, Pro, Gly, Gln, Asn, Ser, Asp or Glu;
s. when a substitution occurs at position 218, the substituting amino acid is Glu;
t. when a substitution occurs at position 219, the substituting amino acid is Pro, Gln, Asn, Ser, Asp or Glu; and
u. when a substitution occurs at position 220, the substituting amino acid is Pro, Gly, Gln, Asn, Asp or Glu;

whereby the BPN' variant has decreased adsorption to, and increased hydrolysis of, an insoluble substrate as compared to wild-type subtilisin BPN'.

15. An isolated BPN' variant having a modified amino acid sequence of the Subtilisin BPN' wild-type amino acid sequence set forth in SEQ ID NO:1, the wild-type amino acid sequence comprising a first loop region, a second loop region, a third loop region, a fourth loop region and a fifth loop region; wherein the modified amino acid sequence comprises a substitution at two or more positions in one or more of the loop regions; wherein A. when a substitution occurs in the first loop region, the substitution occurs at one or more of positions 59, 61, 62, 63, 65 or 66; wherein
  a. when a substitution occurs at position 59, the substituting amino acid is Asn or Asp;
  b. when a substitution occurs at position 61, the substituting amino acid is Gln;
  c. when a substitution occurs at position 62, the substituting amino acid is Gln;
  d. when a substitution occurs at position 63, the substituting amino acid is Glu;
  e. when a substitution occurs at position 65, the substituting amino acid is Asn, Asp, Gln, Glu, Pro or Ser; and
  f. when a substitution occurs at position 66, the substituting amino acid is Asn, Asp, Gln, Glu, Pro or Ser;

B. when a substitution occurs in the second loop region, the substitution occurs at one or more of positions 95, 96, 97, 98, 99, 100, 101, 102, 103, 104, 105, 106 or 107; wherein
  a. when a substitution occurs at position 95, the substituting amino acid is Ala, Asn, Asp, Cys, Gln, Glu, Gly, His, Met, Pro, Ser or Thr;
  b. when a substitution occurs at position 96, the substituting amino acid is Ala, Asn, Asp, Cys, Gln, Glu, Gly, His, Ile, Met, Pro, Ser, Thr or Val;
  c. when a substitution occurs at position 97, the substituting amino acid is Asn, Asp, Gln, Glu, Pro or Ser; but when position 97 is substituted the variant is not a double, triple, quadruple, or quintuple mutation variant having substitutions at positions selected from the group consisting of 104, 156, 166, and 189;
  d. when a substitution occurs at position 98, the substituting amino acid is Asn, Asp, Gln, Glu, Gly, His, Pro, Ser or Thr; but when position 97 is substituted with Asp and the variant is a double mutation variant, position 98 is not substituted with Asp; and when position 98 is substituted the variant is not a double, triple, quadruple, or quintuple mutation variant having substitutions at positions selected from the group consisting of 104, 156, 166, and 189;
  e. when a substitution occurs at position 99, the substituting amino acid is Glu; but when position 99 is substituted the variant is not a double, triple, quadruple, or quintuple mutation variant having substitutions at positions selected from the group consisting of 104, 156, 166, and 189;
  f. when a substitution occurs at position 100, the substituting amino acid is Asn, Asp, Gln, Glu, Pro or Ser; but when position 100 is substituted the variant is not a double, triple, quadruple, or quintuple mutation variant having substitutions at positions selected from the group consisting of 104, 156, 166, and 189;
  g. when a substitution occurs at position 101, the substituting amino acid is Asp or Glu; but when position 101 is substituted the variant is not a double, triple, quadruple, or quintuple mutation variant having substitutions at positions selected from the group consisting of 104, 156, 166, and 189;
  h. when a substitution occurs at position 102, the substituting amino acid is Asn, Asp, Gln, Glu, Pro or Ser; but when position 102 is substituted the variant is not a double, triple, quadruple, or quintuple mutation variant having substitutions at positions selected from the group consisting of 104, 156, 166, and 189;
  i. when a substitution occurs at position 103, the substituting amino acid is Asn, Asp, Glu or Ser; but when position 103 is substituted the variant is not a double, triple, quadruple, or quintuple mutation variant having substitutions at positions selected from the group consisting of 104, 156, 166, and 189;
  when a substitution occurs at position 104, the substituting amino acid is Ala, Asn, Asp, Cys, Gln, Glu, Gly, His, Ile, Leu, Met, Pro, Ser, Thr or Val;
  k. when a substitution occurs at position 105, the substituting amino acid is Asp or Glu;
  l. when a substitution occurs at position 106, the substituting amino acid is Ala, Asn, Asp, Cys, Gln, Glu, Gly, His, Ile, Leu, Met, Phe, Pro, Ser, Thr, Tyr or Val; and
  m. when a substitution occurs at position 107, the substituting amino acid is Ala, Asn, Asp, Cys, Gln, Glu, Gly, His, Leu, Met, Pro, Ser, Thr or Val; but when position 107 is substituted the variant is not a double, triple, quadruple, quintuple, or sextuple mutation variant having substitutions at positions selected from the group consisting of 104, 155, 156, 166, and 189;
C. when a substitution occurs in the third loop region, the substitution occurs at one or more of positions 126, 127, 128, 129, 130, 131, 132 or 133; wherein
  a. when a substitution occurs at position 126, the substituting amino acid is Ala, Asn, Asp, Cys, Gln, Glu, Gly, His, Ile, Met, Pro, Ser, Thr or Val; but when position 126 is substituted the variant is not a double, triple, quadruple, quintuple, or sextuple mutation variant having substitutions at positions selected from the group consisting of 104, 155, 156, 166, and 189;
  b. when a substitution occurs at position 127, the substituting amino acid is Asn, Asp, Gln, Glu, Pro or Ser; but when position 127 is substituted the variant is not a double, triple, quadruple, quintuple, or sextuple mutation variant having substitutions at positions selected from the group consisting of 104, 155, 156, 166, and 189;
  c. when a substitution occurs at position 128, the substituting amino acid is Asn, Asp, Gln, Glu, Gly or Ser; but when position 128 is substituted the variant is not a double, triple, quadruple, quintuple, or sextuple mutation variant having substitutions at positions selected from the group consisting of 104, 155, 156, 166, and 189,
  d. when a substitution occurs at position 129, the substituting amino acid is Asn, Asp, Gln, Glu, Gly or Ser; but when position 129 is substituted the variant is not a double, triple, quadruple, quintuple, or sextuple mutation variant having substitutions at positions selected from the group consisting of 104, 155, 156, 166, and 189;
  e. when a substitution occurs at position 130, the substituting amino acid is Asp or Glu;
  f. when a substitution occurs at position 131, the substituting amino acid is Asn, Asp, Gln, Glu, Gly or Ser;
  g. when a substitution occurs at position 132, the substituting amino acid is Asp or Glu; and
  h. when a substitution occurs at position 133, the substituting amino acid is Asn, Asp, Gln, Glu, Gly, His, Pro, Ser or Thr;
D. when a substitution occurs in the fourth loop region, the substitution occurs at one or more of positions 154, 155, 156, 157, 158, 159, 160, 161, 162, 163, 164, 165, 166 or 167; wherein
  a. when a substitution occurs at position 154, the substituting amino acid is Asn, Asp, Gln, Glu, Pro or Ser; but when position 154 is substituted the variant is not a double, triple, quadruple, or quintuple mutation variant having substitutions at positions selected from the group consisting of 104, 156, 166, and 189;
  b. when a substitution occurs at position 155, the substituting amino acid is Asp, Gln, Glu or Ser;
  c. when a substitution occurs at position 156, the substituting amino acid is Asp;
  d. when a substitution occurs at position 157, the substituting amino acid is Asn, Asp, Gln, Glu, Pro or Ser; but when position 157 is substituted the variant is not a double, triple, quadruple, or quintuple mutation variant having substitutions at positions selected from the group consisting of 104, 156, 166, and 189;
  e. when a substitution occurs at position 158, the substituting amino acid is Asn, Asp, Gln, Glu, Gly, Pro or Ser; but when position 158 is substituted the variant is not a double, triple, quadruple, or quintuple mutation variant having substitutions at positions selected from the group consisting of 104, 156, 166, and 189;
  f. when a substitution occurs at position 159, the substituting amino acid is Asp or Glu; but when position 159 is substituted the variant is not a double, triple, quadruple, or quintuple mutation variant having substitutions at positions selected from the group consisting of 104, 156, 166, and 189;
  g. when a substitution occurs at position 160, the substituting amino acid is Asn, Asp, Gln, Glu, Pro or Ser; but when position 160 is substituted the variant is not a double, triple, quadruple, or quintuple mutation variant having substitutions at positions selected from the group consisting of 104, 156, 166, and 189;
  h. when a substitution occurs at position 161, the substituting amino acid is Asp or Glu; but when position 161 is substituted the variant is not a double, triple, quadruple, or quintuple mutation variant having substitutions at positions selected from the group consisting of 104, 156, 166, and 189;
  i. when a substitution occurs at position 162, the substituting amino acid is Asp or Glu; but when position 162 is substituted the variant is not a double, triple, quadruple, or quintuple mutation variant having substitutions at positions selected from the group consisting of 104, 156, 166, and 189;
  j. when a substitution occurs at position 163, the substituting amino acid is Asp or Glu; but when position 163 is substituted the variant is not a double, triple, quadruple, or quintuple mutation variant having substitutions at positions selected from the group consisting of 104, 156, 166, and 189;
  k. when a substitution occurs at position 164, the substituting amino acid is Asn, Asp, Gln, Glu, Gly, Pro or Ser; but when position 164 is substituted the variant is not a double, triple, quadruple, or quintuple mutation variant having substitutions at positions selected from the group consisting of 104, 156, 166, and 189;
  l. when a substitution occurs at position 165, the substituting amino acid is Ala, Asn, Asp, Cys, Gln, Glu, Gly, His, Met, Pro, Ser or Thr; but when position 165 is substituted the variant is not a double, triple, quadruple, or quintuple mutation variant having substitutions at positions selected from the group consisting of 104, 156, 166, and 189;

m. when a substitution occurs at position 166, the substituting amino acid is Asn, Asp, Gln, Glu, Pro or Ser; and n. when a substitution occurs at position 167, the substituting amino acid is Ala, Asn, Asp, Cys, Gln, Glu, Gly, His, Ile, Leu, Met, Pro, Ser, Thr or Val; but when position 167 is substituted the variant is not a double, triple, quadruple, or quintuple mutation variant having substitutions at positions selected from the group consisting of 104, 156, 166, and 189; and E. when a substitution occurs in the fifth loop region, the substitution occurs at one or more of positions 187, 188, 189, 190 or 191; wherein a. when a substitution occurs at position 187, the substituting amino acid is Asn, Asp, Gln, Glu, Gly, His, Pro, Ser and Thr;

b. when a substitution occurs at position 188, the substituting amino acid is Asp or Glu;

c. when a substitution occurs at position 189, the substituting amino acid is Ala, Asn, Asp, Cys, Gln, Glu, Gly, His, Ile, Leu, Met, Pro, Ser, Thr, Tyr or Val;

d. when a substitution occurs at position 190, the substituting amino acid is Asp or Glu; and e. when a substitution occurs at position 191, the substituting amino acid is Asp or Glu;

whereby the BPN' variant has decreased adsorption to, and increased hydrolysis of, an insoluble substrate as compared to wild-type subtilisin BPN' and wherein aspartate and glutamate substitutions at both subtilisin BPN' positions 62 and 166 are combined with at least one further substitution at a corresponding position selected from BPN' positions 60, 61, 65, 66, 105, 106, 130, 132, 133, 188, 190, 200, 201, 202, 205, 207, 210, 211, 212, 216 and 220.

16. The BPN' variant of claim 15, wherein two or more substitutions occur in the first loop region.

17. The BPN' variant of claim 15, wherein two or more substitutions occur in the second loop region.

18. The BPN' variant of claim 15, wherein two or more substitutions occur in the third loop region.

19. The BPN' variant of claim 15, wherein two or more substitutions occur in the fourth loop region.

20. The BPN' variant of claim 15, wherein two or more substitutions occur in the fifth loop region.

21. The BPN' variant of claim 15, wherein the wild-type amino acid sequence further comprises a sixth loop region, wherein the modified amino acid sequence further comprises one or more substitutions in the sixth loop region; wherein the substitution(s) in the sixth loop region occurs at one or more of positions 199, 200, 201, 202, 203, 204, 205, 206, 207, 208, 209, 210, 211, 212, 213, 214, 215, 216, 218, 219 or 220; wherein a. when a substitution occurs at position 199, the substituting amino acid is Cys, Ala, His, Thr, Pro, Gly, Gln, Asn, Ser, Asp or Glu;

b. when a substitution occurs at position 200, the substituting amino acid is His, Thr, Pro, Gly, Gln, Asn, Ser, Asp or Glu;

c. when a substitution occurs at position 201, the substituting amino acid is Gly, Gln, Asn, Ser, Asp or Glu;

d. when a substitution occurs at position 202, the substituting amino acid is Pro, Gln, Asn, Ser, Asp or Glu;

e. when a substitution occurs at position 203, the substituting amino acid is Met, Cys, His, Pro, Gly, Gln, Asn, Ser, Asp or Glu;

f. when a substitution occurs at position 204, the substituting amino acid is Glu;

g. when a substitution occurs at position 205, the substituting amino acid is Leu, Met, Cys, Ala, His, Thr, Pro, Gly, Gln, Asn, Ser, Asp or Glu;

h. when a substitution occurs at position 206, the substituting amino acid is Pro, Asn or Ser;

i. when a substitution occurs at position 207, the substituting amino acid is Asp or Glu;

j. when a substitution occurs at position 208, the substituting amino acid is Pro, Gly, Gln, Asn or Ser;

k. when a substitution occurs at position 209, the substituting amino acid is Ile, Val, Met, Cys, Ala, His, Thr, Pro, Gly, Gln, Asn, Ser, Asp or Glu;

l. when a substitution occurs at position 210, the substituting amino acid is Gly, Gln, Asn, Ser, Asp or Glu;

m. when a substitution occurs at position 211, the substituting amino acid is Ala, Pro, Gln, Asn, Ser, Asp or Glu;

n. when a substitution occurs at position 212, the substituting amino acid is Gln, Ser, Asp or Glu;

o. when a substitution occurs at position 213, the substituting amino acid is Trp, Phe, Tyr, Leu, Ile, Val, Met, Cys, Ala, His, Pro, Gly, Gln, Asn, Ser or Glu; but when position 213 is substituted the variant is not a double, triple, quadruple, quintuple, or sextuple mutation variant having substitutions at positions selected from the group consisting of 104, 155, 156, 166, and 189;

p. when a substitution occurs at position 214, the substituting amino acid is Phe, Leu, Ile, Val, Met, Cys, Ala, His, Pro, Gly, Gln or Asn; but when position 214 is substituted the variant is not a double, triple, quadruple, quintuple, or sextuple mutation variant having substitutions at positions selected from the group consisting of 104, 155, 156, 166, and 189;

q. when a substitution occurs at position 215, the substituting amino acid is Thr, Pro, Gln, Asn, Ser, Asp or Glu; but when position 215 is substituted the variant is not a double, triple, quadruple, quintuple, or sextuple mutation variant having substitutions at positions selected from the group consisting of 104, 155, 156, 166, and 189;

r. when a substitution occurs at position 216, the substituting amino acid is His, Thr, Pro, Gly, Gln, Asn, Ser, Asp or Glu;

s. when a substitution occurs at position 218, the substituting amino acid is Glu;

t. when a substitution occurs at position 219, the substituting amino acid is Pro, Gln, Asn, Ser, Asp or Glu; and u. when a substitution occurs at position 220, the substituting amino acid is Pro, Gly, Gln, Asn, Asp or Glu;

whereby the BPN' variant has decreased adsorption to, and increased hydrolysis of, an insoluble substrate as compared to wild-type subtilisin BPN'.

22. A BPN' variant having a modified amino acid sequence of the Subtilisin BPN' wild-type amino acid sequence set forth in SEQ ID NO:1, the wild-type amino acid sequence comprising a first loop region, a second loop region, a third loop region, a fourth loop region and a fifth loop region; wherein the modified amino acid sequence comprises a substitution at two or more positions in one or more of the loop regions; wherein A. when a substitution occurs in the first loop region, the substitution occurs at one or more of positions 59, 60, 61, 62, 63, 65 or 66; wherein a. when a substitution occurs at position 59, the substituting amino acid is Asn, Asp, Glu or Ser;
b. when a substitution occurs at position 60, the substituting amino acid is Glu;
c. when a substitution occurs at position 61, the substituting amino acid is Asp, Gln, Glu or Ser;
d. when a substitution occurs at position 62, the substituting amino acid is Asp, Gln, Glu or Ser;
e. when a substitution occurs at position 63, the substituting amino acid is Asp or Glu;
f. when a substitution occurs at position 65, the substituting amino acid is Asn, Asp, Gln, Glu, Pro or Ser; and
g. when a substitution occurs at position 66, the substituting amino acid is Asn, Asp, Gln, Glu, Gly, Pro or Ser;

B. when a substitution occurs in the second loop region, the substitution occurs at one or more of positions 95, 96, 97, 98, 100, 102, 103, 106 or 107; wherein
a. when a substitution occurs at position 95, the substituting amino acid is Ala, Asn, Asp, Gln, Glu, Gly, His, Pro, Ser or Thr;
b. when a substitution occurs at position 96, the substituting amino acid is Ala, Asn, Gln, Glu, Gly, His, Ile, Pro, Ser, Thr or Val;
c. when a substitution occurs at position 97, the substituting amino acid is Gln, Pro or Ser; but when position 97 is substituted the variant is not a double, triple, or quadruple mutation variant having substitutions at positions selected from the group consisting of 156, 166, and 189;
d. when a substitution occurs at position 98, the substituting amino acid is Asn, Gln, Gly, His, Ser or Thr; but when position 98 is substituted the variant is not a double, triple, or quadruple mutation variant having substitutions at positions selected from the group consisting of 156, 166, and 189;
e. when a substitution occurs at position 100, the substituting amino acid is Asn, Gln, Pro or Ser; but when position 100 is substituted the variant is not a double, triple, or quadruple mutation variant having substitutions at positions selected from the group consisting of 156, 166, and 189;
f. when a substitution occurs at position 102, the substituting amino acid is Asn, Asp, Gln, Glu, Pro or Ser; but when position 102 is substituted the variant is not a double, triple, or quadruple mutation variant having substitutions at positions selected from the group consisting of 156, 166, and 189;
g. when a substitution occurs at position 103, the substituting amino acid is Asn; but when position 103 is substituted the variant is not a double, triple, or quadruple mutation variant having substitutions at positions selected from the group consisting of 156, 166, and 189;
h. when a substitution occurs at position 106, the substituting amino acid is Cys or Met; and
i. when a substitution occurs at position 107, the substituting amino acid is Gln, His, or Thr; but when position 107 is substituted the variant is not a double, triple, quadruple, or quintuple mutation variant having substitutions at positions selected from the group consisting of 155, 156, 166, and 189;

C. when a substitution occurs in the third loop region, the substitution occurs at one or more of positions 126, 127, 128, 129, 130, 131, 132 or 133; wherein
a. when a substitution occurs at position 126, the substituting amino acid is Ala, Asn, Asp, Cys, Gln, Glu, Gly, His, Ile, Met, Pro, Ser, Thr or Val; but when position 126 is substituted the variant is not a double, triple, quadruple, or quintuple mutation variant having substitutions at positions selected from the group consisting of 155, 156, 166, and 189;
b. when a substitution occurs at position 127, the substituting amino acid is Asn, Asp, Gln, Glu, Pro or Ser; but when position 127 is substituted the variant is not a double, triple, quadruple, or quintuple mutation variant having substitutions at positions selected from the group consisting of 155, 156, 166, and 189;
c. when a substitution occurs at position 128, the substituting amino acid is Asn, Asp, Gln, Glu, Gly or Ser; but when position 128 is substituted the variant is not a double, triple, quadruple, or quintuple mutation variant having substitutions at positions selected from the group consisting of 155, 156, 166, and 189;
d. when a substitution occurs at position 129, the substituting amino acid is Asn, Asp, Gln, Glu, Gly or Ser; but when position 129 is substituted the variant is not a double, triple, quadruple, or quintuple mutation variant having substitutions at positions selected from the group consisting of 155, 156, 166, and 189;
e. when a substitution occurs at position 130, the substituting amino acid is Asp or Glu;
f. when a substitution occurs at position 131, the substituting amino acid is Asn, Asp, Gln, Glu, Gly or Ser;
g. when a substitution occurs at position 132, the substituting amino acid is Asp or Glu; and
h. when a substitution occurs at position 133, the substituting amino acid is Asn, Asp, Gln, Glu, Gly, His, Pro, Ser or Thr;

D. when a substitution occurs in the fourth loop region, the substitution occurs at one or more of positions 154, 155, 156, 157, 158, 159, 160, 161, 162, 163, 164, 165, 166 or 167; wherein
a. when a substitution occurs at position 154, the substituting amino acid is Asn, Asp, Gln, Glu, Pro or Ser; but when position 154 is substituted the variant is not a double, triple, or quadruple mutation variant having substitutions at positions selected from the group consisting of 156, 166, and 189;
b. when a substitution occurs at position 155, the substituting amino acid is Asp, Gln, Glu or Ser;
c. when a substitution occurs at position 156, the substituting amino acid is Asp;
d. when a substitution occurs at position 157, the substituting amino acid is Asn, Asp, Gln, Glu, Pro or Ser; but when position 157 is substituted the variant is not a double, triple, or quadruple mutation variant having substitutions at positions selected from the group consisting of 156, 166, and 189;
e. when a substitution occurs at position 158, the substituting amino acid is Asn, Asp, Gln, Glu, Gly, Pro or Ser; but when position 158 is substituted the variant is not a double, triple, or quadruple mutation variant having substitutions at positions selected from the group consisting of 156, 166, and 189;
f. when a substitution occurs at position 159, the substituting amino acid is Asp or Glu; but when position 159 is substituted the variant is not a double, triple, or quadruple mutation variant having substitutions at positions selected from the group consisting of 156, 166, and 189;
g. when a substitution occurs at position 160, the substituting amino acid is Asn, Asp, Gln, Glu, Pro or Ser; but when position 160 is substituted the variant is not a double, triple, or quadruple mutation variant having substitutions at positions selected from the group consisting of 156, 166, and 189;

h. when a substitution occurs at position 161, the substituting amino acid is Asp or Glu; but when position 161 is substituted the variant is not a double, triple, or quadruple mutation variant having substitutions at positions selected from the group consisting of 156, 166, and 189;

i. when a substitution occurs at position 162, the substituting amino acid is Asp or Glu; but when position 162 is substituted the variant is not a double, triple, or quadruple mutation variant having substitutions at positions selected from the group consisting of 156, 166, and 189;

j. when a substitution occurs at position 163, the substituting amino acid is Asp or Glu; but when position 163 is substituted the variant is not a double, triple, or quadruple mutation variant having substitutions at positions selected from the group consisting of 156, 166, and 189;

k. when a substitution occurs at position 164, the substituting amino acid is Asn, Asp, Gln, Glu, Gly, Pro or Ser; but when position 164 is substituted the variant is not a double, triple, or quadruple mutation variant having substitutions at positions selected from the group consisting of 156, 166, and 189;

l. when a substitution occurs at position 165, the substituting amino acid is Ala, Asn, Asp, Cys, Gln, Glu, Gly, His, Met, Pro, Ser or Thr; but when position 165 is substituted the variant is not a double, triple, or quadruple mutation variant having substitutions at positions selected from the group consisting of 156, 166, and 189;

m. when a substitution occurs at position 166, the substituting amino acid is Asn, Asp, Gln, Glu, Pro or Ser; and n. when a substitution occurs at position 167, the substituting amino acid is Ala, Asn, Asp, Cys, Gln, Glu, Gly, His, Ile, Leu, Met, Pro, Ser, Thr or Val; but when position 167 is substituted the variant is not a double, triple, or quadruple mutation variant having substitutions at positions selected from the group consisting of 156, 166, and 189; and E. when a substitution occurs in the fifth loop region, the substitution occurs at one or more of positions 187, 188, 189, 190 or 191; wherein a. when a substitution occurs at position 187, the substituting amino acid is Asn, Asp, Gln, Glu, Gly, His, Pro, Ser and Thr;

b. when a substitution occurs at position 188, the substituting amino acid is Asp or Glu;

c. when a substitution occurs at position 189, the substituting amino acid is Ala, Asn, Asp, Cys, Gln, Glu, Gly, His, Ile, Leu, Met, Pro, Ser, Thr, Tyr or Val;

d. when a substitution occurs at position 190, the substituting amino acid is Asp or Glu; and e. when a substitution occurs at position 191, the substituting amino acid is Asp or Glu;

whereby the BPN' variant has decreased adsorption to, and increased hydrolysis of, an insoluble substrate as compared to wild-type subtilisin BPN' and wherein aspartate and glutamate substitutions at both subtilisin BPN' positions 62 and 166 are combined with at least one further substitution at a corresponding position selected from BPN' positions 60, 61, 65, 66, 105, 106, 130, 132, 133, 188, 190, 200, 201, 202, 205, 207, 210, 211, 212, 216 and 220.

23. The BPN' variant of claim 22, wherein two or more substitutions occur in the first loop region.

24. The BPN' variant of claim 22, wherein two or more substitutions occur in the second loop region.

25. The BPN' variant of claim 22, wherein two or more substitutions occur in the third loop region.

26. The BPN' variant of claim 22, wherein two or more substitutions occur in the fourth loop region.

27. The BPN' variant of claim 22, wherein two or more substitutions occur in the fifth loop region.

28. The BPN' variant of claim 22, wherein the wild-type amino acid sequence further comprises a sixth loop region, wherein the modified amino acid sequence further comprises one or more substitutions in the sixth loop region; wherein the substitution(s) in the sixth loop region occurs at one or more of positions 199, 200, 201, 202, 203, 204, 205, 206, 207, 208, 209, 210, 211, 212, 213, 214, 215, 216, 218, 219 or 220; wherein a. when a substitution occurs at position 199, the substituting amino acid is Cys, Ala, His, Thr, Pro, Gly, Gln, Asn, Ser, Asp or Glu;

b. when a substitution occurs at position 200, the substituting amino acid is His, Thr, Pro, Gly, Gln, Asn, Ser, Asp or Glu;

c. when a substitution occurs at position 201, the substituting amino acid is Gly, Gln, Asn, Ser, Asp or Glu;

d. when a substitution occurs at position 202, the substituting amino acid is Pro, Gln, Asn, Ser, Asp or Glu;

e. when a substitution occurs at position 203, the substituting amino acid is Met, Cys, His, Pro, Gly, Gln, Asn, Ser, Asp or Glu;

f. when a substitution occurs at position 204, the substituting amino acid is Glu;

g. when a substitution occurs at position 205, the substituting amino acid is Leu, Met, Cys, Ala, His, Thr, Pro, Gly, Gln, Asn, Ser, Asp or Glu;

h. when a substitution occurs at position 206, the substituting amino acid is Pro, Asn or Ser;

i. when a substitution occurs at position 207, the substituting amino acid is Asp or Glu;

j. when a substitution occurs at position 208, the substituting amino acid is Pro, Gly, Gln, Asn or Ser;

k. when a substitution occurs at position 209, the substituting amino acid is Ile, Val, Met, Cys, Ala, His, Thr, Pro, Gly, Gln, Asn, Ser, Asp or Glu;

l. when a substitution occurs at position 210, the substituting amino acid is Gly, Gln, Asn, Ser, Asp or Glu;

m. when a substitution occurs at position 211, the substituting amino acid is Ala, Pro, Gln, Asn, Ser, Asp or Glu;

n. when a substitution occurs at position 212, the substituting amino acid is Gln, Ser, Asp or Glu;

o. when a substitution occurs at position 213, the substituting amino acid is Trp, Phe, Tyr, Leu, Ile, Val, Met, Cys, Ala, His, Pro, Gly, Gln, Asn, Ser or Glu; but when position 213 is substituted the variant is not a double, triple, quadruple, or quintuple mutation variant having substitutions at positions selected from the group consisting of 155, 156, 166, and 189;

p. when a substitution occurs at position 214, the substituting amino acid is Phe, Leu, Ile, Val, Met, Cys, Ala, His, Pro, Gly, Gln or Asn; but when position 214 is substituted the variant is not a double, triple, quadruple, or quintuple mutation variant having substitutions at positions selected from the group consisting of 155, 156, 166, and 189;

q. when a substitution occurs at position 215, the substituting amino acid is Thr, Pro, Gln, Asn, Ser, Asp or Glu; but when position 215 is substituted the variant is not a double, triple, quadruple, or quintuple mutation variant having substitutions at positions selected from the group consisting of 155, 156, 166, and 189;

r. when a substitution occurs at position 216, the substituting amino acid is His, Thr, Pro, Gly, Gln, Asn, Ser, Asp or Glu;

s. when a substitution occurs at position 218, the substituting amino acid is Glu;

t. when a substitution occurs at position 219, the substituting amino acid is Pro, Gln, Asn, Ser, Asp or Glu; and u. when a substitution occurs at position 220, the substituting amino acid is Pro, Gly, Gln, Asn, Asp or Glu;

whereby the BPN' variant has decreased adsorption to, and increased hydrolysis of, an insoluble substrate as compared to wild-type subtilisin BPN'.

29. A BPN' variant having a modified amino acid sequence of the Subtilisin BPN' wild-type amino acid sequence as set forth in SEQ ID NO:1, the wild-type amino acid sequence comprising a first loop region, a second loop region, a third loop region, a fourth loop region and a fifth loop region; wherein the modified amino acid sequence comprises a substitution at two or more positions in one or more of the loop regions; wherein A. when a substitution occurs in the first loop region, the substitution occurs at one or more of positions 59, 60, 61, 62, 63, 65 or 66; wherein a. when a substitution occurs at position 59, the substituting amino acid is Asn, Asp, Glu or Ser;

b. when a substitution occurs at position 60, the substituting amino acid is Glu;

c. when a substitution occurs at position 61, the substituting amino acid is Asp, Gln, Glu or Ser;

d. when a substitution occurs at position 62, the substituting amino acid is Asp, Gln, Glu or Ser;

e. when a substitution occurs at position 63, the substituting amino acid is Asp or Glu;

f. when a substitution occurs at position 65, the substituting amino acid is Asn, Asp, Gln, Glu, Pro or Ser; and g. when a substitution occurs at position 66, the substituting amino acid is Asn, Asp, Gln, Glu, Gly, Pro or Ser;

B. when a substitution occurs in the second loop region, the substitution occurs at one or more of positions 95, 96, 97, 98, 99, 100, 101, 102, 103, 104, 105, 106 or 107; wherein a. when a substitution occurs at position 95, the substituting amino acid is Ala, Asn, Asp, Cys, Gln, Glu, Gly, His, Met, Pro, Ser or Thr;

b. when a substitution occurs at position 96, the substituting amino acid is Ala, Asn, Asp, Cys, Gln, Glu, Gly, His, Ile, Met, Pro, Ser, Thr or Val;

c. when a substitution occurs at position 97, the substituting amino acid is Asn, Asp, Gln, Glu, Pro or Ser; but when position 97 is substituted the variant is not a double, triple, quadruple, or quintuple mutation variant having substitutions at positions selected from the group consisting of 104, 156, 166, and 189;

d. when a substitution occurs at position 98, the substituting amino acid is Asn, Asp, Gln, Glu, Gly, His, Pro, Ser or Thr; but when position 98 is substituted the variant is not a double, triple, quadruple, or quintuple mutation variant having substitutions at positions selected from the group consisting of 104, 156, 166, and 189;

e. when a substitution occurs at position 99, the substituting amino acid is Glu; but when position 99 is substituted the variant is not a double, triple, quadruple, or quintuple mutation variant having substitutions at positions selected from the group consisting of 104, 156, 166, and 189;

f. when a substitution occurs at position 100, the substituting amino acid is Asn, Asp, Gln, Glu, Pro or Ser; but when position 100 is substituted the variant is not a double, triple, quadruple, or quintuple mutation variant having substitutions at positions selected from the group consisting of 104, 156, 166, and 189;

g. when a substitution occurs at position 101, the substituting amino acid is Asp or Glu; but when position 101 is substituted the variant is not a double, triple, quadruple, or quintuple mutation variant having substitutions at positions selected from the group consisting of 104, 156, 166, and 189;

h. when a substitution occurs at position 102, the substituting amino acid is Asn, Asp, Gln, Glu, Pro or Ser; but when position 102 is substituted the variant is not a double, triple, quadruple, or quintuple mutation variant having substitutions at positions selected from the group consisting of 104, 156, 166, and 189;

i. when a substitution occurs at position 103, the substituting amino acid is Asn, Asp, Glu or Ser; but when position 103 is substituted the variant is not a double, triple, quadruple, or quintuple mutation variant having substitutions at positions selected from the group consisting of 104, 156, 166, and 189;

j. when a substitution occurs at position 104, the substituting amino acid is Ala, Asn, Asp, Cys, Gln, Glu, Gly, His, Ile, Leu, Met, Pro, Ser, Thr or Val;

k. when a substitution occurs at position 105, the substituting amino acid is Asp or Glu;

l. when a substitution occurs at position 106, the substituting amino acid is Ala, Asn, Asp, Cys, Gln, Glu, Gly, His, Ile, Leu, Met, Phe, Pro, Ser, Thr, Tyr or Val; and m. when a substitution occurs at position 107, the substituting amino acid is Ala, Asn, Asp, Cys, Gln, Glu, Gly, His, Leu, Met, Pro, Ser, Thr or Val; but when position 107 is substituted the variant is not a double, triple, quadruple, quintuple, or sextuple mutation variant having substitutions at positions selected from the group consisting of 104, 155, 156, 166, and 189;

C. when a substitution occurs in the third loop region, the substitution occurs at one or more of positions 126, 127, 129, 131, 132 or 133; wherein a. when a substitution occurs at position 126, the substituting amino acid is Asn, Asp, Gln, Glu, His, Pro, Ser, or Thr; but when position 126 is substituted the variant is not a double, triple, quadruple, quintuple, or sextuple mutation variant having substitutions at positions selected from the group consisting of 104, 155, 156, 166, and 189;

b. when a substitution occurs at position 127, the substituting amino acid is Pro; but when position 127 is substituted the variant is not a double, triple, quadruple, quintuple, or sextuple mutation variant having substitutions at positions selected from the group consisting of 104, 155, 156, 166, and 189;

c. when a substitution occurs at position 129, the substituting amino acid is Asn, Gln, or Ser; but when position 129 is substituted the variant is not a double, triple, quadruple, quintuple, or sextuple mutation variant having substitutions at positions selected from the group consisting of 104, 155, 156, 166, and 189;

d. when a substitution occurs at position 131, the substituting amino acid is Asn, Gln, or Ser;

e. when a substitution occurs at position 132, the substituting amino acid is Asp or Glu; and f. when a substitution occurs at position 133, the substituting amino acid is Asn, Asp, Gln, Glu, Gly, His, Pro, Ser or Thr;

D. when a substitution occurs in the fourth loop region, the substitution occurs at one or more of positions 154, 155, 156, 157, 158, 159, 160, 161, 162, 163, 164, 165, 166 or 167; wherein a. when a substitution occurs at position 154, the substituting amino acid is Asn, Asp, Gln, Glu, Pro or Ser; but when position 154 is substituted the variant is not a double, triple, quadruple, or quintuple mutation variant having substitutions at positions selected from the group consisting of 104, 156, 166, and 189;

b. when a substitution occurs at position 155, the substituting amino acid is Asp, Gln, Glu or Ser;

c. when a substitution occurs at position 156, the substituting amino acid is Asp;

d. when a substitution occurs at position 157, the substituting amino acid is Asn, Asp, Gln, Glu, Pro or Ser; but when position 157 is substituted the variant is not a double, triple, quadruple, or quintuple mutation variant having substitutions at positions selected from the group consisting of 104, 156, 166, and 189;

e. when a substitution occurs at position 158, the substituting amino acid is Asn, Asp, Gln, Glu, Gly, Pro or Ser; but when position 158 is substituted the variant is not a double, triple, quadruple, or quintuple mutation variant having substitutions at positions selected from the group consisting of 104, 156, 166, and 189;

f. when a substitution occurs at position 159, the substituting amino acid is Asp or Glu; but when position 159 is substituted the variant is not a double, triple, quadruple, or quintuple mutation variant having substitutions at positions selected from the group consisting of 104, 156, 166, and 189;

g. when a substitution occurs at position 160, the substituting amino acid is Asn, Asp, Gln, Glu, Pro or Ser; but when position 160 is substituted the variant is not a double, triple, quadruple, or quintuple mutation variant having substitutions at positions selected from the group consisting of 104, 156, 166, and 189;

h. when a substitution occurs at position 161, the substituting amino acid is Asp or Glu; but when position 161 is substituted the variant is not a double, triple, quadruple, or quintuple mutation variant having substitutions at positions selected from the group consisting of 104, 156, 166, and 189;

i. when a substitution occurs at position 162, the substituting amino acid is Asp or Glu; but when position 162 is substituted the variant is not a double, triple, quadruple, or quintuple mutation variant having substitutions at positions selected from the group consisting of 104, 156, 166, and 189;

j. when a substitution occurs at position 163, the substituting amino acid is Asp or Glu; but when position 163 is substituted the variant is not a double, triple, quadruple, or quintuple mutation variant having substitutions at positions selected from the group consisting of 104, 156, 166, and 189;

k. when a substitution occurs at position 164, the substituting amino acid is Asn, Asp, Gln, Glu, Gly, Pro or Ser; but when position 164 is substituted the variant is not a double, triple, quadruple, or quintuple mutation variant having substitutions at positions selected from the group consisting of 104, 156, 166, and 189;

l. when a substitution occurs at position 165, the substituting amino acid is Ala, Asn, Asp, Cys, Gln, Glu, Gly, His, Met, Pro, Ser or Thr; but when position 165 is substituted the variant is not a double, triple, quadruple, or quintuple mutation variant having substitutions at positions selected from the group consisting of 104, 156, 166, and 189;

m. when a substitution occurs at position 166, the substituting amino acid is Asn, Asp, Gln, Glu, Pro or Ser; and n. when a substitution occurs at position 167, the substituting amino acid is Ala, Asn, Asp, Cys, Gln, Glu, Gly, His, Ile, Leu, Met, Pro, Ser, Thr or Val; but when position 167 is substituted the variant is not a double, triple, quadruple, or quintuple mutation variant having substitutions at positions selected from the group consisting of 104, 156, 166, and 189; and E. when a substitution occurs in the fifth loop region, the substitution occurs at one or more of positions 187, 188, 189, 190 or 191; wherein a. when a substitution occurs at position 187, the substituting amino acid is Asn, Asp, Gln, Glu, Gly, His, Pro, Ser and Thr;

b. when a substitution occurs at position 188, the substituting amino acid is Asp or Glu;

c. when a substitution occurs at position 189, the substituting amino acid is Ala, Asn, Asp, Cys, Gln, Glu, Gly, His, Ile, Leu, Met, Pro, Ser, Thr, Tyr or Val;

d. when a substitution occurs at position 190, the substituting amino acid is Asp or Glu; and e. when a substitution occurs at position 191, the substituting amino acid is Asp or Glu;

whereby the BPN' variant has decreased adsorption to, and increased hydrolysis of, an insoluble substrate as compared to wild-type subtilisin BPN' and wherein aspartate and glutamate substitutions at both subtilisin BPN' positions 62 and 166 are combined with at least one further substitution at a corresponding position selected from BPN' positions 60, 61, 65, 66, 105, 106, 130, 132, 133, 188, 190, 200, 201, 202, 205, 207, 210, 211, 212, 216 and 220.

30. The BPN' variant of claim 29, wherein two or more substitutions occur in the first loop region.

31. The BPN' variant of claim 29, wherein two or more substitutions occur in the second loop region.

32. The BPN' variant of claim 29, wherein two or more substitutions occur in the third loop region.

33. The BPN' variant of claim 29, wherein two or more substitutions occur in the fourth loop region.

34. The BPN' variant of claim 29, wherein two or more substitutions occur in the fifth loop region.

35. The BPN' variant of claim 29, wherein the wild-type amino acid sequence further comprises a sixth loop region, wherein the modified amino acid sequence further comprises one or more substitutions in the sixth loop region; wherein the substitution(s) in the sixth loop region occurs at one or more of positions 199, 200, 201, 202, 203, 204, 205, 206, 207, 208, 209, 210, 211, 212, 213, 214, 215, 216, 218, 219 or 220; wherein a. when a substitution occurs at position 199, the substituting amino acid is Cys, Ala, His, Thr, Pro, Gly, Gln, Asn, Ser, Asp or Glu;

b. when a substitution occurs at position 200, the substituting amino acid is His, Thr, Pro, Gly, Gln, Asn, Ser, Asp or Glu;

c. when a substitution occurs at position 201, the substituting amino acid is Gly, Gln, Asn, Ser, Asp or Glu;

d. when a substitution occurs at position 202, the substituting amino acid is Pro, Gln, Asn, Ser, Asp or Glu;

e. when a substitution occurs at position 203, the substituting amino acid is Met, Cys, His, Pro, Gly, Gln, Asn, Ser, Asp or Glu;

f. when a substitution occurs at position 204, the substituting amino acid is Glu;

g. when a substitution occurs at position 205, the substituting amino acid is Leu, Met, Cys, Ala, His, Thr, Pro, Gly, Gln, Asn, Ser, Asp or Glu;

h. when a substitution occurs at position 206, the substituting amino acid is Pro, Asn or Ser;

i. when a substitution occurs at position 207, the substituting amino acid is Asp or Glu;

j. when a substitution occurs at position 208, the substituting amino acid is Pro, Gly, Gln, Asn or Ser;

k. when a substitution occurs at position 209, the substituting amino acid is Ile, Val, Met, Cys, Ala, His, Thr, Pro, Gly, Gln, Asn, Ser, Asp or Glu;

l. when a substitution occurs at position 210, the substituting amino acid is Gly, Gln, Asn, Ser, Asp or Glu;

m. when a substitution occurs at position 211, the substituting amino acid is Ala, Pro, Gln, Asn, Ser, Asp or Glu;

n. when a substitution occurs at position 212, the substituting amino acid is Gln, Ser, Asp or Glu;

o. when a substitution occurs at position 213, the substituting amino acid is Trp, Phe, Tyr, Leu, Ile, Val, Met, Cys, Ala, His, Pro, Gly, Gln, Asn, Ser or Glu; but when position 213 is substituted the variant is not a double, triple, quadruple quintuple, or sextuple mutation variant having substitutions at positions selected from the group consisting of 104, 155, 156, 166, and 189;

p. when a substitution occurs at position 214, the substituting amino acid is Phe, Leu, Ile, Val, Met, Cys, Ala, His, Pro, Gly, Gln or Asn; but when position 214 is substituted the variant is not a double, triple, quadruple, quintuple, or sextuple mutation variant having substitutions at positions selected from the group consisting of 104, 155, 156, 166, and 189;

q. when a substitution occurs at position 215, the substituting amino acid is Thr, Pro, Gln, Asn, Ser, Asp or Glu; but when position 215 is substituted the variant is not a double, triple, quadruple, quintuple, or sextuple mutation variant having substitutions at positions selected from the group consisting of 104, 155, 156, 166, and 189;

r. when a substitution occurs at position 216, the substituting amino acid is His, Thr, Pro, Gly, Gln, Asn, Ser, Asp or Glu;

s. when a substitution occurs at position 218, the substituting amino acid is Glu;

t. when a substitution occurs at position 219, the substituting amino acid is Pro, Gln, Asn, Ser, Asp or Glu; and u. when a substitution occurs at position 220, the substituting amino acid is Pro, Gly, Gln, Asn, Asp or Glu;

whereby the BPN' variant has decreased adsorption to, and increased hydrolysis of, an insoluble substrate as compared to wild-type subtilisin BPN'.

36. A BPN' variant having a modified amino acid sequence of the Subtilisin BPN' wild-type amino acid sequence set forth in SEQ ID NO:1, the wild-type amino acid sequence comprising a first loop region, a second loop region, a third loop region, a fourth loop region and a fifth loop region; wherein the modified amino acid sequence comprises a substitution at two or more positions in one or more of the loop regions; wherein A. when a substitution occurs in the first loop region, the substitution occurs at one or more of positions 59, 60, 61, 62, 63, 65 or 66; wherein
  a. when a substitution occurs at position 59, the substituting amino acid is Asn, Asp, Glu or Ser;
  b. when a substitution occurs at position 60, the substituting amino acid is Glu;
  c. when a substitution occurs at position 61, the substituting amino acid is Asp, Gln, Glu or Ser;
  d. when a substitution occurs at position 62, the substituting amino acid is Asp, Gln, Glu or Ser;
  e. when a substitution occurs at position 63, the substituting amino acid is Asp or Glu;
  f. when a substitution occurs at position 65, the substituting amino acid is Asn, Asp, Gln, Glu, Pro or Ser; and
  g. when a substitution occurs at position 66, the substituting amino acid is Asn, Asp, Gln, Glu, Gly, Pro or Ser;

B. when a substitution occurs in the second loop region, the substitution occurs at one or more of positions 95, 96, 97, 98, 99, 100, 101, 102, 103, 104, 105, 106 or 107; wherein
  a. when a substitution occurs at position 95, the substituting amino acid is Ala, Asn, Asp, Cys, Gln, Glu, Gly, His, Met, Pro, Ser or Thr;
  b. when a substitution occurs at position 96, the substituting amino acid is Ala, Asn, Asp, Cys, Gln, Glu, Gly, His, Ile, Met, Pro, Ser, Thr or Val;
  c. when a substitution occurs at position 97, the substituting amino acid is Asn, Asp, Gln, Glu, Pro or Ser; but when position 97 is substituted the variant is not a double or triple mutation variant having substitutions at positions selected from the group consisting of 104 and 189;
  d. when a substitution occurs at position 98, the substituting amino acid is Asn, Asp, Gln, Glu, Gly, His, Pro, Ser or Thr; but when position 98 is substituted the variant is not a double or triple mutation variant having substitutions at positions selected from the group consisting of 104 and 189;
  e. when a substitution occurs at position 99, the substituting amino acid is Glu; but when position 99 is substituted the variant is not a double or triple mutation variant having substitutions at positions selected from the group consisting of 104 and 189;
  f. when a substitution occurs at position 100, the substituting amino acid is Asn, Asp, Gln, Glu, Pro or Ser; but when position 100 is substituted the variant is not a double or triple mutation variant having substitutions at positions selected from the group consisting of 104 and 189;
  g. when a substitution occurs at position 101, the substituting amino acid is Asp or Glu; but when position 101 is substituted the variant is not a double or triple mutation variant having substitutions at positions selected from the group consisting of 104 and 189;

h. when a substitution occurs at position 102, the substituting amino acid is Asn, Asp, Gln, Glu, Pro or Ser; but when position 102 is substituted the variant is not a double or triple mutation variant having substitutions at positions selected from the group consisting of 104 and 189;
i. when a substitution occurs at position 103, the substituting amino acid is Asn, Asp, Glu or Ser; but when position 103 is substituted the variant is not a double or triple mutation variant having substitutions at positions selected from the group consisting of 104 and 189;
j. when a substitution occurs at position 104, the substituting amino acid is Ala, Asn, Asp, Cys, Gln, Glu, Gly, His, Ile, Leu, Met, Pro, Ser, Thr or Val;
k. when a substitution occurs at position 105, the substituting amino acid is Asp or Glu;
l. when a substitution occurs at position 106, the substituting amino acid is Ala, Asn, Asp, Cys, Gln, Glu, Gly, His, Ile, Leu, Met, Phe, Pro, Ser, Thr, Tyr or Val; and
m. when a substitution occurs at position 107, the substituting amino acid is Ala, Asn, Asp, Cys, Gln, Glu, Gly, His, Leu, Met, Pro, Ser, Thr or Val; but when position 107 is substituted the variant is not a double or triple mutation variant having substitutions at positions selected from the group consisting of 104 and 189;

C. when a substitution occurs in the third loop region, the substitution occurs at one or more of positions 126, 127, 128, 129, 130, 131, 132 or 133; wherein
a. when a substitution occurs at position 126, the substituting amino acid is Ala, Asn, Asp, Cys, Gln, Glu, Gly, His, Ile, Met, Pro, Ser, Thr or Val; but when position 126 is substituted the variant is not a double or triple mutation variant having substitutions at positions selected from the group consisting of 104 and 189;
b. when a substitution occurs at position 127, the substituting amino acid is Asn, Asp, Gln, Glu, Pro or Ser; but when position 127 is substituted the variant is not a double or triple mutation variant having substitutions at positions selected from the group consisting of 104 and 189;
c. when a substitution occurs at position 128, the substituting amino acid is Asn, Asp, Gln, Glu, Gly or Ser; but when position 128 is substituted the variant is not a double or triple mutation variant having substitutions at positions selected from the group consisting of 104 and 189;
d. when a substitution occurs at position 129, the substituting amino acid is Asn, Asp, Gln, Glu, Gly or Ser; but when position 129 is substituted the variant is not a double or triple mutation variant having substitutions at positions selected from the group consisting of 104 and 189;
e. when a substitution occurs at position 130, the substituting amino acid is Asp or Glu;
f. when a substitution occurs at position 131, the substituting amino acid is Asn, Asp, Gln, Glu, Gly or Ser;
g. when a substitution occurs at position 132, the substituting amino acid is Asp or Glu; and
h. when a substitution occurs at position 133, the substituting amino acid is Asn, Asp, Gln, Glu, Gly, His, Pro, Ser or Thr;

D. when a substitution occurs in the fourth loop region, the substitution occurs at one or more of positions 154, 157, 158, 160, 164, or 167; wherein a. when a substitution occurs at position 154, the substituting amino acid is Asn, Asp, Gln, Glu, Pro or Ser; but when position 154 is substituted the variant is not a double or triple mutation variant having substitutions at positions selected from the group consisting of 104 and 189;
b. when a substitution occurs at position 157, the substituting amino acid is Asn, Asp, Gln, Glu, Pro or Ser; but when position 157 is substituted the variant is not a double or triple mutation variant having substitutions at positions selected from the group consisting of 104 and 189;
c. when a substitution occurs at position 158, the substituting amino acid is Asn, Gln, Pro or Ser; but when position 158 is substituted the variant is not a double or triple mutation variant having substitutions at positions selected from the group consisting of 104 and 189;
d. when a substitution occurs at position 160, the substituting amino acid is Asn, Gln or Pro; but when position 160 is substituted the variant is not a double or triple mutation variant having substitutions at positions selected from the group consisting of 104 and 189;
e. when a substitution occurs at position 164, the substituting amino acid is Asn, Gln, Pro, or Ser; but when position 164 is substituted the variant is not a double or triple mutation variant having substitutions at positions selected from the group consisting of 104 and 189; and
f. when a substitution occurs at position 167, the substituting amino acid is His, Ile, Leu, or Pro; but when position 167 is substituted the variant is not a double or triple mutation variant having substitutions at positions selected from the group consisting of 104 and 189;

E. when a substitution occurs in the fifth loop region, the substitution occurs at one or more of positions 187, 188, 189, 190 or 191; wherein
a. when a substitution occurs at position 187, the substituting amino acid is Asn, Asp, Gln, Glu, Gly, His, Pro, Ser and Thr;
b. when a substitution occurs at position 188, the substituting amino acid is Asp or Glu;
c. when a substitution occurs at position 189, the substituting amino acid is Ala, Asn, Asp, Cys, Gln, Glu, Gly, His, Ile, Leu, Met, Pro, Ser, Thr, Tyr or Val;
d. when a substitution occurs at position 190, the substituting amino acid is Asp or Glu; and
e. when a substitution occurs at position 191, the substituting amino acid is Asp or Glu;
whereby the BPN' variant has decreased adsorption to, and increased hydrolysis of, an insoluble substrate as compared to wild-type subtilisin BPN'.

37. The BPN' variant of claim 36, wherein two or more substitutions occur in the first loop region.

38. The BPN' variant of claim 36, wherein two or more substitutions occur in the second loop region.

39. The BPN' variant of claim 36, wherein two or more substitutions occur in the third loop region.

40. The BPN' variant of claim 36, wherein two or more substitutions occur in the fourth loop region.

41. The BPN' variant of claim 36, wherein two or more substitutions occur in the fifth loop region.

42. The BPN' variant of claim 36, wherein the wild-type amino acid sequence further comprises a sixth loop region, wherein the modified amino acid sequence further comprises one or more substitutions in the sixth loop region; wherein the substitution(s) in the sixth loop region occurs at one or more of positions 199, 200, 201, 202, 203, 204, 205, 206, 207, 208, 209, 210, 211, 212, 213, 214, 215, 216, 218, 219 or 220; wherein a. when a substitution occurs at position 199, the substituting amino acid is Cys, Ala, His, Thr, Pro, Gly, Gln, Asn, Ser, Asp or Glu;

b. when a substitution occurs at position 200, the substituting amino acid is His, Thr, Pro, Gly, Gln, Asn, Ser, Asp or Glu;

c. when a substitution occurs at position 201, the substituting amino acid is Gly, Gln, Asn, Ser, Asp or Glu;

d. when a substitution occurs at position 202, the substituting amino acid is Pro, Gln, Asn, Ser, Asp or Glu;

e. when a substitution occurs at position 203, the substituting amino acid is Met, Cys, His, Pro, Gly, Gln, Asn, Ser, Asp or Glu;

f. when a substitution occurs at position 204, the substituting amino acid is Glu;

g. when a substitution occurs at position 205, the substituting amino acid is Leu, Met, Cys, Ala, His, Thr, Pro, Gly, Gln, Asn, Ser, Asp or Glu;

h. when a substitution occurs at position 206, the substituting amino acid is Pro, Asn or Ser;

i. when a substitution occurs at position 207, the substituting amino acid is Asp or Glu;

j. when a substitution occurs at position 208, the substituting amino acid is Pro, Gly, Gln, Asn or Ser;

k. when a substitution occurs at position 209, the substituting amino acid is Ile, Val, Met, Cys, Ala, His, Thr, Pro, Gly, Gln, Asn, Ser, Asp or Glu;

l. when a substitution occurs at position 210, the substituting amino acid is Gly, Gln, Asn, Ser, Asp or Glu;

m. when a substitution occurs at position 211, the substituting amino acid is Ala, Pro, Gln, Asn, Ser, Asp or Glu;

n. when a substitution occurs at position 212, the substituting amino acid is Gln, Ser, Asp or Glu;

o. when a substitution occurs at position 213, the substituting amino acid is Trp, Phe, Tyr, Leu, Ile, Val, Met, Cys, Ala, His, Pro, Gly, Gln, Asn, Ser or Glu; but when position 213 is substituted the variant is not a double or triple mutation variant having substitutions at positions selected from the group consisting of 104 and 189;

p. when a substitution occurs at position 214, the substituting amino acid is Phe, Leu, Ile, Val, Met, Cys, Ala, His, Pro, Gly, Gln or Asn; but when position 214 is substituted the variant is not a double or triple mutation variant having substitutions at positions selected from the group consisting of 104 and 189;

q. when a substitution occurs at position 215, the substituting amino acid is Thr, Pro, Gln, Asn, Ser, Asp or Glu; but when position 215 is substituted the variant is not a double or triple mutation variant having substitutions at positions selected from the group consisting of 104 and 189;

r. when a substitution occurs at position 216, the substituting amino acid is His, Thr, Pro, Gly, Gln, Asn, Ser, Asp or Glu;

s. when a substitution occurs at position 218, the substituting amino acid is Glu;

t. when a substitution occurs at position 219, the substituting amino acid is Pro, Gln, Asn, Ser, Asp or Glu; and u. when a substitution occurs at position 220, the substituting amino acid is Pro, Gly, Gln, Asn, Asp or Glu;

whereby the BPN' variant has decreased adsorption to, and increased hydrolysis of, an insoluble substrate as compared to wild-type subtilisin BPN'.

43. A BPN' variant having a modified amino acid sequence of the Subtilisin BPN' wild-type amino acid sequence set forth in SEQ ID NO:1, the wild-type amino acid sequence comprising a first loop region, a second loop region, a third loop region, a fourth loop region and a fifth loop region; wherein the modified amino acid sequence comprises a substitution at two or more positions in one or more of the loop regions; wherein A. when a substitution occurs in the first loop region, the substitution occurs at one or more of positions 59, 60, 61, 62, 63, 65 or 66; wherein a. when a substitution occurs at position 59, the substituting amino acid is Asn, Asp, Glu or Ser;

b. when a substitution occurs at position 60, the substituting amino acid is Glu;

c. when a substitution occurs at position 61, the substituting amino acid is Asp, Gln, Glu or Ser;

d. when a substitution occurs at position 62, the substituting amino acid is Asp, Gln, Glu or Ser;

e. when a substitution occurs at position 63, the substituting amino acid is Asp or Glu;

f. when a substitution occurs at position 65, the substituting amino acid is Asn, Asp, Gln, Glu, Pro or Ser; and g. when a substitution occurs at position 66, the substituting amino acid is Asn, Asp, Gln, Glu, Gly, Pro or Ser;

B. when a substitution occurs in the second loop region, substitution occurs at one or more of positions 95, 96, 97, 98, 99, 100, 101, 102, 103, 104, 105, 106 or 107; wherein a. when a substitution occurs at position 95, the substituting amino acid is Ala, Asn, Asp, Cys, Gln, Glu, Gly, His, Met, Pro, Ser or Thr;

b. when a substitution occurs at position 96, the substituting amino acid is Ala, Asn, Asp, Cys, Gln, Glu, Gly, His, Ile, Met, Pro, Ser, Thr or Val;

c. when a substitution occurs at position 97, the substituting amino acid is Asn, Asp, Gln, Glu, Pro or Ser; but when position 97 is substituted the variant is not a double, triple, or quadruple mutation variant having substitutions at positions selected from the group consisting of 104, 156, and 166;

d. when a substitution occurs at position 98, the substituting amino acid is Asn, Asp, Gln, Glu, Gly, His, Pro, Ser or Thr; but when position 98 is substituted the variant is not a double, triple, or quadruple mutation variant having substitutions at positions selected from the group consisting of 104, 156, and 166;

e. when a substitution occurs at position 99, the substituting amino acid is Glu; but when position 99 is substituted the variant is not a double, triple, or quadruple mutation variant having substitutions at positions selected from the group consisting of 104, 156, and 166;

f. when a substitution occurs at position 100, the substituting amino acid is Asn, Asp, Gln, Glu, Pro or Ser; but when position 100 is substituted the variant is not a double, triple, or quadruple mutation variant having substitutions at positions selected from the group consisting of 104, 156, and 166;

g. when a substitution occurs at position 101, the substituting amino acid is Asp or Glu; but when position 101 is substituted the variant is not a double, triple, or quadruple mutation variant having substitutions at positions selected from the group consisting of 104, 156, and 166;

h. when a substitution occurs at position 102, the substituting amino acid is Asn, Asp, Gln, Glu, Pro or Ser; but when position 102 is substituted the variant is not a double, triple, or quadruple mutation variant having substitutions at positions selected from the group consisting of 104, 156, and 166;

i. when a substitution occurs at position 103, the substituting amino acid is Asn, Asp, Glu or Ser; but when position 103 is substituted the variant is not a double, triple, or quadruple mutation variant having substitutions at positions selected from the group consisting of 104, 156, and 166;

j. when a substitution occurs at position 104, the substituting amino acid is Ala, Asn, Asp, Cys, Gln, Glu, Gly, His, Ile, Leu, Met, Pro, Ser, Thr or Val;

k. when a substitution occurs at position 105, the substituting amino acid is Asp or Glu;

l. when a substitution occurs at position 106, the substituting amino acid is Ala, Asn, Asp, Cys, Gln, Glu, Gly, His, Ile, Leu, Met, Phe, Pro, Ser, Thr, Tyr or Val; and m. when a substitution occurs at position 107, the substituting amino acid is Ala, Asn, Asp, Cys, Gln, Glu, Gly, His, Leu, Met, Pro, Ser, Thr or Val; but when position 107 is substituted the variant is not a double, triple, quadruple, or quintuple mutation variant having substitutions at positions selected from the group consisting of 104, 155, 156, and 166;

C. when a substitution occurs in the third loop region, the substitution occurs at one or more of positions 126, 127, 128, 129, 130, 131, 132 or 133; wherein a. when a substitution occurs at position 126, the substituting amino acid is Ala, Asn, Asp, Cys, Gln, Glu, Gly, His, Ile, Met, Pro, Ser, Thr or Val; but when position 126 is substituted the variant is not a double, triple, quadruple, or quintuple mutation variant having substitutions at positions selected from the group consisting of 104, 155, 156, and 166;

b. when a substitution occurs at position 127, the substituting amino acid is Asn, Asp, Gln, Glu, Pro or Ser; but when position 127 is substituted the variant is not a double, triple, quadruple, and quintuple mutation variant having substitutions at positions selected from the group consisting of 104, 155, 156, and 166;

c. when a substitution occurs at position 128, the substituting amino acid is Asn, Asp, Gln, Glu, Gly or Ser; but when position 128 is substituted the variant is not a double, triple, quadruple, or quintuple mutation variant having substitutions at positions selected from the group consisting of 104, 155, 156, and 166;

d. when a substitution occurs at position 129, the substituting amino acid is Asn, Asp, Gln, Glu, Gly or Ser; but when position 129 is substituted the variant is not a double, triple, quadruple, or quintuple mutation variant having substitutions at positions selected from the group consisting of 104, 155, 156, and 166;

e. when a substitution occurs at position 130, the substituting amino acid is Asp or Glu;

f. when a substitution occurs at position 131, the substituting amino acid is Asn, Asp, Gln, Glu, Gly or Ser;

g. when a substitution occurs at position 132, the substituting amino acid is Asp or Glu; and h. when a substitution occurs at position 133, the substituting amino acid is Asn, Asp, Gln, Glu, Gly, His, Pro, Ser or Thr;

D. when a substitution occurs in the fourth loop region, the substitution occurs at one or more of positions 154, 155, 156, 157, 158, 159, 160, 161, 162, 163, 164, 165, 166 or 167; wherein a. when a substitution occurs at position 154, the substituting amino acid is Asn, Asp, Gln, Glu, Pro or Ser; but when position 154 is substituted the variant is not a double, triple, or quadruple mutation variant having substitutions at positions selected from the group consisting of 104, 156, and 166;

b. when a substitution occurs at position 155, the substituting amino acid is Asp, Gln, Glu or Ser;

c. when a substitution occurs at position 156, the substituting amino acid is Asp;

d. when a substitution occurs at position 157, the substituting amino acid is Asn, Asp, Gln, Glu, Pro or Ser; but when position 157 is substituted the variant is not a double, triple, or quadruple mutation variant having substitutions at positions selected from the group consisting of 104, 156, and 166;

e. when a substitution occurs at position 158, the substituting amino acid is Asn, Asp, Gln, Glu, Gly, Pro or Ser; but when position 158 is substituted the variant is not a double, triple, or quadruple mutation variant having substitutions at positions selected from the group consisting of 104, 156, 166;

f. when a substitution occurs at position 159, the substituting amino acid is Asp or Glu; but when position 159 is substituted the variant is not a double, triple, or quadruple mutation variant having substitutions at positions selected from the group consisting of 104, 156, and 166;

g. when a substitution occurs at position 160, the substituting amino acid is Asn, Asp, Gln, Glu, Pro or Ser; but when position 160 is substituted the variant is not a double, triple, or quadruple mutation variant having substitutions at positions selected from the group consisting of 104, 156, and 166;

h. when a substitution occurs at position 161, the substituting amino acid is Asp or Glu; but when position 161 is substituted the variant is not a double, triple, or quadruple mutation variant having substitutions at positions selected from the group consisting of 104, 156, and 166;

i. when a substitution occurs at position 162, the substituting amino acid is Asp or Glu; but when position 162 is substituted the variant is not a double, triple, or quadruple mutation variant having substitutions at positions selected from the group consisting of 104, 156, and 166;

j. when a substitution occurs at position 163, the substituting amino acid is Asp or Glu; but when position 163 is substituted the variant is not a double, triple, or quadruple mutation variant having substitutions at positions selected from the group consisting of 104, 156, and 166;

k. when a substitution occurs at position 164, the substituting amino acid is Asn, Asp, Gln, Glu, Gly, Pro or Ser; but when position 164 is substituted the variant is not a double, triple, or quadruple mutation variant having substitutions at positions selected from the group consisting of 104, 156, and 166;

l. when a substitution occurs at position 165, the substituting amino acid is Ala, Asn, Asp, Cys, Gln, Glu, Gly, His, Met, Pro, Ser or Thr; but when position 165 is substituted the variant is not a double, triple, or quadruple mutation variant having substitutions at positions selected from the group consisting of 104, 156, and 166;

m. when a substitution occurs at position 166, the substituting amino acid is Asn, Asp, Gln, Glu, Pro or Ser; and n. when a substitution occurs at position 167, the substituting amino acid is Ala, Asn, Asp, Cys, Gln, Glu, Gly, His, Ile, Leu, Met, Pro, Ser, Thr or Val; but when position 167 is substituted the variant is not a double, triple, or quadruple mutation variant having substitutions at positions selected from the group consisting of 104, 156, and 166; and E. when a substitution occurs in the fifth loop region, the substitution occurs at one or more of positions 187 or 190; wherein a. when a substitution occurs at position 187, the substituting amino acid is Asn, Asp, Gln, Glu, Gly, His, Pro, Ser and Thr; and b. when a substitution occurs at position 190, the substituting amino acid is Asp or Glu;

whereby the BPN' variant has decreased adsorption to, and increased hydrolysis of, an insoluble substrate as compared to wild-type subtilisin BPN' and wherein aspartate and glutamate substitutions at both subtilisin BPN' positions 62 and 166 are combined with at least one further substitution at a corresponding position selected from BPN' positions 60, 61, 65, 66, 105, 106, 130, 132, 133, 188, 190, 200, 201, 202, 205, 207, 210, 211, 212, 216 and 220.

44. The BPN' variant of claim 43, wherein two or more substitutions occur in the first loop region.

45. The BPN' variant of claim 43, wherein two or more substitutions occur in the second loop region.

46. The BPN' variant of claim 43, wherein two or more substitutions occur in the third loop region.

47. The BPN' variant of claim 43, wherein two or more substitutions occur in the fourth loop region.

48. The BPN' variant of claim 43, wherein two or more substitutions occur in the fifth loop region.

49. The BPN' variant of claim 43, wherein the wild-type amino acid sequence further comprises a sixth loop region, wherein the modified amino acid sequence further comprises one or more substitutions in the sixth loop region; wherein the substitution(s) in the sixth loop region occurs at one or more of positions 199, 200, 201, 202, 203, 204, 205, 206, 207, 208, 209, 210, 211, 212, 213, 214, 215, 216, 218, 219 or 220; wherein a. when a substitution occurs at position 199, the substituting amino acid is Cys, Ala, His, Thr, Pro, Gly, Gln, Asn, Ser, Asp or Glu;

b. when a substitution occurs at position 200, the substituting amino acid is His, Thr, Pro, Gly, Gln, Asn, Ser, Asp or Glu;

c. when a substitution occurs at position 201, the substituting amino acid is Gly, Gln, Asn, Ser, Asp or Glu;

d. when a substitution occurs at position 202, the substituting amino acid is Pro, Gln, Asn, Ser, Asp or Glu;

e. when a substitution occurs at position 203, the substituting amino acid is Met, Cys, His, Pro, Gly, Gln, Asn, Ser, Asp or Glu;

f. when a substitution occurs at position 204, the substituting amino acid is Glu;

g. when a substitution occurs at position 205, the substituting amino acid is Leu, Met, Cys, Ala, His, Thr, Pro, Gly, Gln, Asn, Ser, Asp or Glu;

h. when a substitution occurs at position 206, the substituting amino acid is Pro, Asn or Ser;

i. when a substitution occurs at position 207, the substituting amino acid is Asp or Glu;

j. when a substitution occurs at position 208, the substituting amino acid is Pro, Gly, Gln, Asn or Ser;

k. when a substitution occurs at position 209, the substituting amino acid is Ile, Val, Met, Cys, Ala, His, Thr, Pro, Gly, Gln, Asn, Ser, Asp or Glu;

l. when a substitution occurs at position 210, the substituting amino acid is Gly, Gln, Asn, Ser, Asp or Glu;

m. when a substitution occurs at position 211, the substituting amino acid is Ala, Pro, Gln, Asn, Ser, Asp or Glu;

n. when a substitution occurs at position 212, the substituting amino acid is Gln, Ser, Asp or Glu;

o. when a substitution occurs at position 213, the substituting amino acid is Trp, Phe, Tyr, Leu, Ile, Val, Met, Cys, Ala, His, Pro, Gly, Gln, Asn, Ser or Glu; but when position 213 is substituted the variant is not a double, triple, quadruple, or quintuple mutation variant having substitutions at positions selected from the group consisting of 104, 155, 156, and 166;

p. when a substitution occurs at position 214, the substituting amino acid is Phe, Leu, Ile, Val, Met, Cys, Ala, His, Pro, Gly, Gln or Asn; but when position 214 is substituted the variant is not a double, triple, quadruple, or quintuple mutation variant having substitutions at positions selected from the group consisting of 104, 155, 156, and 166;

q. when a substitution occurs at position 215, the substituting amino acid is Thr, Pro, Gln, Asn, Ser, Asp or Glu; but when position 215 is substituted the variant is not a double, triple, quadruple, or quintuple mutation variant having substitutions at positions selected from the group consisting of 104, 155, 156, and 166;

r. when a substitution occurs at position 216, the substituting amino acid is His, Thr, Pro, Gly, Gln, Asn, Ser, Asp or Glu;

s. when a substitution occurs at position 218, the substituting amino acid is Glu;

t. when a substitution occurs at position 219, the substituting amino acid is Pro, Gln, Asn, Ser, Asp or Glu; and u. when a substitution occurs at position 220, the substituting amino acid is Pro, Gly, Gln, Asn, Asp or Glu;

whereby the BPN' variant has decreased adsorption to, and increased hydrolysis of, an insoluble substrate as compared to wild-type subtilisin BPN'.

50. A BPN' variant according to claim 43 wherein substitutions occur as follows:

a. at position 59, the substituting amino acid is Asp;

b. at position 95, the substituting amino acid is Glu;

c. at position 126, the substituting amino acid is Glu;

d. at position 157, the substituting amino acid is Asp; and e. at position 187, the substituting amino acid is Glu.

51. A cleaning composition selected from the group consisting of a hard surface cleaning composition, a dishwashing composition, an oral cleaning composition, a denture cleansing composition, a contact lens cleaning composition and a fabric cleaning composition, wherein the cleaning composition comprises the BPN' variant of claim 8 and a cleaning composition carrier.

52. The cleaning composition of claim 51, wherein the cleaning composition is a hard surface cleaning composition.

53. The cleaning composition of claim 51, wherein the cleaning composition is a fabric cleaning composition.

54. The fabric cleaning composition of claim 53, wherein the composition is in the form of a liquid.

55. The fabric cleaning composition of claim 54, wherein the composition comprises at least about 5% surfactant and at least about 5% builder, by weight of the composition.

56. The fabric cleaning composition of claim 55 further comprising cleaning composition materials selected from the group consisting of solvents, buffers, enzymes, soil release agents, clay soil removal agents, dispersing agents, brighteners, suds supressors, fabric softeners, suds boosters, enzyme stabilizers, bleaching agents, dyes, perfumes, and mixtures thereof.

57. The fabric cleaning composition of claim 55 further comprising at least one bleaching agent.

58. A cleaning composition selected from the group consisting of a hard surface cleaning composition, a dishwashing composition, an oral cleaning composition, a denture cleansing composition, a contact lens cleaning composition and a fabric cleaning composition, wherein the cleaning composition comprises the BPN' variant of claim 14 and a cleaning composition carrier.

59. The cleaning composition of claim 58, wherein the cleaning composition is a hard surface cleaning composition.

60. The cleaning composition of claim 58, wherein the cleaning composition is a fabric cleaning composition.

61. The fabric cleaning composition of claim 60, wherein the composition comprises at least about 5% surfactant and at least about 5% builder, by weight of the composition.

62. AN isolated mutant BPN' gene encoding the BPN' variant of claim 1.

63. AN isolated mutant BPN' gene encoding the BPN' variant of claim 7.

* * * * *

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
      (A) LENGTH: 275 amino acids
      (B) TYPE: amino acid
      (D) TOPOLOGY: linear (ii) MOLECULE TYPE: protein (xi) SEQUENCE DESCRIPTION: SEQ ID NO:1:

Ala Gln Ser Val Pro Tyr Gly Val Ser Gln Ile Lys Ala Pro Ala Leu
1            5                 10              15

```
His Ser Gln Gly Tyr Thr Gly Ser Asn Val Lys Val Ala Val Ile Asp
            20              25              30

Ser Gly Ile Asp Ser Ser His Pro Asp Leu Lys Val Ala Gly Gly Ala
            35              40              45

Ser Met Val Pro Ser Glu Thr Asn Pro Phe Gln Asp Asn Asn Ser His
        50              55              60

Gly Thr His Val Ala Gly Thr Val Ala Ala Leu Asn Asn Ser Ile Gly
65              70              75              80

Val Leu Gly Val Ala Pro Ser Ala Ser Leu Tyr Ala Val Lys Val Leu
            85              90              95

Gly Ala Asp Gly Ser Gly Gln Tyr Ser Trp Ile Ile Asn Gly Ile Glu
            100             105             110

Trp Ala Ile Ala Asn Asn Met Asp Val Ile Asn Met Ser Leu Gly Gly
        115             120             125

Pro Ser Gly Ser Ala Ala Leu Lys Ala Ala Val Asp Lys Ala Val Ala
    130             135             140

Ser Gly Val Val Val Ala Ala Ala Gly Asn Glu Gly Thr Ser Gly
145             150             155             160

Ser Ser Ser Thr Val Gly Tyr Pro Gly Lys Tyr Pro Ser Val Ile Ala
            165             170             175

Val Gly Ala Val Asp Ser Ser Asn Gln Arg Ala Ser Phe Ser Ser Val
            180             185             190

Gly Pro Glu Leu Asp Val Met Ala Pro Gly Val Ser Ile Gln Ser Thr
        195             200             205

Leu Pro Gly Asn Lys Tyr Gly Ala Tyr Asn Gly Thr Ser Met Ala Ser
    210             215             220

Pro His Val Ala Gly Ala Ala Ala Leu Ile Leu Ser Lys His Pro Asn
225             230             235             240

Trp Thr Asn Thr Gln Val Arg Ser Ser Leu Glu Asn Thr Thr Thr Lys
            245             250             255

Leu Gly Asp Ser Phe Tyr Tyr Gly Lys Gly Leu Ile Asn Val Gln Ala
            260             265             270

Ala Ala Gln
    275
```